(12) United States Patent
Frohberg et al.

(10) Patent No.: US 8,350,122 B2
(45) Date of Patent: Jan. 8, 2013

(54) STARCHES WITH HIGH AMYLOSE CONTENT AND IMPROVED PROCESSING PROPERTIES

(75) Inventors: Claus Frohberg, Kleinmachnow (DE); Ursula La Cognata, Berlin (DE)

(73) Assignee: Bayer Cropscience AG, Monheim Am Rhein (DE)

( * ) Notice: Subject to any disclaimer, the term of this patent is extended or adjusted under 35 U.S.C. 154(b) by 9 days.

(21) Appl. No.: 12/666,009

(22) PCT Filed: Jun. 25, 2008

(86) PCT No.: PCT/EP2008/005438
§ 371 (c)(1),
(2), (4) Date: Dec. 22, 2009

(87) PCT Pub. No.: WO2009/000557
PCT Pub. Date: Dec. 31, 2008

(65) Prior Publication Data
US 2010/0189870 A1    Jul. 29, 2010

Related U.S. Application Data

(60) Provisional application No. 60/937,194, filed on Jun. 26, 2007, provisional application No. 61/069,293, filed on Mar. 13, 2008, provisional application No. 61/127,802, filed on May 15, 2008.

(30) Foreign Application Priority Data

Jun. 25, 2007  (EP) .................... 07075524
Mar. 12, 2008  (EP) .................... 08075190
May 15, 2008   (EP) .................... 08075500

(51) Int. Cl.
*A01H 5/00*    (2006.01)
*C12N 15/82*   (2006.01)
*C12P 19/34*   (2006.01)

(52) U.S. Cl. .................... 800/284; 800/300.1; 536/102; 435/468; 435/419

(58) Field of Classification Search .................... None
See application file for complete search history.

(56) References Cited

U.S. PATENT DOCUMENTS

2003/0150023 A1    8/2003   Klucinec et al.
2006/0282917 A1*  12/2006   Lanahan et al. ............. 800/284

FOREIGN PATENT DOCUMENTS

| WO | WO 02/34923    |   | 5/2002  |
| WO | WO/02/34923    | * | 5/2002  |
| WO | WO 02/101059   |   | 12/2002 |
| WO | WO 03/071860   |   | 9/2003  |
| WO | WO/03/711860   | * | 9/2003  |
| WO | WO 2005/002359 |   | 1/2005  |

OTHER PUBLICATIONS

Wolf et al (Cereal Chemistry 52 (6) 765-770).*
Perez-Sira et al (Determination of the Correlation Between Amylose and Phosphorus Content and Gelatinization Profile of Starches and Flours Obtained From Edible Tropical Tubers Using Differential Scanning Calorimetry and Atomic Absorption Spectroscopy. Master's Thesis, Nov. 2000, University of Wisconsin).*
Blennow et al (Trends in Plant Science vol. 7 No. 10 Oct. 2002).*
Blennow, et al., Structure function relationships of transgenic starches with engineered phosphate substitution and starch branching, Intern. J. Biol. Macromol., Aug. 2005, 36(3):159-168, Butterworth & Co., Guildford, GB.
Kyung-Nam, et al., Molecular cloning and characterization of the amylose-extender gene encoding starch branching enzyme IIB in maise, Plant Molecular Bio., Dec. 1998, 38(6):945-956.

\* cited by examiner

*Primary Examiner* — Brent T Page
*Assistant Examiner* — Lee A Visone
(74) *Attorney, Agent, or Firm* — Hunton & Williams, LLP

(57) ABSTRACT

The present invention relates to maize starches with an apparent amylose content between 35 wt. % and 90 wt. % and improved processing properties relative to conventional high-amylose maize starches. Furthermore, the present invention relates to maize meals and foodstuffs containing these maize starches or maize meals. In addition, the present invention relates to methods of production of said maize starches/maize meals and maize plants which synthesize these maize starches. Moreover, the present invention relates to wheat starches with an apparent amylose content between 35 wt. % and 90 wt. % and improved processing properties, and wheat meals and foodstuffs containing said wheat starches or wheat meals. Moreover, the present invention relates to methods of production of said wheat starches/wheat meals and wheat plants which synthesize these wheat starches.

23 Claims, 3 Drawing Sheets

1 = Mais-Wiltyppflanze A188
2 = SC16
8 = SC 16 x ae1
11 = ae1

SEQUENCE LISTING

```
<160> NUMBER OF SEQ ID NOS: 16

<210> SEQ ID NO 1
<211> LENGTH: 4851
<212> TYPE: DNA
<213> ORGANISM: Solanum tuberosum
<220> FEATURE:
<221> NAME/KEY: transit_peptide
<222> LOCATION: (1)..(77)
<220> FEATURE:
<221> NAME/KEY: CDS
<222> LOCATION: (105)..(4499)
<300> PUBLICATION INFORMATION:
<308> DATABASE ACCESSION NUMBER: EMBL / Y09533
<309> DATABASE ENTRY DATE: 1998-07-30
<313> RELEVANT RESIDUES IN SEQ ID NO: (1)..(4499)

<400> SEQUENCE: 1
catcttcatc gaatttctcg aagcttcttc gctaatttcc tggtttcttc actcaaaatc      60
gacgtttcta gctgaacttg agtgaattaa gccagtggga ggat atg agt aat tcc     116
                                                Met Ser Asn Ser
                                                  1 tta ggg aat aac ttg ctg tac cag gga ttc cta acc tca aca gtg ttg     164
Leu Gly Asn Asn Leu Leu Tyr Gln Gly Phe Leu Thr Ser Thr Val Leu
  5                  10                  15                  20 gaa cat aaa agt aga atc agt cct cct tgt gtt gga ggc aat tct ttg     212
Glu His Lys Ser Arg Ile Ser Pro Pro Cys Val Gly Gly Asn Ser Leu
                 25                  30                  35 ttt caa caa caa gtg atc tcg aaa tca cct tta tca act gag ttt cga     260
Phe Gln Gln Gln Val Ile Ser Lys Ser Pro Leu Ser Thr Glu Phe Arg
             40                  45                  50 ggt aac agg tta aag gtg cag aaa aag aaa ata cct atg gaa aag aag     308
Gly Asn Arg Leu Lys Val Gln Lys Lys Lys Ile Pro Met Glu Lys Lys
         55                  60                  65 cgt gct ttt tct agt tct cct cat gct gta ctt acc act gat acc tct     356
Arg Ala Phe Ser Ser Ser Pro His Ala Val Leu Thr Thr Asp Thr Ser
     70                  75                  80 tct gag cta gca gaa aag ttc agt cta ggg ggg aat att gag cta cag     404
Ser Glu Leu Ala Glu Lys Phe Ser Leu Gly Gly Asn Ile Glu Leu Gln
 85                  90                  95                 100 gtt gat gtt agg cct ccc act tca ggt gat gtg tcc ttt gtg gat ttt     452
Val Asp Val Arg Pro Pro Thr Ser Gly Asp Val Ser Phe Val Asp Phe
                105                 110                 115 caa gta aca aat ggt agt gat aaa ctg ttt ttg cac tgg ggg gca gta     500
Gln Val Thr Asn Gly Ser Asp Lys Leu Phe Leu His Trp Gly Ala Val
            120                 125                 130 aaa ttc ggg aaa gaa aca tgg tct ctt ccg aat gat cgt cca gat ggg     548
Lys Phe Gly Lys Glu Thr Trp Ser Leu Pro Asn Asp Arg Pro Asp Gly
        135                 140                 145 acc aaa gtg tac aag aac aaa gca ctt aga act cca ttt gtt aaa tct     596
Thr Lys Val Tyr Lys Asn Lys Ala Leu Arg Thr Pro Phe Val Lys Ser
    150                 155                 160 ggc tct aac tcc atc ctg aga ctg gag ata cga gac act gct atc gaa     644
Gly Ser Asn Ser Ile Leu Arg Leu Glu Ile Arg Asp Thr Ala Ile Glu
165                 170                 175                 180 gct att gag ttt ctc ata tac gat gaa gcc cac gat aaa tgg ata aag     692
Ala Ile Glu Phe Leu Ile Tyr Asp Glu Ala His Asp Lys Trp Ile Lys
                185                 190                 195
```

| | | |
|---|---|---|
| aat aat ggt ggt aat ttt cgt gtc aaa ttg tca aga aaa gag ata cga<br>Asn Asn Gly Gly Asn Phe Arg Val Lys Leu Ser Arg Lys Glu Ile Arg<br>           200                       205                     210 | 740 |
| ggc cca gat gtt tct gtt cct gag gag ctt gta cag atc caa tca tat<br>Gly Pro Asp Val Ser Val Pro Glu Glu Leu Val Gln Ile Gln Ser Tyr<br>215                       220                     225 | 788 |
| ttg agg tgg gag agg aag gga aaa cag aat tac ccc cct gag aaa gag<br>Leu Arg Trp Glu Arg Lys Gly Lys Gln Asn Tyr Pro Pro Glu Lys Glu<br>     230                   235                   240 | 836 |
| aag gag gaa tat gag gct gct cga act gtg cta cag gag gaa ata gct<br>Lys Glu Glu Tyr Glu Ala Ala Arg Thr Val Leu Gln Glu Glu Ile Ala<br>245                   250                   255                 260 | 884 |
| cgt ggt gct tcc ata cag gac att cga gca agg cta aca aaa act aat<br>Arg Gly Ala Ser Ile Gln Asp Ile Arg Ala Arg Leu Thr Lys Thr Asn<br>               265                   270                 275 | 932 |
| gat aaa agt caa agc aaa gaa gag cct ctt cat gta aca aag agt gat<br>Asp Lys Ser Gln Ser Lys Glu Glu Pro Leu His Val Thr Lys Ser Asp<br>         280                   285                   290 | 980 |
| ata cct gat gac ctt gcc caa gca caa gct tac att agg tgg gag aaa<br>Ile Pro Asp Asp Leu Ala Gln Ala Gln Ala Tyr Ile Arg Trp Glu Lys<br>295                   300                   305 | 1028 |
| gca gga aag ccg aac tat cct cca gaa aag caa att gaa gaa ctc gaa<br>Ala Gly Lys Pro Asn Tyr Pro Pro Glu Lys Gln Ile Glu Glu Leu Glu<br>     310                   315                   320 | 1076 |
| gaa gca aga aga gaa ttg caa ctt gag ctt gag aaa ggc att acc ctt<br>Glu Ala Arg Arg Glu Leu Gln Leu Glu Leu Glu Lys Gly Ile Thr Leu<br>325                   330                   335                 340 | 1124 |
| gat gag ttg cgg aaa acg att aca aaa ggg gag ata aaa act aag gtg<br>Asp Glu Leu Arg Lys Thr Ile Thr Lys Gly Glu Ile Lys Thr Lys Val<br>               345                   350                 355 | 1172 |
| gaa aag cac ctg aaa aga agt tct ttt gcc gtt gaa aga atc caa aga<br>Glu Lys His Leu Lys Arg Ser Ser Phe Ala Val Glu Arg Ile Gln Arg<br>         360                   365                   370 | 1220 |
| aag aag aga gac ttt ggg cat ctt att aat aag tat act tcc agt cct<br>Lys Lys Arg Asp Phe Gly His Leu Ile Asn Lys Tyr Thr Ser Ser Pro<br>375                   380                   385 | 1268 |
| gca gta caa gta caa aag gtc ttg gaa gaa cca cca gcc tta tct aaa<br>Ala Val Gln Val Gln Lys Val Leu Glu Glu Pro Pro Ala Leu Ser Lys<br>     390                   395                   400 | 1316 |
| att aag ctg tat gcc aag gag aag gag gag cag att gat gat ccg atc<br>Ile Lys Leu Tyr Ala Lys Glu Lys Glu Glu Gln Ile Asp Asp Pro Ile<br>405                   410                   415                 420 | 1364 |
| cta aat aaa aag atc ttt aag gtc gat gat ggg gag cta ctg gta ctg<br>Leu Asn Lys Lys Ile Phe Lys Val Asp Asp Gly Glu Leu Leu Val Leu<br>               425                   430                 435 | 1412 |
| gta gca aag tcc tct ggg aag aca aaa gta cat cta gct aca gat ctg<br>Val Ala Lys Ser Ser Gly Lys Thr Lys Val His Leu Ala Thr Asp Leu<br>         440                   445                   450 | 1460 |
| aat cag cca att act ctt cac tgg gca tta tcc aaa agt cct gga gag<br>Asn Gln Pro Ile Thr Leu His Trp Ala Leu Ser Lys Ser Pro Gly Glu<br>455                   460                   465 | 1508 |
| tgg atg gta cca cct tca agc ata ttg cct cct ggg tca att att tta<br>Trp Met Val Pro Pro Ser Ser Ile Leu Pro Pro Gly Ser Ile Ile Leu<br>     470                   475                   480 | 1556 |
| gac aag gct gcc gaa aca cct ttt tca gcc agt tct tct gat ggt cta<br>Asp Lys Ala Ala Glu Thr Pro Phe Ser Ala Ser Ser Ser Asp Gly Leu<br>485                   490                   495                 500 | 1604 |
| act tct aag gta caa tct ttg gat ata gta att gaa gat ggc aat ttt<br>Thr Ser Lys Val Gln Ser Leu Asp Ile Val Ile Glu Asp Gly Asn Phe<br>               505                   510                 515 | 1652 |

| | | |
|---|---|---|
| gtg ggg atg cca ttt gtt ctt ttg tct ggt gaa aaa tgg att aag aac<br>Val Gly Met Pro Phe Val Leu Leu Ser Gly Glu Lys Trp Ile Lys Asn<br>520                                525                              530 | 1700 |
| caa ggg tcg gat ttc tat gtt ggc ttc agt gct gca tcc aaa tta gca<br>Gln Gly Ser Asp Phe Tyr Val Gly Phe Ser Ala Ala Ser Lys Leu Ala<br>535                                540                              545 | 1748 |
| ctc aag gct gct ggg gat ggc agt gga act gca aag tct tta ctg gat<br>Leu Lys Ala Ala Gly Asp Gly Ser Gly Thr Ala Lys Ser Leu Leu Asp<br>550                                555                              560 | 1796 |
| aaa ata gca gat atg gaa agt gag gct cag aag tca ttt atg cac cgg<br>Lys Ile Ala Asp Met Glu Ser Glu Ala Gln Lys Ser Phe Met His Arg<br>565                                570                              575                      580 | 1844 |
| ttt aat att gca gct gac ttg ata gaa gat gcc act agt gct ggt gaa<br>Phe Asn Ile Ala Ala Asp Leu Ile Glu Asp Ala Thr Ser Ala Gly Glu<br>                         585                                590                              595 | 1892 |
| ctt ggt ttt gct gga att ctt gta tgg atg agg ttc atg gct aca agg<br>Leu Gly Phe Ala Gly Ile Leu Val Trp Met Arg Phe Met Ala Thr Arg<br>                     600                                605                              610 | 1940 |
| caa ctg ata tgg aac aaa aac tat aac gta aaa cca cgt gaa ata agc<br>Gln Leu Ile Trp Asn Lys Asn Tyr Asn Val Lys Pro Arg Glu Ile Ser<br>               615                              620                              625 | 1988 |
| aag gct cag gac aga ctt aca gac ttg ttg cag aat gct ttc acc agt<br>Lys Ala Gln Asp Arg Leu Thr Asp Leu Leu Gln Asn Ala Phe Thr Ser<br>630                                635                              640 | 2036 |
| cac cct cag tac cgt gaa att ttg cgg atg att atg tca act gtt gga<br>His Pro Gln Tyr Arg Glu Ile Leu Arg Met Ile Met Ser Thr Val Gly<br>645                                650                              655                      660 | 2084 |
| cgt gga ggt gaa ggg gat gta gga cag cga att agg gat gaa att ttg<br>Arg Gly Gly Glu Gly Asp Val Gly Gln Arg Ile Arg Asp Glu Ile Leu<br>                     665                                670                              675 | 2132 |
| gtc atc cag agg aac aat gac tgc aag ggt ggt atg atg caa gaa tgg<br>Val Ile Gln Arg Asn Asn Asp Cys Lys Gly Gly Met Met Gln Glu Trp<br>               680                              685                              690 | 2180 |
| cat cag aaa ttg cat aat aat act agt cct gat gat gtt gtg atc tgt<br>His Gln Lys Leu His Asn Asn Thr Ser Pro Asp Asp Val Val Ile Cys<br>                     695                                700                              705 | 2228 |
| cag gca tta att gac tac atc aag agt gat ttt gat ctt ggt gtt tat<br>Gln Ala Leu Ile Asp Tyr Ile Lys Ser Asp Phe Asp Leu Gly Val Tyr<br>710                                715                              720 | 2276 |
| tgg aaa acc ctg aat gag aac gga ata aca aaa gag cgt ctt ttg agt<br>Trp Lys Thr Leu Asn Glu Asn Gly Ile Thr Lys Glu Arg Leu Leu Ser<br>725                                730                              735                      740 | 2324 |
| tat gac cgt gct atc cat tct gaa cca aat ttt aga gga gat caa aag<br>Tyr Asp Arg Ala Ile His Ser Glu Pro Asn Phe Arg Gly Asp Gln Lys<br>                     745                                750                              755 | 2372 |
| ggt ggt ctt ttg cgt gat tta ggt cac tat atg aga aca ttg aag gca<br>Gly Gly Leu Leu Arg Asp Leu Gly His Tyr Met Arg Thr Leu Lys Ala<br>                       760                                765                              770 | 2420 |
| gtt cat tca ggt gca gat ctt gag tct gct att gca aac tgc atg ggc<br>Val His Ser Gly Ala Asp Leu Glu Ser Ala Ile Ala Asn Cys Met Gly<br>               775                              780                              785 | 2468 |
| tac aaa act gag gga gaa ggc ttt atg gtt gga gtc cag ata aat cct<br>Tyr Lys Thr Glu Gly Glu Gly Phe Met Val Gly Val Gln Ile Asn Pro<br>790                                795                              800 | 2516 |
| gta tca ggc ttg cca tct ggc ttt cag gac ctc ctc cat ttt gtc tta<br>Val Ser Gly Leu Pro Ser Gly Phe Gln Asp Leu Leu His Phe Val Leu<br>805                                810                              815                      820 | 2564 |
| gac cat gtg gaa gat aaa aat gtg gaa act ctt ctt gag aga ttg cta<br>Asp His Val Glu Asp Lys Asn Val Glu Thr Leu Leu Glu Arg Leu Leu<br>                     825                                830                              835 | 2612 |

|  |  |
|---|---|
| gag gct cgt gag gag ctt agg ccc ttg ctt ctc aaa cca aac aac cgt<br>Glu Ala Arg Glu Glu Leu Arg Pro Leu Leu Leu Lys Pro Asn Asn Arg<br>840     845     850 | 2660 |
| cta aag gat ctg ctg ttt ttg gac ata gca ctt gat tct aca gtt aga<br>Leu Lys Asp Leu Leu Phe Leu Asp Ile Ala Leu Asp Ser Thr Val Arg<br>855     860     865 | 2708 |
| aca gca gta gaa agg gga tat gaa gaa ttg aac aac gct aat cct gag<br>Thr Ala Val Glu Arg Gly Tyr Glu Glu Leu Asn Asn Ala Asn Pro Glu<br>870     875     880 | 2756 |
| aaa atc atg tac ttc atc tcc ctc gtt ctt gaa aat ctc gca ctc tct<br>Lys Ile Met Tyr Phe Ile Ser Leu Val Leu Glu Asn Leu Ala Leu Ser<br>885     890     895     900 | 2804 |
| gtg gac gat aat gaa gat ctt gtt tat tgc ttg aag gga tgg aat caa<br>Val Asp Asp Asn Glu Asp Leu Val Tyr Cys Leu Lys Gly Trp Asn Gln<br>905     910     915 | 2852 |
| gct ctt tca atg tcc aat ggt ggg gac aac cat tgg gct tta ttt gca<br>Ala Leu Ser Met Ser Asn Gly Gly Asp Asn His Trp Ala Leu Phe Ala<br>920     925     930 | 2900 |
| aaa gct gtg ctt gac aga acc cgt ctt gca ctt gca agc aag gca gag<br>Lys Ala Val Leu Asp Arg Thr Arg Leu Ala Leu Ala Ser Lys Ala Glu<br>935     940     945 | 2948 |
| tgg tac cat cac tta ttg cag cca tct gcc gaa tat cta gga tca ata<br>Trp Tyr His His Leu Leu Gln Pro Ser Ala Glu Tyr Leu Gly Ser Ile<br>950     955     960 | 2996 |
| ctt ggg gtg gac caa tgg gct ttg aac ata ttt act gaa gaa att ata<br>Leu Gly Val Asp Gln Trp Ala Leu Asn Ile Phe Thr Glu Glu Ile Ile<br>965     970     975     980 | 3044 |
| cgt gct gga tca gca gct tca tta tcc tct ctt ctt aat aga ctc gat<br>Arg Ala Gly Ser Ala Ala Ser Leu Ser Ser Leu Leu Asn Arg Leu Asp<br>985     990     995 | 3092 |
| ccc gtg ctt cgg aaa act gca aat cta gga agt tgg cag att atc<br>Pro Val Leu Arg Lys Thr Ala Asn Leu Gly Ser Trp Gln Ile Ile<br>1000     1005     1010 | 3137 |
| agt cca gtt gaa gcc gtt gga tat gtt gtc gtt gtg gat gag ttg<br>Ser Pro Val Glu Ala Val Gly Tyr Val Val Val Val Asp Glu Leu<br>1015     1020     1025 | 3182 |
| ctt tca gtt cag aat gaa atc tac gag aag ccc acg atc tta gta<br>Leu Ser Val Gln Asn Glu Ile Tyr Glu Lys Pro Thr Ile Leu Val<br>1030     1035     1040 | 3227 |
| gca aaa tct gtt aaa gga gag gag gaa att cct gat ggt gct gtt<br>Ala Lys Ser Val Lys Gly Glu Glu Glu Ile Pro Asp Gly Ala Val<br>1045     1050     1055 | 3272 |
| gcc ctg ata aca cca gac atg cca gat gtt ctt tca cat gtt tct<br>Ala Leu Ile Thr Pro Asp Met Pro Asp Val Leu Ser His Val Ser<br>1060     1065     1070 | 3317 |
| gtt cga gct aga aat ggg aag gtt tgc ttt gct aca tgc ttt gat<br>Val Arg Ala Arg Asn Gly Lys Val Cys Phe Ala Thr Cys Phe Asp<br>1075     1080     1085 | 3362 |
| ccc aat ata ttg gct gac ctc caa gca aag gaa gga agg att ttg<br>Pro Asn Ile Leu Ala Asp Leu Gln Ala Lys Glu Gly Arg Ile Leu<br>1090     1095     1100 | 3407 |
| ctc tta aag cct aca cct tca gac ata atc tat agt gag gtg aat<br>Leu Leu Lys Pro Thr Pro Ser Asp Ile Ile Tyr Ser Glu Val Asn<br>1105     1110     1115 | 3452 |
| gag att gag ctc caa agt tca agt aac ttg gta gaa gct gaa act<br>Glu Ile Glu Leu Gln Ser Ser Ser Asn Leu Val Glu Ala Glu Thr<br>1120     1125     1130 | 3497 |
| tca gca aca ctt aga ttg gtg aaa aag caa ttt ggt ggt tgt tac<br>Ser Ala Thr Leu Arg Leu Val Lys Lys Gln Phe Gly Gly Cys Tyr<br>1135     1140     1145 | 3542 |

| | | | | | | | | | | | |
|---|---|---|---|---|---|---|---|---|---|---|---|
| gca | ata | tca | gca | gat | gaa | ttc | aca | agt | gaa | atg | gtt | gga | gct | aaa | 3587 |
| Ala | Ile | Ser | Ala | Asp | Glu | Phe | Thr | Ser | Glu | Met | Val | Gly | Ala | Lys | |
| | | 1150 | | | | | 1155 | | | | | 1160 | | | |

| tca | cgt | aat | att | gca | tat | ctg | aaa | gga | aaa | gtg | cct | tcc | tcg | gtg | 3632 |
| Ser | Arg | Asn | Ile | Ala | Tyr | Leu | Lys | Gly | Lys | Val | Pro | Ser | Ser | Val | |
| 1165 | | | | | 1170 | | | | | 1175 | | | | | |

| gga | att | cct | acg | tca | gta | gct | ctt | cca | ttt | gga | gtc | ttt | gag | aaa | 3677 |
| Gly | Ile | Pro | Thr | Ser | Val | Ala | Leu | Pro | Phe | Gly | Val | Phe | Glu | Lys | |
| | | 1180 | | | | | 1185 | | | | | 1190 | | | |

| gta | ctt | tca | gac | gac | ata | aat | cag | gga | gtg | gca | aaa | gag | ttg | caa | 3722 |
| Val | Leu | Ser | Asp | Asp | Ile | Asn | Gln | Gly | Val | Ala | Lys | Glu | Leu | Gln | |
| 1195 | | | | | 1200 | | | | | 1205 | | | | | |

| att | ctg | atg | aaa | aaa | cta | tct | gaa | gga | gac | ttc | agc | gct | ctt | ggt | 3767 |
| Ile | Leu | Met | Lys | Lys | Leu | Ser | Glu | Gly | Asp | Phe | Ser | Ala | Leu | Gly | |
| | 1210 | | | | | 1215 | | | | | 1220 | | | | |

| gaa | att | cgc | aca | acg | gtt | tta | gat | ctt | tca | gca | cca | gct | caa | ttg | 3812 |
| Glu | Ile | Arg | Thr | Thr | Val | Leu | Asp | Leu | Ser | Ala | Pro | Ala | Gln | Leu | |
| | | 1225 | | | | | 1230 | | | | | 1235 | | | |

| gtc | aaa | gag | ctg | aag | gag | aag | atg | cag | ggt | tct | ggc | atg | cct | tgg | 3857 |
| Val | Lys | Glu | Leu | Lys | Glu | Lys | Met | Gln | Gly | Ser | Gly | Met | Pro | Trp | |
| 1240 | | | | | 1245 | | | | | 1250 | | | | | |

| cct | ggt | gat | gaa | ggt | cca | aag | cgg | tgg | gaa | caa | gca | tgg | atg | gcc | 3902 |
| Pro | Gly | Asp | Glu | Gly | Pro | Lys | Arg | Trp | Glu | Gln | Ala | Trp | Met | Ala | |
| | 1255 | | | | | 1260 | | | | | 1265 | | | | |

| ata | aaa | aag | gtg | tgg | gct | tca | aaa | tgg | aat | gag | aga | gca | tac | ttc | 3947 |
| Ile | Lys | Lys | Val | Trp | Ala | Ser | Lys | Trp | Asn | Glu | Arg | Ala | Tyr | Phe | |
| | | 1270 | | | | | 1275 | | | | | 1280 | | | |

| agc | aca | agg | aag | gtg | aaa | ctg | gat | cat | gac | tat | ctg | tgc | atg | gct | 3992 |
| Ser | Thr | Arg | Lys | Val | Lys | Leu | Asp | His | Asp | Tyr | Leu | Cys | Met | Ala | |
| | 1285 | | | | | 1290 | | | | | 1295 | | | | |

| gtc | ctt | gtt | caa | gaa | ata | ata | aat | gct | gat | tat | gca | ttt | gtc | att | 4037 |
| Val | Leu | Val | Gln | Glu | Ile | Ile | Asn | Ala | Asp | Tyr | Ala | Phe | Val | Ile | |
| 1300 | | | | | 1305 | | | | | 1310 | | | | | |

| cac | aca | acc | aac | cca | tct | tcc | gga | gac | gac | tca | gaa | ata | tat | gcc | 4082 |
| His | Thr | Thr | Asn | Pro | Ser | Ser | Gly | Asp | Asp | Ser | Glu | Ile | Tyr | Ala | |
| | | 1315 | | | | | 1320 | | | | | 1325 | | | |

| gag | gtg | gtc | agg | ggc | ctt | ggg | gaa | aca | ctt | gtt | gga | gct | tat | cca | 4127 |
| Glu | Val | Val | Arg | Gly | Leu | Gly | Glu | Thr | Leu | Val | Gly | Ala | Tyr | Pro | |
| | 1330 | | | | | 1335 | | | | | 1340 | | | | |

| gga | cgt | gct | ttg | agt | ttt | atc | tgc | aag | aaa | aag | gat | ctc | aac | tct | 4172 |
| Gly | Arg | Ala | Leu | Ser | Phe | Ile | Cys | Lys | Lys | Lys | Asp | Leu | Asn | Ser | |
| | 1345 | | | | | 1350 | | | | | 1355 | | | | |

| cct | caa | gtg | tta | ggt | tac | cca | agc | aaa | ccg | atc | ggc | ctt | ttc | ata | 4217 |
| Pro | Gln | Val | Leu | Gly | Tyr | Pro | Ser | Lys | Pro | Ile | Gly | Leu | Phe | Ile | |
| | | 1360 | | | | | 1365 | | | | | 1370 | | | |

| aaa | aga | tct | atc | atc | ttc | cga | tct | gat | tcc | aat | ggg | gaa | gat | ttg | 4262 |
| Lys | Arg | Ser | Ile | Ile | Phe | Arg | Ser | Asp | Ser | Asn | Gly | Glu | Asp | Leu | |
| | 1375 | | | | | 1380 | | | | | 1385 | | | | |

| gaa | ggt | tat | gcc | ggt | gct | ggc | ctc | tac | gac | agt | gta | cca | atg | gat | 4307 |
| Glu | Gly | Tyr | Ala | Gly | Ala | Gly | Leu | Tyr | Asp | Ser | Val | Pro | Met | Asp | |
| | | 1390 | | | | | 1395 | | | | | 1400 | | | |

| gag | gag | gaa | aaa | gtt | gta | att | gat | tac | tct | tcc | gac | cca | ttg | ata | 4352 |
| Glu | Glu | Glu | Lys | Val | Val | Ile | Asp | Tyr | Ser | Ser | Asp | Pro | Leu | Ile | |
| | | 1405 | | | | | 1410 | | | | | 1415 | | | |

| act | gat | ggt | aac | ttc | cgc | cag | aca | atc | ctg | tcc | aac | att | gct | cgt | 4397 |
| Thr | Asp | Gly | Asn | Phe | Arg | Gln | Thr | Ile | Leu | Ser | Asn | Ile | Ala | Arg | |
| | | 1420 | | | | | 1425 | | | | | 1430 | | | |

| gct | gga | cat | gct | atc | gag | gag | cta | tat | ggc | tct | cct | caa | gac | att | 4442 |
| Ala | Gly | His | Ala | Ile | Glu | Glu | Leu | Tyr | Gly | Ser | Pro | Gln | Asp | Ile | |
| | 1435 | | | | | 1440 | | | | | 1445 | | | | |

-continued

```
gag ggt gta gtg  agg gat gga aag att  tat gtc gtt cag aca  aga         4487
Glu Gly Val Val  Arg Asp Gly Lys Ile  Tyr Val Val Gln Thr  Arg
             1450                 1455                 1460 cca cag atg tga ttatattctc gttgtatgtt gttcagagaa gaccacagat             4539
Pro Gln Met gtgatcatat tctcattgta tcagatctgt gaccacttac ctgataccct ccatgaagtt       4599
acctgtatga ttatacgtga tccaaagcca tcacatcatg ttcaccttca gctattggag       4659
gagaagtgag aagtaggaat tgcaatatga ggaataataa gaaaacttt gtaaaagcta        4719 aattagctgg gtatgatata gggagaaatg tgtaaacatt gtactatata tagtatatac       4779
acacgcatta tgtattgcat tatgcactga ataatatcgc agcatcaaag aagaaatcct       4839
ttgggtggtt tc                                                           4851
```

<210> SEQ ID NO 2
<211> LENGTH: 1464
<212> TYPE: PRT
<213> ORGANISM: Solanum tuberosum

<400> SEQUENCE: 2

```
Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Val Ile Ser Lys Ser Pro Leu Ser
        35                  40                  45

Thr Glu Phe Arg Gly Asn Arg Leu Lys Val Gln Lys Lys Ile Pro
    50                  55                  60

Met Glu Lys Lys Arg Ala Phe Ser Ser Pro His Ala Val Leu Thr
65                  70                  75                  80

Thr Asp Thr Ser Ser Glu Leu Ala Glu Lys Phe Ser Leu Gly Gly Asn
                85                  90                  95

Ile Glu Leu Gln Val Asp Val Arg Pro Pro Thr Ser Gly Asp Val Ser
            100                 105                 110

Phe Val Asp Phe Gln Val Thr Asn Gly Ser Asp Lys Leu Phe Leu His
        115                 120                 125

Trp Gly Ala Val Lys Phe Gly Lys Glu Thr Trp Ser Leu Pro Asn Asp
    130                 135                 140

Arg Pro Asp Gly Thr Lys Val Tyr Lys Asn Lys Ala Leu Arg Thr Pro
145                 150                 155                 160

Phe Val Lys Ser Gly Ser Asn Ser Ile Leu Arg Leu Glu Ile Arg Asp
                165                 170                 175

Thr Ala Ile Glu Ala Ile Glu Phe Leu Ile Tyr Asp Glu Ala His Asp
            180                 185                 190

Lys Trp Ile Lys Asn Asn Gly Gly Asn Phe Arg Val Lys Leu Ser Arg
        195                 200                 205

Lys Glu Ile Arg Gly Pro Asp Val Ser Val Pro Glu Glu Leu Val Gln
    210                 215                 220

Ile Gln Ser Tyr Leu Arg Trp Glu Arg Lys Gly Lys Gln Asn Tyr Pro
225                 230                 235                 240

Pro Glu Lys Glu Lys Glu Glu Tyr Glu Ala Ala Arg Thr Val Leu Gln
                245                 250                 255

Glu Glu Ile Ala Arg Gly Ala Ser Ile Gln Asp Ile Arg Ala Arg Leu
            260                 265                 270

Thr Lys Thr Asn Asp Lys Ser Gln Ser Lys Glu Glu Pro Leu His Val
```

```
                275                 280                 285
Thr Lys Ser Asp Ile Pro Asp Leu Ala Gln Ala Gln Ala Tyr Ile
290                 295                 300
Arg Trp Glu Lys Ala Gly Lys Pro Asn Tyr Pro Glu Lys Gln Ile
305                 310                 315                 320
Glu Glu Leu Glu Glu Ala Arg Arg Glu Leu Gln Leu Glu Leu Glu Lys
                325                 330                 335
Gly Ile Thr Leu Asp Glu Leu Arg Lys Thr Ile Thr Lys Gly Glu Ile
            340                 345                 350
Lys Thr Lys Val Glu Lys His Leu Lys Arg Ser Ser Phe Ala Val Glu
            355                 360                 365
Arg Ile Gln Arg Lys Lys Arg Asp Phe Gly His Leu Ile Asn Lys Tyr
370                 375                 380
Thr Ser Ser Pro Ala Val Gln Val Gln Lys Val Leu Glu Glu Pro Pro
385                 390                 395                 400
Ala Leu Ser Lys Ile Lys Leu Tyr Ala Lys Glu Lys Glu Glu Gln Ile
                405                 410                 415
Asp Asp Pro Ile Leu Asn Lys Lys Ile Phe Lys Val Asp Asp Gly Glu
                420                 425                 430
Leu Leu Val Leu Val Ala Lys Ser Ser Gly Lys Thr Lys Val His Leu
            435                 440                 445
Ala Thr Asp Leu Asn Gln Pro Ile Thr Leu His Trp Ala Leu Ser Lys
450                 455                 460
Ser Pro Gly Glu Trp Met Val Pro Pro Ser Ile Leu Pro Pro Gly
465                 470                 475                 480
Ser Ile Ile Leu Asp Lys Ala Ala Glu Thr Pro Phe Ser Ala Ser Ser
                485                 490                 495
Ser Asp Gly Leu Thr Ser Lys Val Gln Ser Leu Asp Ile Val Ile Glu
                500                 505                 510
Asp Gly Asn Phe Val Gly Met Pro Phe Val Leu Ser Gly Glu Lys
                515                 520                 525
Trp Ile Lys Asn Gln Gly Ser Asp Phe Tyr Val Gly Phe Ser Ala Ala
530                 535                 540
Ser Lys Leu Ala Leu Lys Ala Ala Gly Asp Gly Ser Gly Thr Ala Lys
545                 550                 555                 560
Ser Leu Leu Asp Lys Ile Ala Asp Met Glu Ser Glu Ala Gln Lys Ser
                565                 570                 575
Phe Met His Arg Phe Asn Ile Ala Ala Asp Leu Ile Glu Asp Ala Thr
            580                 585                 590
Ser Ala Gly Glu Leu Gly Phe Ala Gly Ile Leu Val Trp Met Arg Phe
            595                 600                 605
Met Ala Thr Arg Gln Leu Ile Trp Asn Lys Asn Tyr Asn Val Lys Pro
610                 615                 620
Arg Glu Ile Ser Lys Ala Gln Asp Arg Leu Thr Asp Leu Leu Gln Asn
625                 630                 635                 640
Ala Phe Thr Ser His Pro Gln Tyr Arg Glu Ile Leu Arg Met Ile Met
                645                 650                 655
Ser Thr Val Gly Arg Gly Gly Glu Gly Asp Val Gly Gln Arg Ile Arg
                660                 665                 670
Asp Glu Ile Leu Val Ile Gln Arg Asn Asn Asp Cys Lys Gly Gly Met
            675                 680                 685
Met Gln Glu Trp His Gln Lys Leu His Asn Asn Thr Ser Pro Asp Asp
        690                 695                 700
```

-continued

```
Val Val Ile Cys Gln Ala Leu Ile Asp Tyr Ile Lys Ser Asp Phe Asp
705                 710                 715                 720

Leu Gly Val Tyr Trp Lys Thr Leu Asn Glu Asn Gly Ile Thr Lys Glu
            725                 730                 735

Arg Leu Leu Ser Tyr Asp Arg Ala Ile His Ser Glu Pro Asn Phe Arg
        740                 745                 750

Gly Asp Gln Lys Gly Gly Leu Arg Asp Leu Gly His Tyr Met Arg
    755                 760                 765

Thr Leu Lys Ala Val His Ser Gly Ala Asp Leu Glu Ser Ala Ile Ala
770                 775                 780

Asn Cys Met Gly Tyr Lys Thr Glu Gly Glu Gly Phe Met Val Gly Val
785                 790                 795                 800

Gln Ile Asn Pro Val Ser Gly Leu Pro Ser Gly Phe Gln Asp Leu Leu
                805                 810                 815

His Phe Val Leu Asp His Val Glu Asp Lys Asn Val Glu Thr Leu Leu
            820                 825                 830

Glu Arg Leu Leu Glu Ala Arg Glu Glu Leu Arg Pro Leu Leu Leu Lys
        835                 840                 845

Pro Asn Asn Arg Leu Lys Asp Leu Leu Phe Leu Asp Ile Ala Leu Asp
850                 855                 860

Ser Thr Val Arg Thr Ala Val Glu Arg Gly Tyr Glu Glu Leu Asn Asn
865                 870                 875                 880

Ala Asn Pro Glu Lys Ile Met Tyr Phe Ile Ser Leu Val Leu Glu Asn
                885                 890                 895

Leu Ala Leu Ser Val Asp Asp Asn Glu Asp Leu Val Tyr Cys Leu Lys
            900                 905                 910

Gly Trp Asn Gln Ala Leu Ser Met Ser Asn Gly Gly Asp Asn His Trp
        915                 920                 925

Ala Leu Phe Ala Lys Ala Val Leu Asp Arg Thr Arg Leu Ala Leu Ala
930                 935                 940

Ser Lys Ala Glu Trp Tyr His His Leu Leu Gln Pro Ser Ala Glu Tyr
945                 950                 955                 960

Leu Gly Ser Ile Leu Gly Val Asp Gln Trp Ala Leu Asn Ile Phe Thr
                965                 970                 975

Glu Glu Ile Ile Arg Ala Gly Ser Ala Ala Ser Leu Ser Ser Leu Leu
            980                 985                 990

Asn Arg Leu Asp Pro Val Leu Arg Lys Thr Ala Asn Leu Gly Ser Trp
        995                 1000                1005

Gln Ile Ile Ser Pro Val Ala Val Gly Tyr Val Val Val Val
1010                1015                1020

Asp Glu Leu Leu Ser Val Gln Asn Glu Ile Tyr Glu Lys Pro Thr
1025                1030                1035

Ile Leu Val Ala Lys Ser Val Lys Gly Glu Glu Ile Pro Asp
1040                1045                1050

Gly Ala Val Ala Leu Ile Thr Pro Asp Met Pro Asp Val Leu Ser
1055                1060                1065

His Val Ser Val Arg Ala Arg Asn Gly Lys Val Cys Phe Ala Thr
1070                1075                1080

Cys Phe Asp Pro Asn Ile Leu Ala Asp Leu Gln Ala Lys Glu Gly
1085                1090                1095

Arg Ile Leu Leu Leu Lys Pro Thr Pro Ser Asp Ile Ile Tyr Ser
1100                1105                1110

Glu Val Asn Glu Ile Glu Leu Gln Ser Ser Ser Asn Leu Val Glu
1115                1120                1125
```

Ala Glu Thr Ser Ala Thr Leu Arg Leu Val Lys Lys Gln Phe Gly
    1130                1135                1140

Gly Cys Tyr Ala Ile Ser Ala Asp Glu Phe Thr Ser Glu Met Val
    1145                1150                1155

Gly Ala Lys Ser Arg Asn Ile Ala Tyr Leu Lys Gly Lys Val Pro
    1160                1165                1170

Ser Ser Val Gly Ile Pro Thr Ser Val Ala Leu Pro Phe Gly Val
    1175                1180                1185

Phe Glu Lys Val Leu Ser Asp Asp Ile Asn Gln Gly Val Ala Lys
    1190                1195                1200

Glu Leu Gln Ile Leu Met Lys Lys Leu Ser Glu Gly Asp Phe Ser
    1205                1210                1215

Ala Leu Gly Glu Ile Arg Thr Thr Val Leu Asp Leu Ser Ala Pro
    1220                1225                1230

Ala Gln Leu Val Lys Glu Leu Lys Glu Lys Met Gln Gly Ser Gly
    1235                1240                1245

Met Pro Trp Pro Gly Asp Glu Gly Pro Lys Arg Trp Glu Gln Ala
    1250                1255                1260

Trp Met Ala Ile Lys Lys Val Trp Ala Ser Lys Trp Asn Glu Arg
    1265                1270                1275

Ala Tyr Phe Ser Thr Arg Lys Val Lys Leu Asp His Asp Tyr Leu
    1280                1285                1290

Cys Met Ala Val Leu Val Gln Glu Ile Ile Asn Ala Asp Tyr Ala
    1295                1300                1305

Phe Val Ile His Thr Thr Asn Pro Ser Ser Gly Asp Asp Ser Glu
    1310                1315                1320

Ile Tyr Ala Glu Val Val Arg Gly Leu Gly Glu Thr Leu Val Gly
    1325                1330                1335

Ala Tyr Pro Gly Arg Ala Leu Ser Phe Ile Cys Lys Lys Lys Asp
    1340                1345                1350

Leu Asn Ser Pro Gln Val Leu Gly Tyr Pro Ser Lys Pro Ile Gly
    1355                1360                1365

Leu Phe Ile Lys Arg Ser Ile Ile Phe Arg Ser Asp Ser Asn Gly
    1370                1375                1380

Glu Asp Leu Glu Gly Tyr Ala Gly Ala Gly Leu Tyr Asp Ser Val
    1385                1390                1395

Pro Met Asp Glu Glu Lys Val Val Ile Asp Tyr Ser Ser Asp
    1400                1405                1410

Pro Leu Ile Thr Asp Gly Asn Phe Arg Gln Thr Ile Leu Ser Asn
    1415                1420                1425

Ile Ala Arg Ala Gly His Ala Ile Glu Glu Leu Tyr Gly Ser Pro
    1430                1435                1440

Gln Asp Ile Glu Gly Val Val Arg Asp Gly Lys Ile Tyr Val Val
    1445                1450                1455

Gln Thr Arg Pro Gln Met
    1460

<210> SEQ ID NO 3
<211> LENGTH: 4443
<212> TYPE: DNA
<213> ORGANISM: Curcuma longa
<220> FEATURE:
<221> NAME/KEY: CDS
<222> LOCATION: (1)..(4443)

<400> SEQUENCE: 3

```
atg aac aat tgt gtt gga cat acc tta cct cag caa gct ctg ttt cgg       48
Met Asn Asn Cys Val Gly His Thr Leu Pro Gln Gln Ala Leu Phe Arg
1               5                   10                  15 cct tct gtt gta gaa cgc cat aat aca gct tgc caa cgt tct tct gga       96
Pro Ser Val Val Glu Arg His Asn Thr Ala Cys Gln Arg Ser Ser Gly
            20                  25                  30 aac att ttg tgc act gtt cca tca gca tca aag gca gaa gat gtg cca      144
Asn Ile Leu Cys Thr Val Pro Ser Ala Ser Lys Ala Glu Asp Val Pro
        35                  40                  45 tct ctt aaa cct ttc ctt tca agt aga ttc ctg ggg aag act ccc tat      192
Ser Leu Lys Pro Phe Leu Ser Ser Arg Phe Leu Gly Lys Thr Pro Tyr
    50                  55                  60 gca gga aaa gga aac cca tta aag aaa aat tta aga aca gtt acc atg      240
Ala Gly Lys Gly Asn Pro Leu Lys Lys Asn Leu Arg Thr Val Thr Met
65                  70                  75                  80 agc cct caa gct tta ttg gca gca gat cct gct tca gag ctt gct aga      288
Ser Pro Gln Ala Leu Leu Ala Ala Asp Pro Ala Ser Glu Leu Ala Arg
                85                  90                  95 aaa ttc aag ctg gac acc aat tcc gaa ttg gag gtt act att tgt aag      336
Lys Phe Lys Leu Asp Thr Asn Ser Glu Leu Glu Val Thr Ile Cys Lys
            100                 105                 110 ccc aca tct gag tct cct atg caa att gat ttt caa gta acc aat gtc      384
Pro Thr Ser Glu Ser Pro Met Gln Ile Asp Phe Gln Val Thr Asn Val
        115                 120                 125 agt ggt tcc ttg gtg ctt cat tgg ggt gta att ctc caa aca aga aga      432
Ser Gly Ser Leu Val Leu His Trp Gly Val Ile Leu Gln Thr Arg Arg
    130                 135                 140 gaa tgg tct ctt cct tct cat tat cct gaa gga aca aaa gta tac aaa      480
Glu Trp Ser Leu Pro Ser His Tyr Pro Glu Gly Thr Lys Val Tyr Lys
145                 150                 155                 160 aat caa gct ctc aga act cct ttt act aaa gtt ggc tcg act tgt tca      528
Asn Gln Ala Leu Arg Thr Pro Phe Thr Lys Val Gly Ser Thr Cys Ser
                165                 170                 175 ctg aga tta gag att gat gat cct gaa ata gaa ata gtt gag ttt ctt      576
Leu Arg Leu Glu Ile Asp Asp Pro Glu Ile Glu Ile Val Glu Phe Leu
            180                 185                 190 ata ctg gat gag gca gaa aac aaa tgg tac aaa cat aat ggc cag aat      624
Ile Leu Asp Glu Ala Glu Asn Lys Trp Tyr Lys His Asn Gly Gln Asn
        195                 200                 205 ttt caa gtt cat ttg ttg aaa caa ggc tat caa aat caa cat gtt tca      672
Phe Gln Val His Leu Leu Lys Gln Gly Tyr Gln Asn Gln His Val Ser
    210                 215                 220 gtc tct gga aat cca aat atc att gta cct gaa gac ctt gtg cag att      720
Val Ser Gly Asn Pro Asn Ile Ile Val Pro Glu Asp Leu Val Gln Ile
225                 230                 235                 240 caa gcc ttt ctt agg tgg gaa aga aag ggt agg cag aca tat aca cct      768
Gln Ala Phe Leu Arg Trp Glu Arg Lys Gly Arg Gln Thr Tyr Thr Pro
                245                 250                 255 gat caa gaa aag gag gag tat gaa gca gct aga atg gag ctg ata gaa      816
Asp Gln Glu Lys Glu Glu Tyr Glu Ala Ala Arg Met Glu Leu Ile Glu
            260                 265                 270 gaa ata agt aga ggt atg cct gta gag gag ctt cga tcc aag ttg aca      864
Glu Ile Ser Arg Gly Met Pro Val Glu Glu Leu Arg Ser Lys Leu Thr
        275                 280                 285 gag aaa cca gaa gtc aaa tct gga agt aga gaa gag aaa acc cac aga      912
Glu Lys Pro Glu Val Lys Ser Gly Ser Arg Glu Glu Lys Thr His Arg
    290                 295                 300 gta caa agt cac aaa ggt ggg atc tca gat gat ctt gtg caa ata caa      960
Val Gln Ser His Lys Gly Gly Ile Ser Asp Asp Leu Val Gln Ile Gln
305                 310                 315                 320
```

```
gca ttc atc cga tgg gag aaa gct ggg aaa cca aac tac cct cca gag      1008
Ala Phe Ile Arg Trp Glu Lys Ala Gly Lys Pro Asn Tyr Pro Pro Glu
            325                 330                 335 aag caa ctt atg gag ttt gag gaa gca agg aaa gag ctg cag ctt gag      1056
Lys Gln Leu Met Glu Phe Glu Glu Ala Arg Lys Glu Leu Gln Leu Glu
            340                 345                 350 ttt gat aaa ggt act tct ctg gct gaa cta cgg gaa aag atc atg aag      1104
Phe Asp Lys Gly Thr Ser Leu Ala Glu Leu Arg Glu Lys Ile Met Lys
            355                 360                 365 ggg gat ata tca act aaa gtt ttg aag caa ctg aag gtt gaa aag tat      1152
Gly Asp Ile Ser Thr Lys Val Leu Lys Gln Leu Lys Val Glu Lys Tyr
        370                 375                 380 ttc agc aac aaa aga att cag cgg aag gaa agg gac atc atg gaa att      1200
Phe Ser Asn Lys Arg Ile Gln Arg Lys Glu Arg Asp Ile Met Glu Ile
385                 390                 395                 400 ttg aat aaa aaa gtt gca gaa act cta gat gaa aaa tct tct caa ata      1248
Leu Asn Lys Lys Val Ala Glu Thr Leu Asp Glu Lys Ser Ser Gln Ile
                405                 410                 415 gtc act cct cct aca gtg cta gaa ctc ttg gct aag tct ata cat gag      1296
Val Thr Pro Pro Thr Val Leu Glu Leu Leu Ala Lys Ser Ile His Glu
            420                 425                 430 cag gat ggt gaa tca gtt ctg cat cag aaa atc tat aag ctg gat aat      1344
Gln Asp Gly Glu Ser Val Leu His Gln Lys Ile Tyr Lys Leu Asp Asn
            435                 440                 445 aag aat ctt ctg gta cta gta acc aaa cct ttt gaa agg aca aaa gtt      1392
Lys Asn Leu Leu Val Leu Val Thr Lys Pro Phe Glu Arg Thr Lys Val
        450                 455                 460 tat ttg gct aca gat caa agt gaa cca ctt att tta cac tgg gga tta      1440
Tyr Leu Ala Thr Asp Gln Ser Glu Pro Leu Ile Leu His Trp Gly Leu
465                 470                 475                 480 tca agg aaa tca aga gag tgg atg gta ccc cct aca agt tct att cct      1488
Ser Arg Lys Ser Arg Glu Trp Met Val Pro Pro Thr Ser Ser Ile Pro
                485                 490                 495 cca ggt tca gta ttg cta gaa gag tct tgt gaa acc cct ttt act aag      1536
Pro Gly Ser Val Leu Leu Glu Glu Ser Cys Glu Thr Pro Phe Thr Lys
            500                 505                 510 ggt tta atg gta gat cag tat tat cag gcc att caa ata gag att gat      1584
Gly Leu Met Val Asp Gln Tyr Tyr Gln Ala Ile Gln Ile Glu Ile Asp
            515                 520                 525 ggg ggt gat tat gct gga att ccc ttc gtt ctt cgt tca gac gat aaa      1632
Gly Gly Asp Tyr Ala Gly Ile Pro Phe Val Leu Arg Ser Asp Asp Lys
        530                 535                 540 tgg ata aag aat agt ggt ttg gac ttt tac att gag ttg gac gat aga      1680
Trp Ile Lys Asn Ser Gly Leu Asp Phe Tyr Ile Glu Leu Asp Asp Arg
545                 550                 555                 560 agt att agg aag gct cct ggt gat gga agc ggc att gca aaa tca ttg      1728
Ser Ile Arg Lys Ala Pro Gly Asp Gly Ser Gly Ile Ala Lys Ser Leu
                565                 570                 575 ctt gac aag att gct gac ctg gag acc gag gct caa aaa tct ttt atg      1776
Leu Asp Lys Ile Ala Asp Leu Glu Thr Glu Ala Gln Lys Ser Phe Met
            580                 585                 590 cac agg ttt agt att gca gca gat ctc act gag caa gct aga ggc tct      1824
His Arg Phe Ser Ile Ala Ala Asp Leu Thr Glu Gln Ala Arg Gly Ser
            595                 600                 605 ggc cat cta ggg ctt gtt ggc att ctt gtt tgg atg aga ttc atg gca      1872
Gly His Leu Gly Leu Val Gly Ile Leu Val Trp Met Arg Phe Met Ala
        610                 615                 620 atg aga caa ctc att tgg aat aaa aac tac aat gtc aag cca cgt gag      1920
Met Arg Gln Leu Ile Trp Asn Lys Asn Tyr Asn Val Lys Pro Arg Glu
625                 630                 635                 640
```

```
att agt aaa gct cag gat agg ctc aca gat ctt ctt cag gac ata tat      1968
Ile Ser Lys Ala Gln Asp Arg Leu Thr Asp Leu Leu Gln Asp Ile Tyr
            645                 650                 655 aaa gac ttc ccc cag tat aga gag atc ttg agg atg atc atg gct act      2016
Lys Asp Phe Pro Gln Tyr Arg Glu Ile Leu Arg Met Ile Met Ala Thr
660                 665                 670 gtt ggt agg ggc ggt gaa ggt gat gtt ggt cag cgt atc cga gat gaa      2064
Val Gly Arg Gly Gly Glu Gly Asp Val Gly Gln Arg Ile Arg Asp Glu
    675                 680                 685 ata tta gtt ata cag aga aac aat gac tgc aag gga gga atg atg gag      2112
Ile Leu Val Ile Gln Arg Asn Asn Asp Cys Lys Gly Gly Met Met Glu
690                 695                 700 gaa tgg cat cag aag cta cat aac aac act agc cca gat gat gtt gtg      2160
Glu Trp His Gln Lys Leu His Asn Asn Thr Ser Pro Asp Asp Val Val
705                 710                 715                 720 ata tgc cag gca ctt att gat tat gtt aaa agt gat ttt gac atc agt      2208
Ile Cys Gln Ala Leu Ile Asp Tyr Val Lys Ser Asp Phe Asp Ile Ser
                725                 730                 735 gtg tac tgg gac agt ttg aat aaa aat gga ata acc aag gaa cgt ttg      2256
Val Tyr Trp Asp Ser Leu Asn Lys Asn Gly Ile Thr Lys Glu Arg Leu
            740                 745                 750 ttg agc tat gat cgt gct att cat tct gaa cca agt ttc agg aga gat      2304
Leu Ser Tyr Asp Arg Ala Ile His Ser Glu Pro Ser Phe Arg Arg Asp
        755                 760                 765 cag aaa gaa ggt ctt tta cgt gat cta gga aac tac atg agg acg ttg      2352
Gln Lys Glu Gly Leu Leu Arg Asp Leu Gly Asn Tyr Met Arg Thr Leu
770                 775                 780 aag gca gtt cac tct ggt gca gat ctc gag tct gcc att gct acg tgt      2400
Lys Ala Val His Ser Gly Ala Asp Leu Glu Ser Ala Ile Ala Thr Cys
785                 790                 795                 800 atg ggt tac aaa tct gag cgt caa ggc ttt atg gtt ggc gtt caa ata      2448
Met Gly Tyr Lys Ser Glu Arg Gln Gly Phe Met Val Gly Val Gln Ile
                805                 810                 815 aac ccg ata ggg gga ttg cca tct gga ttc cct ggt cta atg aaa ttc      2496
Asn Pro Ile Gly Gly Leu Pro Ser Gly Phe Pro Gly Leu Met Lys Phe
            820                 825                 830 att cta aaa cat gtt gaa gat aaa aat gtg gag cct ttg ata gag ggg      2544
Ile Leu Lys His Val Glu Asp Lys Asn Val Glu Pro Leu Ile Glu Gly
        835                 840                 845 ttg ctg gag gca cga gtg gaa ctt aga cca ttg ctt ctt agc tct cat      2592
Leu Leu Glu Ala Arg Val Glu Leu Arg Pro Leu Leu Leu Ser Ser His
850                 855                 860 gaa cgg ctg aag gat ctt att ttt ttg gat atc gcc ctt gat tct act      2640
Glu Arg Leu Lys Asp Leu Ile Phe Leu Asp Ile Ala Leu Asp Ser Thr
865                 870                 875                 880 gtc agg aca gct gtt gag aga gga tat gag gaa ttg agt aat gcg gag      2688
Val Arg Thr Ala Val Glu Arg Gly Tyr Glu Glu Leu Ser Asn Ala Glu
                885                 890                 895 cca gag aaa ctt att tac ctt att atg ctg ctt gag aat ctt gca      2736
Pro Glu Lys Leu Ile Tyr Leu Ile Met Leu Leu Glu Asn Leu Ala
            900                 905                 910 ttg tct aca gat gat aat gag gac ctc ata tat tgc ttg aag gga tgg      2784
Leu Ser Thr Asp Asp Asn Glu Asp Leu Ile Tyr Cys Leu Lys Gly Trp
        915                 920                 925 aaa cat tcg atg gag atg tgt aag caa aaa gat gat caa tgg gca cta      2832
Lys His Ser Met Glu Met Cys Lys Gln Lys Asp Asp Gln Trp Ala Leu
930                 935                 940 ttt gct aag tca ttt ctt gac aga acc cgt ctg gct cta tca agc aag      2880
Phe Ala Lys Ser Phe Leu Asp Arg Thr Arg Leu Ala Leu Ser Ser Lys
945                 950                 955                 960
```

```
gca gaa tac tac cat caa att ttg caa cct tca gct gaa tac ctt gga        2928
Ala Glu Tyr Tyr His Gln Ile Leu Gln Pro Ser Ala Glu Tyr Leu Gly
            965                 970                 975 tca ttg ctt gat gtt gat gca ggg gcg gta agc ata ttc aca gaa gaa        2976
Ser Leu Leu Asp Val Asp Ala Gly Ala Val Ser Ile Phe Thr Glu Glu
        980                 985                 990 atc ata cgt gct gga tca gca gct tct tta tct gca ctt ctt cag cga       3024
Ile Ile Arg Ala Gly Ser Ala Ala Ser Leu Ser Ala Leu Leu Gln Arg
    995                 1000                1005 ctt gac cct ctt ctt cgg aaa gtt gca cat ttg gga agc tgg cag            3069
Leu Asp Pro Leu Leu Arg Lys Val Ala His Leu Gly Ser Trp Gln
    1010                1015                1020 gtc ata agc cct gtt gaa gtt gct gga tat gtt gaa att gta gaa            3114
Val Ile Ser Pro Val Glu Val Ala Gly Tyr Val Glu Ile Val Glu
    1025                1030                1035 gaa ttg ctt gct gtc cag aat aaa tca tat aca caa tca aca att            3159
Glu Leu Leu Ala Val Gln Asn Lys Ser Tyr Thr Gln Ser Thr Ile
    1040                1045                1050 ttg gtt gca aaa cat gta agg gga gaa gag gaa ata cca gat ggc            3204
Leu Val Ala Lys His Val Arg Gly Glu Glu Glu Ile Pro Asp Gly
    1055                1060                1065 aca gtt gct gtt tta aca cct gat atg cca gat gtt cta tct cat            3249
Thr Val Ala Val Leu Thr Pro Asp Met Pro Asp Val Leu Ser His
    1070                1075                1080 gtc tct gtg cga gct aga aat agc aag gta tgt ttt gct acc tgc            3294
Val Ser Val Arg Ala Arg Asn Ser Lys Val Cys Phe Ala Thr Cys
    1085                1090                1095 ttt gat gac aat atc ctg gat gag ttt cgg aga aat gca gga aag            3339
Phe Asp Asp Asn Ile Leu Asp Glu Phe Arg Arg Asn Ala Gly Lys
    1100                1105                1110 ctt ttt cat cta aag ccc aca tca gat gat att gta tat agt aaa            3384
Leu Phe His Leu Lys Pro Thr Ser Asp Asp Ile Val Tyr Ser Lys
    1115                1120                1125 ata gaa aaa act gaa cct gaa gat gtg ggt cca gtt caa gct gga            3429
Ile Glu Lys Thr Glu Pro Glu Asp Val Gly Pro Val Gln Ala Gly
    1130                1135                1140 gat gag caa tca ctg cca tct gtg aca ttg gtt agg aag cac ttc            3474
Asp Glu Gln Ser Leu Pro Ser Val Thr Leu Val Arg Lys His Phe
    1145                1150                1155 agc ggc aag tac acc ata tca gct gaa gaa ttt acc aat gaa atg            3519
Ser Gly Lys Tyr Thr Ile Ser Ala Glu Glu Phe Thr Asn Glu Met
    1160                1165                1170 gtt ggt gct aaa tca cgg aat atc tca ttt cta aaa gga aag gtt            3564
Val Gly Ala Lys Ser Arg Asn Ile Ser Phe Leu Lys Gly Lys Val
    1175                1180                1185 cct tca tgg gtg ggc att ccc aca tca gtc gct cta cca ttt gga            3609
Pro Ser Trp Val Gly Ile Pro Thr Ser Val Ala Leu Pro Phe Gly
    1190                1195                1200 gtt ttt gaa gaa gtt ctg tca aat gac ata aac aag gaa att gcc            3654
Val Phe Glu Glu Val Leu Ser Asn Asp Ile Asn Lys Glu Ile Ala
    1205                1210                1215 agc cag ctg cag tta ctg aaa gag aag ttg gct atc gga gaa ttc            3699
Ser Gln Leu Gln Leu Leu Lys Glu Lys Leu Ala Ile Gly Glu Phe
    1220                1225                1230 aat gca ctt ctc gac ata aga aag atg atc ttg cag cta gca tct            3744
Asn Ala Leu Leu Asp Ile Arg Lys Met Ile Leu Gln Leu Ala Ser
    1235                1240                1245 cca att gag ttg gta caa gag cta aag gga aaa atg cag gca tca            3789
Pro Ile Glu Leu Val Gln Glu Leu Lys Gly Lys Met Gln Ala Ser
    1250                1255                1260
```

```
gga atg cca tgg cct ggt gat gag ggt gaa gat cgg tgg gaa ctt    3834
Gly Met Pro Trp Pro Gly Asp Glu Gly Glu Asp Arg Trp Glu Leu
    1265                1270                1275 gct tgg atg gca ata aaa aga gtt tgg gct tca aag tgg aat gag    3879
Ala Trp Met Ala Ile Lys Arg Val Trp Ala Ser Lys Trp Asn Glu
1280                1285                1290 aga gca tat ttc agc aca agg aaa gtc aag ttg gat cat gac tat    3924
Arg Ala Tyr Phe Ser Thr Arg Lys Val Lys Leu Asp His Asp Tyr
    1295                1300                1305 ttg tgc atg gct gtc ttg gtt caa gaa atc att agt gct gat tat    3969
Leu Cys Met Ala Val Leu Val Gln Glu Ile Ile Ser Ala Asp Tyr
1310                1315                1320 gca ttt gtc atc cac act aca aac cca tca tct gga gac tca tct    4014
Ala Phe Val Ile His Thr Thr Asn Pro Ser Ser Gly Asp Ser Ser
    1325                1330                1335 gaa ata tat gcc gag gtg gtg aaa gga ctc gga gaa act ctt gtt    4059
Glu Ile Tyr Ala Glu Val Val Lys Gly Leu Gly Glu Thr Leu Val
1340                1345                1350 gga gcc tat cca ggc cgg gca ttg agc ttc gtc tgt aat aag aac    4104
Gly Ala Tyr Pro Gly Arg Ala Leu Ser Phe Val Cys Asn Lys Asn
    1355                1360                1365 aat ctg aac tcg cca aag gta ctt ggt ttc cca agc aag cct att    4149
Asn Leu Asn Ser Pro Lys Val Leu Gly Phe Pro Ser Lys Pro Ile
1370                1375                1380 ggc ctc ttc atc aaa cga tca att atc ttc aga tct gat tct aat    4194
Gly Leu Phe Ile Lys Arg Ser Ile Ile Phe Arg Ser Asp Ser Asn
    1385                1390                1395 ggt gaa gat tta gaa ggt tat gca ggt gct ggt ctt tat gac agt    4239
Gly Glu Asp Leu Glu Gly Tyr Ala Gly Ala Gly Leu Tyr Asp Ser
1400                1405                1410 gtg ccc atg gat gag gaa gag aaa gtg gta ctc gac tat gta gct    4284
Val Pro Met Asp Glu Glu Glu Lys Val Val Leu Asp Tyr Val Ala
    1415                1420                1425 gac ccg tta atc atg gat aag aac ttc cgt aat tca ctg ctc tcc    4329
Asp Pro Leu Ile Met Asp Lys Asn Phe Arg Asn Ser Leu Leu Ser
1430                1435                1440 agc att gct cga gca ggt tat gcg atc gag gag ctc tat ggc tct    4374
Ser Ile Ala Arg Ala Gly Tyr Ala Ile Glu Glu Leu Tyr Gly Ser
    1445                1450                1455 cca cag gac att gaa ggt gtt gta aag gat ggt aaa atc ttc gtc    4419
Pro Gln Asp Ile Glu Gly Val Val Lys Asp Gly Lys Ile Phe Val
1460                1465                1470 gtc caa aca aga cca cag atg tga                                4443
Val Gln Thr Arg Pro Gln Met
    1475                1480

<210> SEQ ID NO 4
<211> LENGTH: 1480
<212> TYPE: PRT
<213> ORGANISM: Curcuma longa

<400> SEQUENCE: 4

Met Asn Asn Cys Val Gly His Thr Leu Pro Gln Gln Ala Leu Phe Arg
1               5                   10                  15

Pro Ser Val Val Glu Arg His Asn Thr Ala Cys Gln Arg Ser Ser Gly
            20                  25                  30

Asn Ile Leu Cys Thr Val Pro Ser Ala Ser Lys Ala Glu Asp Val Pro
        35                  40                  45

Ser Leu Lys Pro Phe Leu Ser Ser Arg Phe Leu Gly Lys Thr Pro Tyr
    50                  55                  60
```

```
Ala Gly Lys Gly Asn Pro Leu Lys Lys Asn Leu Arg Thr Val Thr Met
 65                  70                  75                  80

Ser Pro Gln Ala Leu Leu Ala Ala Asp Pro Ala Ser Glu Leu Ala Arg
             85                  90                  95

Lys Phe Lys Leu Asp Thr Asn Ser Glu Leu Glu Val Thr Ile Cys Lys
            100                 105                 110

Pro Thr Ser Glu Ser Pro Met Gln Ile Asp Phe Gln Val Thr Asn Val
            115                 120                 125

Ser Gly Ser Leu Val Leu His Trp Gly Val Ile Leu Gln Thr Arg Arg
130                 135                 140

Glu Trp Ser Leu Pro Ser His Tyr Pro Glu Gly Thr Lys Val Tyr Lys
145                 150                 155                 160

Asn Gln Ala Leu Arg Thr Pro Phe Thr Lys Val Gly Ser Thr Cys Ser
                165                 170                 175

Leu Arg Leu Glu Ile Asp Asp Pro Glu Ile Glu Ile Val Glu Phe Leu
            180                 185                 190

Ile Leu Asp Glu Ala Glu Asn Lys Trp Tyr Lys His Asn Gly Gln Asn
            195                 200                 205

Phe Gln Val His Leu Leu Lys Gln Gly Tyr Gln Asn Gln His Val Ser
210                 215                 220

Val Ser Gly Asn Pro Asn Ile Ile Val Pro Glu Asp Leu Val Gln Ile
225                 230                 235                 240

Gln Ala Phe Leu Arg Trp Glu Arg Lys Gly Arg Gln Thr Tyr Thr Pro
                245                 250                 255

Asp Gln Glu Lys Glu Glu Tyr Glu Ala Ala Arg Met Glu Leu Ile Glu
            260                 265                 270

Glu Ile Ser Arg Gly Met Pro Val Glu Leu Arg Ser Lys Leu Thr
            275                 280                 285

Glu Lys Pro Glu Val Lys Ser Gly Ser Arg Glu Glu Lys Thr His Arg
            290                 295                 300

Val Gln Ser His Lys Gly Gly Ile Ser Asp Asp Leu Val Gln Ile Gln
305                 310                 315                 320

Ala Phe Ile Arg Trp Glu Lys Ala Gly Lys Pro Asn Tyr Pro Pro Glu
                325                 330                 335

Lys Gln Leu Met Glu Phe Glu Glu Ala Arg Lys Glu Leu Gln Leu Glu
            340                 345                 350

Phe Asp Lys Gly Thr Ser Leu Ala Glu Leu Arg Glu Lys Ile Met Lys
            355                 360                 365

Gly Asp Ile Ser Thr Lys Val Leu Lys Gln Leu Lys Val Glu Lys Tyr
            370                 375                 380

Phe Ser Asn Lys Arg Ile Gln Arg Lys Glu Arg Asp Ile Met Glu Ile
385                 390                 395                 400

Leu Asn Lys Lys Val Ala Glu Thr Leu Asp Glu Lys Ser Ser Gln Ile
                405                 410                 415

Val Thr Pro Pro Thr Val Leu Glu Leu Leu Ala Lys Ser Ile His Glu
            420                 425                 430

Gln Asp Gly Glu Ser Val Leu His Gln Lys Ile Tyr Lys Leu Asp Asn
            435                 440                 445

Lys Asn Leu Leu Val Leu Val Thr Lys Pro Phe Glu Arg Thr Lys Val
            450                 455                 460

Tyr Leu Ala Thr Asp Gln Ser Glu Pro Leu Ile Leu His Trp Gly Leu
465                 470                 475                 480

Ser Arg Lys Ser Arg Glu Trp Met Val Pro Pro Thr Ser Ser Ile Pro
```

```
            485                 490                 495
Pro Gly Ser Val Leu Glu Glu Ser Cys Glu Thr Pro Phe Thr Lys
            500                 505                 510

Gly Leu Met Val Asp Gln Tyr Tyr Gln Ala Ile Gln Ile Glu Ile Asp
            515                 520                 525

Gly Gly Asp Tyr Ala Gly Ile Pro Phe Val Leu Arg Ser Asp Asp Lys
            530                 535                 540

Trp Ile Lys Asn Ser Gly Leu Asp Phe Tyr Ile Glu Leu Asp Asp Arg
545                 550                 555                 560

Ser Ile Arg Lys Ala Pro Gly Asp Gly Ser Gly Ile Ala Lys Ser Leu
                565                 570                 575

Leu Asp Lys Ile Ala Asp Leu Glu Thr Glu Ala Gln Lys Ser Phe Met
                580                 585                 590

His Arg Phe Ser Ile Ala Ala Asp Leu Thr Glu Gln Ala Arg Gly Ser
                595                 600                 605

Gly His Leu Gly Leu Val Gly Ile Leu Val Trp Met Arg Phe Met Ala
            610                 615                 620

Met Arg Gln Leu Ile Trp Asn Lys Asn Tyr Asn Val Lys Pro Arg Glu
625                 630                 635                 640

Ile Ser Lys Ala Gln Asp Arg Leu Thr Asp Leu Leu Gln Asp Ile Tyr
                645                 650                 655

Lys Asp Phe Pro Gln Tyr Arg Glu Ile Leu Arg Met Ile Met Ala Thr
                660                 665                 670

Val Gly Arg Gly Gly Glu Gly Asp Val Gly Gln Arg Ile Arg Asp Glu
            675                 680                 685

Ile Leu Val Ile Gln Arg Asn Asn Asp Cys Lys Gly Gly Met Met Glu
            690                 695                 700

Glu Trp His Gln Lys Leu His Asn Asn Thr Ser Pro Asp Asp Val Val
705                 710                 715                 720

Ile Cys Gln Ala Leu Ile Asp Tyr Val Lys Ser Asp Phe Asp Ile Ser
                725                 730                 735

Val Tyr Trp Asp Ser Leu Asn Lys Asn Gly Ile Thr Lys Glu Arg Leu
            740                 745                 750

Leu Ser Tyr Asp Arg Ala Ile His Ser Glu Pro Ser Phe Arg Arg Asp
            755                 760                 765

Gln Lys Glu Gly Leu Leu Arg Asp Leu Gly Asn Tyr Met Arg Thr Leu
            770                 775                 780

Lys Ala Val His Ser Gly Ala Asp Leu Glu Ser Ala Ile Ala Thr Cys
785                 790                 795                 800

Met Gly Tyr Lys Ser Glu Arg Gln Gly Phe Met Val Gly Val Gln Ile
                805                 810                 815

Asn Pro Ile Gly Gly Leu Pro Ser Gly Phe Pro Gly Leu Met Lys Phe
                820                 825                 830

Ile Leu Lys His Val Glu Asp Lys Asn Val Pro Leu Ile Glu Gly Gly
                835                 840                 845

Leu Leu Glu Ala Arg Val Glu Leu Arg Pro Leu Leu Leu Ser Ser His
            850                 855                 860

Glu Arg Leu Lys Asp Leu Ile Phe Leu Asp Ile Ala Leu Asp Ser Thr
865                 870                 875                 880

Val Arg Thr Ala Val Glu Arg Gly Tyr Glu Glu Leu Ser Asn Ala Glu
                885                 890                 895

Pro Glu Lys Leu Ile Tyr Leu Ile Met Leu Leu Leu Glu Asn Leu Ala
                900                 905                 910
```

```
Leu Ser Thr Asp Asp Asn Glu Asp Leu Ile Tyr Cys Leu Lys Gly Trp
        915                 920                 925

Lys His Ser Met Glu Met Cys Lys Gln Lys Asp Asp Gln Trp Ala Leu
    930                 935                 940

Phe Ala Lys Ser Phe Leu Asp Arg Thr Arg Leu Ala Leu Ser Ser Lys
945                 950                 955                 960

Ala Glu Tyr Tyr His Gln Ile Leu Gln Pro Ser Ala Glu Tyr Leu Gly
                965                 970                 975

Ser Leu Leu Asp Val Asp Ala Gly Ala Val Ser Ile Phe Thr Glu Glu
            980                 985                 990

Ile Ile Arg Ala Gly Ser Ala Ala Ser Leu Ser Ala Leu Leu Gln Arg
        995                 1000                1005

Leu Asp Pro Leu Leu Arg Lys Val Ala His Leu Gly Ser Trp Gln
    1010            1015                1020

Val Ile Ser Pro Val Glu Val Ala Gly Tyr Val Glu Ile Val Glu
    1025            1030                1035

Glu Leu Leu Ala Val Gln Asn Lys Ser Tyr Thr Gln Ser Thr Ile
    1040            1045                1050

Leu Val Ala Lys His Val Arg Gly Glu Glu Ile Pro Asp Gly
    1055            1060                1065

Thr Val Ala Val Leu Thr Pro Asp Met Pro Asp Val Leu Ser His
    1070            1075                1080

Val Ser Val Arg Ala Arg Asn Ser Lys Val Cys Phe Ala Thr Cys
    1085            1090                1095

Phe Asp Asp Asn Ile Leu Asp Glu Phe Arg Arg Asn Ala Gly Lys
    1100            1105                1110

Leu Phe His Leu Lys Pro Thr Ser Asp Asp Ile Val Tyr Ser Lys
    1115            1120                1125

Ile Glu Lys Thr Glu Pro Glu Asp Val Gly Pro Val Gln Ala Gly
    1130            1135                1140

Asp Glu Gln Ser Leu Pro Ser Val Thr Leu Val Arg Lys His Phe
    1145            1150                1155

Ser Gly Lys Tyr Thr Ile Ser Ala Glu Glu Phe Thr Asn Glu Met
    1160            1165                1170

Val Gly Ala Lys Ser Arg Asn Ile Ser Phe Leu Lys Gly Lys Val
    1175            1180                1185

Pro Ser Trp Val Gly Ile Pro Thr Ser Val Ala Leu Pro Phe Gly
    1190            1195                1200

Val Phe Glu Glu Val Leu Ser Asn Asp Ile Asn Lys Glu Ile Ala
    1205            1210                1215

Ser Gln Leu Gln Leu Leu Lys Glu Lys Leu Ala Ile Gly Glu Phe
    1220            1225                1230

Asn Ala Leu Leu Asp Ile Arg Lys Met Ile Leu Gln Leu Ala Ser
    1235            1240                1245

Pro Ile Glu Leu Val Gln Glu Leu Lys Gly Lys Met Gln Ala Ser
    1250            1255                1260

Gly Met Pro Trp Pro Gly Asp Glu Gly Glu Asp Arg Trp Glu Leu
    1265            1270                1275

Ala Trp Met Ala Ile Lys Arg Val Trp Ala Ser Lys Trp Asn Glu
    1280            1285                1290

Arg Ala Tyr Phe Ser Thr Arg Lys Val Lys Leu Asp His Asp Tyr
    1295            1300                1305

Leu Cys Met Ala Val Leu Val Gln Glu Ile Ile Ser Ala Asp Tyr
    1310            1315                1320
```

| | | | | | | | | | | |
|---|---|---|---|---|---|---|---|---|---|---|
|Ala|Phe|Val|Ile|His|Thr|Thr|Asn|Pro|Ser|Ser|Gly|Asp|Ser|Ser|
| |1325| | | | |1330| | | |1335| | | | |
|Glu|Ile|Tyr|Ala|Glu|Val|Val|Lys|Gly|Leu|Gly|Glu|Thr|Leu|Val|
| |1340| | | | |1345| | | |1350| | | | |
|Gly|Ala|Tyr|Pro|Gly|Arg|Ala|Leu|Ser|Phe|Val|Cys|Asn|Lys|Asn|
| |1355| | | | |1360| | | |1365| | | | |
|Asn|Leu|Asn|Ser|Pro|Lys|Val|Leu|Gly|Phe|Pro|Ser|Lys|Pro|Ile|
| |1370| | | | |1375| | | |1380| | | | |
|Gly|Leu|Phe|Ile|Lys|Arg|Ser|Ile|Ile|Phe|Arg|Ser|Asp|Ser|Asn|
| |1385| | | | |1390| | | |1395| | | | |
|Gly|Glu|Asp|Leu|Glu|Gly|Tyr|Ala|Gly|Ala|Gly|Leu|Tyr|Asp|Ser|
| |1400| | | | |1405| | | |1410| | | | |
|Val|Pro|Met|Asp|Glu|Glu|Glu|Lys|Val|Val|Leu|Asp|Tyr|Val|Ala|
| |1415| | | | |1420| | | |1425| | | | |
|Asp|Pro|Leu|Ile|Met|Asp|Lys|Asn|Phe|Arg|Asn|Ser|Leu|Leu|Ser|
| |1430| | | | |1435| | | |1440| | | | |
|Ser|Ile|Ala|Arg|Ala|Gly|Tyr|Ala|Ile|Glu|Glu|Leu|Tyr|Gly|Ser|
| |1445| | | | |1450| | | |1455| | | | |
|Pro|Gln|Asp|Ile|Glu|Gly|Val|Val|Lys|Asp|Gly|Lys|Ile|Phe|Val|
| |1460| | | | |1465| | | |1470| | | | |
|Val|Gln|Thr|Arg|Pro|Gln|Met| | | | | | | | |
| |1475| | | | |1480| | | | | | | | |

<210> SEQ ID NO 5
<211> LENGTH: 2400
<212> TYPE: DNA
<213> ORGANISM: Zea mays

<400> SEQUENCE: 5

```
atggcgttcc gggtttctgg ggcggtgctc ggtggggccg taagggctcc ccgactcacc      60
ggcggcgggg agggtagtct agtcttccgg cacaccggcc tcttcttaac tcggggtgct     120
cgagttggat gttcggggac gcacggggcc atgcgcgcgg cggccgcggc caggaaagcg     180
gtcatggttc ctgagggcga gaatgatggc ctcgcatcaa gggctgactc ggctcaattc     240
cagtcggatg aactggaggt accagacatt tctgaagaga caacgtgcgg tgctggtgtg     300
gctgatgctc aagccttgaa cagagttcga gtggtccccc caccaagcga tggacaaaaa     360
atattccaga ttgaccccat gttgcaaggc tataagtacc atcttgagta cggtacagc      420
ctctatagaa gaatccgttc agacattgat gaacatgaag gaggcttgga agccttctcc     480
cgtagttatg agaagtttgg atttaatcgc agcgcggaag gtatcacata tcgagaatgg     540
gctcctggag cattttctgc agcattggtg ggtgacttca acaactggga tccaaatgca     600
gatcgtatga gcaaaaatga gtttggtgtt tgggaaattt ttctgcctaa caatgcagat     660
ggtacatcac ctattcctca tggatctcgt gtaaaggtga aatggatac tccatcaggg     720
ataaaggatt caattccagc ctggatcaag tactcagtgc aggccccagg agaaatacca     780
tatgatggga tttattatga tcctcctgaa gaggtaaagt atgtgttcag gcatgcgcaa     840
cctaaacgac caaaatcatt gcggatatat gaaacacatg tcggaatgag tagcccggaa     900
ccgaagataa acacatatgt aaactttagg gatgaagtcc tcccaagaat aaaaaaactt     960
ggatacaatg cagtgcaaat aatggcaatc caagagcact catattatgg aagctttgga    1020
taccatgtaa ctaatttttt tgcgccaagt agtcgttttg gtaccccaga gaattgaag    1080
tctttgattg atagagcaca tgagcttggt ttgctagttc tcatggatgt ggttcatagt    1140
```

-continued

```
catgcgtcaa gtaatactct ggatgggttg aatggttttg atggtacaga tacacattac    1200
tttcacagtg gtccacgtgg ccatcactgg atgtgggatt ctcgcctatt taactatggg    1260
aactgggaag ttttaagatt tcttctctcc aatgctagat ggtggctcga ggaatataag    1320
tttgatggtt ccgttttga tggtgtgacc tccatgatgt acactcatca cggattacaa     1380
gtaacattta cggggaactt caatgagtat tttggctttg ccaccgatgt agatgcagtg    1440
gtttacttga tgctggtaaa tgatctaatt catggactt t atcctgaggc tgtaaccatt    1500
ggtgaagatg ttagtggaat gcctacattt gcccttcctg ttcacgatgg tggggtaggt    1560
tttgactatc ggatgcatat ggctgtggct gacaaatgga ttgaccttct caagcaaagt    1620
gatgaaactt ggaagatggg tgatattgtg cacacactga caaataggag gtggttagag    1680
aagtgtgtaa cttatgctga aagtcatgat caagcattag tcggcgacaa gactattgcg    1740
ttttggttga tggacaagga tatgtatgat ttcatggccc tcgatagacc ttcaactcct    1800
accattgatc gtgggatagc attacataag atgattagac ttatcacaat gggtttagga    1860
ggagagggct atcttaattt catgggaaat gagtttggac atcctgaatg gatagatttt    1920
ccaagaggtc cgcaaagact tccaagtggt aagtttattc cagggaataa caacagttat    1980
gacaaatgtc gtcgaagatt tgacctgggt gatgcagact atcttaggta tcatggtatg    2040
caagagtttg atcaggcaat gcaacatctt gagcaaaaat atgaattcat gacatctgat    2100
caccagtata tttcccggaa acatgaggag gataaggtga ttgtgttcga aagggagat    2160 ttggtatttg tgttcaactt ccactgcaac aacagctatt ttgactaccg tattggttgt    2220
cgaaagcctg gggtgtataa ggtggtcttg gactccgacg ctggactatt tggtggattt    2280
agcaggatcc atcacgcagc cgagcacttc accgccgact gttcgcatga taataggcca    2340
tattcattct cggtttatac accaagcaga acatgtgtcg tctatgctcc agtggagtga    2400
```

<210> SEQ ID NO 6
<211> LENGTH: 799
<212> TYPE: PRT
<213> ORGANISM: Zea mays

<400> SEQUENCE: 6

```
Met Ala Phe Arg Val Ser Gly Ala Val Leu Gly Gly Ala Val Arg Ala
1               5                   10                  15

Pro Arg Leu Thr Gly Gly Gly Glu Gly Ser Leu Val Phe Arg His Thr
            20                  25                  30

Gly Leu Phe Leu Thr Arg Gly Ala Arg Val Gly Cys Ser Gly Thr His
        35                  40                  45

Gly Ala Met Arg Ala Ala Ala Ala Arg Lys Ala Val Met Val Pro
    50                  55                  60

Glu Gly Glu Asn Asp Gly Leu Ala Ser Arg Ala Asp Ser Ala Gln Phe
65                  70                  75                  80

Gln Ser Asp Glu Leu Glu Val Pro Asp Ile Ser Glu Glu Thr Thr Cys
                85                  90                  95

Gly Ala Gly Val Ala Asp Ala Gln Ala Leu Asn Arg Val Arg Val Val
            100                 105                 110

Pro Pro Pro Ser Asp Gly Gln Lys Ile Phe Gln Ile Asp Pro Met Leu
        115                 120                 125

Gln Gly Tyr Lys Tyr His Leu Glu Tyr Arg Tyr Ser Leu Tyr Arg Arg
    130                 135                 140

Ile Arg Ser Asp Ile Asp Glu His Glu Gly Gly Leu Glu Ala Phe Ser
145                 150                 155                 160
```

-continued

Arg Ser Tyr Glu Lys Phe Gly Phe Asn Arg Ser Ala Glu Gly Ile Thr
                165                 170                 175

Tyr Arg Glu Trp Ala Pro Gly Ala Phe Ser Ala Ala Leu Val Gly Asp
            180                 185                 190

Phe Asn Asn Trp Asp Pro Asn Ala Asp Arg Met Ser Lys Asn Glu Phe
        195                 200                 205

Gly Val Trp Glu Ile Phe Leu Pro Asn Asn Ala Asp Gly Thr Ser Pro
    210                 215                 220

Ile Pro His Gly Ser Arg Val Lys Val Arg Met Asp Thr Pro Ser Gly
225                 230                 235                 240

Ile Lys Asp Ser Ile Pro Ala Trp Ile Lys Tyr Ser Val Gln Ala Pro
                245                 250                 255

Gly Glu Ile Pro Tyr Asp Gly Ile Tyr Tyr Asp Pro Pro Glu Glu Val
            260                 265                 270

Lys Tyr Val Phe Arg His Ala Gln Pro Lys Arg Pro Lys Ser Leu Arg
        275                 280                 285

Ile Tyr Glu Thr His Val Gly Met Ser Ser Pro Glu Pro Lys Ile Asn
    290                 295                 300

Thr Tyr Val Asn Phe Arg Asp Glu Val Leu Pro Arg Ile Lys Lys Leu
305                 310                 315                 320

Gly Tyr Asn Ala Val Gln Ile Met Ala Ile Gln Glu His Ser Tyr Tyr
                325                 330                 335

Gly Ser Phe Gly Tyr His Val Thr Asn Phe Phe Ala Pro Ser Ser Arg
            340                 345                 350

Phe Gly Thr Pro Glu Glu Leu Lys Ser Leu Ile Asp Arg Ala His Glu
        355                 360                 365

Leu Gly Leu Leu Val Leu Met Asp Val Val His Ser His Ala Ser Ser
    370                 375                 380

Asn Thr Leu Asp Gly Leu Asn Gly Phe Asp Gly Thr Asp Thr His Tyr
385                 390                 395                 400

Phe His Ser Gly Pro Arg Gly His His Trp Met Trp Asp Ser Arg Leu
                405                 410                 415

Phe Asn Tyr Gly Asn Trp Glu Val Leu Arg Phe Leu Leu Ser Asn Ala
            420                 425                 430

Arg Trp Trp Leu Glu Glu Tyr Lys Phe Asp Gly Phe Arg Phe Asp Gly
        435                 440                 445

Val Thr Ser Met Met Tyr Thr His His Gly Leu Gln Val Thr Phe Thr
    450                 455                 460

Gly Asn Phe Asn Glu Tyr Phe Gly Phe Ala Thr Asp Val Asp Ala Val
465                 470                 475                 480

Val Tyr Leu Met Leu Val Asn Asp Leu Ile His Gly Leu Tyr Pro Glu
                485                 490                 495

Ala Val Thr Ile Gly Glu Asp Val Ser Gly Met Pro Thr Phe Ala Leu
            500                 505                 510

Pro Val His Asp Gly Gly Val Gly Phe Asp Tyr Arg Met His Met Ala
        515                 520                 525

Val Ala Asp Lys Trp Ile Asp Leu Leu Lys Gln Ser Asp Glu Thr Trp
    530                 535                 540

Lys Met Gly Asp Ile Val His Thr Leu Thr Asn Arg Arg Trp Leu Glu
545                 550                 555                 560

Lys Cys Val Thr Tyr Ala Glu Ser His Asp Gln Ala Leu Val Gly Asp
                565                 570                 575

Lys Thr Ile Ala Phe Trp Leu Met Asp Lys Asp Met Tyr Asp Phe Met
            580                 585                 590

```
Ala Leu Asp Arg Pro Ser Thr Pro Thr Ile Asp Arg Gly Ile Ala Leu
            595                 600                 605

His Lys Met Ile Arg Leu Ile Thr Met Gly Leu Gly Gly Glu Gly Tyr
        610                 615                 620

Leu Asn Phe Met Gly Asn Glu Phe Gly His Pro Glu Trp Ile Asp Phe
625                 630                 635                 640

Pro Arg Gly Pro Gln Arg Leu Pro Ser Gly Lys Phe Ile Pro Gly Asn
                645                 650                 655

Asn Asn Ser Tyr Asp Lys Cys Arg Arg Phe Asp Leu Gly Asp Ala
            660                 665                 670

Asp Tyr Leu Arg Tyr His Gly Met Gln Glu Phe Asp Gln Ala Met Gln
        675                 680                 685

His Leu Glu Gln Lys Tyr Glu Phe Met Thr Ser Asp His Gln Tyr Ile
        690                 695                 700

Ser Arg Lys His Glu Glu Asp Lys Val Ile Val Phe Glu Lys Gly Asp
705                 710                 715                 720

Leu Val Phe Val Phe Asn Phe His Cys Asn Asn Ser Tyr Phe Asp Tyr
                725                 730                 735

Arg Ile Gly Cys Arg Lys Pro Gly Val Tyr Lys Val Val Leu Asp Ser
            740                 745                 750

Asp Ala Gly Leu Phe Gly Gly Phe Ser Arg Ile His His Ala Ala Glu
        755                 760                 765

His Phe Thr Ala Asp Cys Ser His Asp Asn Arg Pro Tyr Ser Phe Ser
        770                 775                 780

Val Tyr Thr Pro Ser Arg Thr Cys Val Val Tyr Ala Pro Val Glu
785                 790                 795

<210> SEQ ID NO 7
<211> LENGTH: 2310
<212> TYPE: DNA
<213> ORGANISM: Triticum aestivum

<400> SEQUENCE: 7
gggatggcga cgttcgcggt gtccggcgcg accctcggtg tggcgcggcc gccggcggcg      60
gcgcaacctg aagaattaca gatacctgaa gacatcgagg agcaaacggc tgaagtaaac     120
atgacagggg ggactgcaga aaaacttgaa tcttcagaac cgactcaagg cattgtggaa     180
acaatcactg atggtgtaac caaaggagtt aaggaactag tcgtggggga gaaaccgcga     240
gttgtcccaa aaccaggaga tgggcagaaa atatacgaga ttgacccaac gctgaaagat     300
tttcggagcc atcttgacta ccgatacagc gaatacagga gaattcgtgc tgctattgac     360
caacatgaag gtggattgga agcattttct cgtggttatg aaaagcttgg atttacccgc     420
agtgctgaag gtatcactta ccgagaatgg gctcctggag cgcattctgc agcattagta     480
ggtgacttca acaattggaa tccgaatgca gatactatga ccagagatga ttatggtgtt     540
tgggagattt tcctccctaa caatgctgat ggatcccag ctattcctca tggctcacgt      600
gtaaagatac ggatggatac tccatctggt gtgaaggatt caatttctgc ttggatcaag     660
ttctctgtgc aggctccagg tgaaatacca ttcaatggca tatattatga tccacctgaa     720
gaggagaagt atgtcttcca acatcctcaa cctaaacgac cagagtcact gaggatttat     780
gaatcacaca ttggaatgag cagcccagaa ccgaagataa attcatatgc taattttagg     840
gatgaggtgc tgccaagaat taaaaggctt ggatacaatg cagtgcagat aatggcaatc     900
caggagcatt catactatgc gagctttggg taccatgtta ctaatttttt tgcaccaagt     960
```

-continued

```
agccgttttg gaactccaga ggacttaaaa tccctgatcg atagagcaca tgagcttggt    1020
ttgcttgttc ttatggatat tgttcatagt cattcatcaa ataatacccct tgacggcttg   1080 aatggtttcg atggcactga tacacattac ttccacggtg gtccacgtgg ccatcattgg    1140
atgtgggatt ctcgtctatt caactatggg agttgggaag tattgagatt cttactgtca    1200
aacgcgagat ggtggcttga agaatataag tttgatggat ttcgatttga tggggtgacc    1260
tccatgatgt atactcacca tggattacaa atgacattta ctgggaacta tggcgagtat    1320
tttggatttg ctactgatgt tgatgcggta gtttacttga tgctggtcaa cgatctaatt    1380
catggacttc atcctgatgc tgtatccatt ggtgaagatg tcagtggaat gcccacatt    1440 tgcatccctg ttccagatgg tggtgttggt tttgactatc gcttgcatat ggctgtagca    1500
gataaatgga ttgaactcct caagcaaagt gacgaatctt ggaaaatggg tgatattgtg    1560
cacaccctaa caaatagaag gtggcttgag aagtgtgtaa cttatgcaga aagtcatgat    1620
caagcactag ttggtgacaa gactattgca ttctggttga tggataagga tatgtatgat    1680
ttcatggctc tggataggcc ttcaactcct cgcattgatc gtggcatagc attacataaa    1740
atgatcaggc ttgtcaccat gggtttaggt ggtgaaggct atcttaactt catgggaaat    1800
gagtttgggc atcctgaatg gatagatttt ccaagaggtc cgcaaactct tccaaccggc    1860
aaagttctcc ctggaaataa caatagttat gataaatgcc gccgtagatt tgatcttgga    1920
gatgcagatt ttcttagata tcatggtatg caagagttcg atcaggcaat gcagcatctt    1980
gaggaaaaat atgggtttat gacatctgag caccagtatg tttcacggaa acatgaggaa    2040
gataaggtga tcatcttcga aagaggagat ttggtatttg ttttcaactt ccactggagc    2100
aatagctttt ttgactaccg tgttgggtgt tccaggcctg ggaagtacaa ggtggcctta    2160
gactccgacg atgcactctt tggtggattc agcaggcttg atcatgatgt cgactacttc    2220
acaaccgaac atccgcatga caacaggccg cgctctttct cggtgtacac tccgagcaga    2280
actgcggtcg tgtatgccct tacagagtaa                                    2310
```

<210> SEQ ID NO 8
<211> LENGTH: 769
<212> TYPE: PRT
<213> ORGANISM: Triticum aestivum

<400> SEQUENCE: 8

Gly Met Ala Thr Phe Ala Val Ser Gly Ala Thr Leu Gly Val Ala Arg
1               5                   10                  15

Pro Pro Ala Ala Ala Gln Pro Glu Glu Leu Gln Ile Pro Glu Asp Ile
            20                  25                  30

Glu Glu Gln Thr Ala Glu Val Asn Met Thr Gly Gly Thr Ala Glu Lys
        35                  40                  45

Leu Glu Ser Ser Glu Pro Thr Gln Gly Ile Val Glu Thr Ile Thr Asp
    50                  55                  60

Gly Val Thr Lys Gly Val Lys Glu Leu Val Val Gly Glu Lys Pro Arg
65                  70                  75                  80

Val Val Pro Lys Pro Gly Asp Gly Gln Lys Ile Tyr Glu Ile Asp Pro
                85                  90                  95

Thr Leu Lys Asp Phe Arg Ser His Leu Asp Tyr Arg Tyr Ser Glu Tyr
            100                 105                 110

Arg Arg Ile Arg Ala Ala Ile Asp Gln His Glu Gly Gly Leu Glu Ala
        115                 120                 125

Phe Ser Arg Gly Tyr Glu Lys Leu Gly Phe Thr Arg Ser Ala Glu Gly
    130                 135                 140

-continued

Ile Thr Tyr Arg Glu Trp Ala Pro Gly Ala His Ser Ala Ala Leu Val
145                 150                 155                 160

Gly Asp Phe Asn Asn Trp Asn Pro Asn Ala Asp Thr Met Thr Arg Asp
                165                 170                 175

Asp Tyr Gly Val Trp Glu Ile Phe Leu Pro Asn Asn Ala Asp Gly Ser
            180                 185                 190

Pro Ala Ile Pro His Gly Ser Arg Val Lys Ile Arg Met Asp Thr Pro
        195                 200                 205

Ser Gly Val Lys Asp Ser Ile Ser Ala Trp Ile Lys Phe Ser Val Gln
    210                 215                 220

Ala Pro Gly Glu Ile Pro Phe Asn Gly Ile Tyr Tyr Asp Pro Pro Glu
225                 230                 235                 240

Glu Glu Lys Tyr Val Phe Gln His Pro Gln Pro Lys Arg Pro Glu Ser
                245                 250                 255

Leu Arg Ile Tyr Glu Ser His Ile Gly Met Ser Ser Pro Glu Pro Lys
            260                 265                 270

Ile Asn Ser Tyr Ala Asn Phe Arg Asp Glu Val Leu Pro Arg Ile Lys
        275                 280                 285

Arg Leu Gly Tyr Asn Ala Val Gln Ile Met Ala Ile Gln Glu His Ser
    290                 295                 300

Tyr Tyr Ala Ser Phe Gly Tyr His Val Thr Asn Phe Phe Ala Pro Ser
305                 310                 315                 320

Ser Arg Phe Gly Thr Pro Glu Asp Leu Lys Ser Leu Ile Asp Arg Ala
                325                 330                 335

His Glu Leu Gly Leu Leu Val Leu Met Asp Ile Val His Ser His Ser
            340                 345                 350

Ser Asn Asn Thr Leu Asp Gly Leu Asn Gly Phe Asp Gly Thr Asp Thr
        355                 360                 365

His Tyr Phe His Gly Gly Pro Arg Gly His His Trp Met Trp Asp Ser
    370                 375                 380

Arg Leu Phe Asn Tyr Gly Ser Trp Glu Val Leu Arg Phe Leu Leu Ser
385                 390                 395                 400

Asn Ala Arg Trp Trp Leu Glu Glu Tyr Lys Phe Asp Gly Phe Arg Phe
                405                 410                 415

Asp Gly Val Thr Ser Met Met Tyr Thr His His Gly Leu Gln Met Thr
            420                 425                 430

Phe Thr Gly Asn Tyr Gly Glu Tyr Phe Gly Phe Ala Thr Asp Val Asp
        435                 440                 445

Ala Val Val Tyr Leu Met Leu Val Asn Asp Leu Ile His Gly Leu His
    450                 455                 460

Pro Asp Ala Val Ser Ile Gly Glu Asp Val Ser Gly Met Pro Thr Phe
465                 470                 475                 480

Cys Ile Pro Val Pro Asp Gly Gly Val Gly Phe Asp Tyr Arg Leu His
                485                 490                 495

Met Ala Val Ala Asp Lys Trp Ile Glu Leu Leu Lys Gln Ser Asp Glu
            500                 505                 510

Ser Trp Lys Met Gly Asp Ile Val His Thr Leu Thr Asn Arg Arg Trp
        515                 520                 525

Leu Glu Lys Cys Val Thr Tyr Ala Glu Ser His Asp Gln Ala Leu Val
    530                 535                 540

Gly Asp Lys Thr Ile Ala Phe Trp Leu Met Asp Lys Asp Met Tyr Asp
545                 550                 555                 560

Phe Met Ala Leu Asp Arg Pro Ser Thr Pro Arg Ile Asp Arg Gly Ile

```
                565             570             575
Ala Leu His Lys Met Ile Arg Leu Val Thr Met Gly Leu Gly Gly Glu
                580             585             590
Gly Tyr Leu Asn Phe Met Gly Asn Glu Phe Gly His Pro Glu Trp Ile
                595             600             605
Asp Phe Pro Arg Gly Pro Gln Thr Leu Pro Thr Gly Lys Val Leu Pro
                610             615             620
Gly Asn Asn Asn Ser Tyr Asp Lys Cys Arg Arg Phe Asp Leu Gly
625             630             635             640
Asp Ala Asp Phe Leu Arg Tyr His Gly Met Gln Glu Phe Asp Gln Ala
                645             650             655
Met Gln His Leu Glu Glu Lys Tyr Gly Phe Met Thr Ser Glu His Gln
                660             665             670
Tyr Val Ser Arg Lys His Glu Glu Asp Lys Val Ile Ile Phe Glu Arg
                675             680             685
Gly Asp Leu Val Phe Val Phe Asn Phe His Trp Ser Asn Ser Phe Phe
                690             695             700
Asp Tyr Arg Val Gly Cys Ser Arg Pro Gly Lys Tyr Lys Val Ala Leu
705             710             715             720
Asp Ser Asp Asp Ala Leu Phe Gly Gly Phe Ser Arg Leu Asp His Asp
                725             730             735
Val Asp Tyr Phe Thr Thr Glu His Pro His Asp Asn Arg Pro Arg Ser
                740             745             750
Phe Ser Val Tyr Thr Pro Ser Arg Thr Ala Val Val Tyr Ala Leu Thr
                755             760             765
Glu

<210> SEQ ID NO 9
<211> LENGTH: 2511
<212> TYPE: DNA
<213> ORGANISM: Triticum aestivum

<400> SEQUENCE: 9
atggctgcgc cggcattcgc agtttccgcg gcggggctgg cccggccgtc ggctcctcga      60
tccggcgggg cagagcggag ggggcgcggg gtggagctgc agtcgccatc gctgctcttc     120
ggccgcaaca agggcacccg ttcaccccgt gccgtcggcg tcggaggttc tggatggcgc     180
gtggtcatgc gcgcgggggg gccgtccggg gaggtgatga tccctgacgg cggtagtggc     240
ggaacaccgc cttccatcga cggtcccgtt cagttcgatt ctgatgatct gaaggttcca     300
ttcattgatg atgaaacaag cctacaggat ggaggtgaag atagtatttg gtcttcagag     360
acaaatcagg ttagtgaaga aattgatgct gaagacacga gcagaatgga caaagaatca     420
tctacgaggg agaaattacg cattctgcca ccaccgggaa atggacagca atatacgag      480 attgacccaa cgctccgaga ctttaagtac catcttgagt atcgatatag cctatacagg     540
agaatacgtt cagacattga tgaacacgaa ggaggcatgg atgtattttc ccgcggttac     600
gagaagtttg gatttatgcg cagcgctgaa ggtatcactt accgagaatg ggctcctgga     660
gcagattctg cagcattagt tggcgacttc aacaattggg atccaaatgc agaccatatg     720
agcaaaaatg accttggtgt ttgggagatt tttctgccaa caatgcaga tggttcgcca     780 ccaattcctc acggctcacg ggtgaaggtg cgaatgggta ctccatctgg gacaaaggat     840
tcaattcctg cttggatcaa gtactccgtg cagactccag gagatatacc atacaatgga     900
atatattatg atcctcccga agaggagaag tatgtattca agcatcctca acctaaacga     960
```

-continued

```
ccaaaatcat tgcggatata tgaaacacat gttggcatga gtagcccgga accaaagatc    1020
aacacatatg caaacttcag ggatgaggtg cttccaagaa ttaaaagact tggatacaat    1080
gcagtgcaaa taatggcaat ccaagagcac tcatactatg gaagctttgg gtaccatgtt    1140
accaatttct ttgcaccaag tagccgtttt gggtccccag aagatttaaa atctttgatt    1200
gatagagctc acgagcttgg cttggttgtc ctcatggatg ttgttcacag tcacgcgtca    1260
aataatacct tggacgggtt gaatggtttt gatggcacgg atacacatta cttccatggc    1320
ggttcacggg gccatcactg gatgtgggat tcccgtgtgt ttaactatgg gaataaggaa    1380
gttataaggt ttctactttc caatgcaaga tggtggctag aggagtataa gtttgatggt    1440
ttccgattcg atggcgcgac ctccatgatg tatacccatc atggattaca agtaaccttt    1500
acaggaagct accatgaata ttttggcttt gccactgatg tagatgcggt cgtttacttg    1560
atgctgatga atgatctaat tcatgggttt tatcctgaag ccgtaactat cggtgaagat    1620
gttagtggaa tgcctacatt tgcccttcct gttcaagttg gtggggttgg ttttgactat    1680
cgcttacata tggctgttgc ccgcaaatgg attgaacttc tcaaaggaaa cgatgaagct    1740
tgggagatgg gtaatattgt gcacacacta acaaacagaa ggtggctgga aaagtgtgtt    1800
acttatgctg aaagtcacga tcaagcactt gttggagaca agactattgc attctggttg    1860
atggacaagg atatgtatga tttcatggcg ctgaacggac cttcgacgcc taatattgat    1920
cgtggaatag cactgcataa aatgattaga cttatcacaa tgggtctagg aggagagggt    1980
tatcttaact ttatgggaaa tgagttcggg catcctgaat ggatagactt ccaagaggc    2040 ccacaagtac ttccaagtgg taagttcatc ccaggaaaca acaacagtta cgacaaatgc    2100
cgtcgaagat ttgacctggg tgatgcagaa tttcttaggt atcatggtat gcagcagttt    2160
gatcaggcaa tgcagcatct tgaggaaaaa tatggtttta tgacatcaga ccaccagtac    2220
gtatctcgga aacatgagga agataaggtg atcgtgtttg aaaaggggga cttggtattt    2280
gtgttcaact tccactggag tagtagctat ttcgactacc gggtcggctg ttttaaagcct    2340 gggaagtaca aggtggtctt agactcggac gctggactct ttggtggatt tggtaggatc    2400
catcacactg cagagcactt cacttctgac tgccaacatg acaacaggcc ccattcattc    2460
tcagtgtaca ctcctagcag aacctgtgtt gtctatgctc caatgaacta a    2511
```

<210> SEQ ID NO 10
<211> LENGTH: 836
<212> TYPE: PRT
<213> ORGANISM: Triticum aestivum

<400> SEQUENCE: 10

```
Met Ala Ala Pro Ala Phe Ala Val Ser Ala Gly Leu Ala Arg Pro
1               5                   10                  15

Ser Ala Pro Arg Ser Gly Gly Ala Glu Arg Arg Gly Arg Val Glu
            20                  25                  30

Leu Gln Ser Pro Ser Leu Leu Phe Gly Arg Asn Lys Gly Thr Arg Ser
        35                  40                  45

Pro Arg Ala Val Gly Val Gly Gly Ser Gly Trp Arg Val Val Met Arg
    50                  55                  60

Ala Gly Gly Pro Ser Gly Glu Val Met Ile Pro Asp Gly Gly Ser Gly
65                  70                  75                  80

Gly Thr Pro Pro Ser Ile Asp Gly Pro Val Gln Phe Asp Ser Asp
                85                  90                  95

Leu Lys Val Pro Phe Ile Asp Asp Glu Thr Ser Leu Gln Asp Gly Gly
            100                 105                 110
```

```
Glu Asp Ser Ile Trp Ser Ser Glu Thr Asn Gln Val Ser Glu Glu Ile
        115                 120                 125
Asp Ala Glu Asp Thr Ser Arg Met Asp Lys Glu Ser Ser Thr Arg Glu
    130                 135                 140
Lys Leu Arg Ile Leu Pro Pro Gly Asn Gly Gln Gln Ile Tyr Glu
145                 150                 155                 160
Ile Asp Pro Thr Leu Arg Asp Phe Lys Tyr His Leu Glu Tyr Arg Tyr
                165                 170                 175
Ser Leu Tyr Arg Arg Ile Arg Ser Asp Ile Asp Glu His Glu Gly Gly
            180                 185                 190
Met Asp Val Phe Ser Arg Gly Tyr Glu Lys Phe Gly Phe Met Arg Ser
        195                 200                 205
Ala Glu Gly Ile Thr Tyr Arg Glu Trp Ala Pro Gly Ala Asp Ser Ala
    210                 215                 220
Ala Leu Val Gly Asp Phe Asn Asn Trp Asp Pro Asn Ala Asp His Met
225                 230                 235                 240
Ser Lys Asn Asp Leu Gly Val Trp Glu Ile Phe Leu Pro Asn Asn Ala
                245                 250                 255
Asp Gly Ser Pro Pro Ile Pro His Gly Ser Arg Val Lys Val Arg Met
            260                 265                 270
Gly Thr Pro Ser Gly Thr Lys Asp Ser Ile Pro Ala Trp Ile Lys Tyr
        275                 280                 285
Ser Val Gln Thr Pro Gly Asp Ile Pro Tyr Asn Gly Ile Tyr Tyr Asp
    290                 295                 300
Pro Pro Glu Glu Glu Lys Tyr Val Phe Lys His Pro Gln Pro Lys Arg
305                 310                 315                 320
Pro Lys Ser Leu Arg Ile Tyr Glu Thr His Val Gly Met Ser Ser Pro
                325                 330                 335
Glu Pro Lys Ile Asn Thr Tyr Ala Asn Phe Arg Asp Glu Val Leu Pro
            340                 345                 350
Arg Ile Lys Arg Leu Gly Tyr Asn Ala Val Gln Ile Met Ala Ile Gln
        355                 360                 365
Glu His Ser Tyr Tyr Gly Ser Phe Gly Tyr His Val Thr Asn Phe Phe
    370                 375                 380
Ala Pro Ser Ser Arg Phe Gly Ser Pro Glu Asp Leu Lys Ser Leu Ile
385                 390                 395                 400
Asp Arg Ala His Glu Leu Gly Leu Val Val Leu Met Asp Val Val His
                405                 410                 415
Ser His Ala Ser Asn Asn Thr Leu Asp Gly Leu Asn Gly Phe Asp Gly
            420                 425                 430
Thr Asp Thr His Tyr Phe His Gly Gly Ser Arg Gly His His Trp Met
        435                 440                 445
Trp Asp Ser Arg Val Phe Asn Tyr Gly Asn Lys Glu Val Ile Arg Phe
    450                 455                 460
Leu Leu Ser Asn Ala Arg Trp Trp Leu Glu Glu Tyr Lys Phe Asp Gly
465                 470                 475                 480
Phe Arg Phe Asp Gly Ala Thr Ser Met Met Tyr Thr His His Gly Leu
                485                 490                 495
Gln Val Thr Phe Thr Gly Ser Tyr His Glu Tyr Phe Gly Phe Ala Thr
            500                 505                 510
Asp Val Asp Ala Val Val Tyr Leu Met Leu Met Asn Asp Leu Ile His
        515                 520                 525
Gly Phe Tyr Pro Glu Ala Val Thr Ile Gly Glu Asp Val Ser Gly Met
```

```
                530            535            540
Pro Thr Phe Ala Leu Pro Val Gln Val Gly Gly Val Gly Phe Asp Tyr
545                 550                 555                 560

Arg Leu His Met Ala Val Ala Arg Lys Trp Ile Glu Leu Leu Lys Gly
                565                 570                 575

Asn Asp Glu Ala Trp Glu Met Gly Asn Ile Val His Thr Leu Thr Asn
            580                 585                 590

Arg Arg Trp Leu Glu Lys Cys Val Thr Tyr Ala Glu Ser His Asp Gln
        595                 600                 605

Ala Leu Val Gly Asp Lys Thr Ile Ala Phe Trp Leu Met Asp Lys Asp
    610                 615                 620

Met Tyr Asp Phe Met Ala Leu Asn Gly Pro Ser Thr Pro Asn Ile Asp
625                 630                 635                 640

Arg Gly Ile Ala Leu His Lys Met Ile Arg Leu Ile Thr Met Gly Leu
                645                 650                 655

Gly Gly Glu Gly Tyr Leu Asn Phe Met Gly Asn Glu Phe Gly His Pro
            660                 665                 670

Glu Trp Ile Asp Phe Pro Arg Gly Pro Gln Val Leu Pro Ser Gly Lys
        675                 680                 685

Phe Ile Pro Gly Asn Asn Asn Ser Tyr Asp Lys Cys Arg Arg Arg Phe
    690                 695                 700

Asp Leu Gly Asp Ala Glu Phe Leu Arg Tyr His Gly Met Gln Gln Phe
705                 710                 715                 720

Asp Gln Ala Met Gln His Leu Glu Glu Lys Tyr Gly Phe Met Thr Ser
                725                 730                 735

Asp His Gln Tyr Val Ser Arg Lys His Glu Glu Asp Lys Val Ile Val
            740                 745                 750

Phe Glu Lys Gly Asp Leu Val Phe Val Phe Asn Phe His Trp Ser Ser
        755                 760                 765

Ser Tyr Phe Asp Tyr Arg Val Gly Cys Leu Lys Pro Gly Lys Tyr Lys
    770                 775                 780

Val Val Leu Asp Ser Asp Ala Gly Leu Phe Gly Gly Phe Gly Arg Ile
785                 790                 795                 800

His His Thr Ala Glu His Phe Thr Ser Asp Cys Gln His Asp Asn Arg
                805                 810                 815

Pro His Ser Phe Ser Val Tyr Thr Pro Ser Arg Thr Cys Val Val Tyr
            820                 825                 830

Ala Pro Met Asn
        835

<210> SEQ ID NO 11
<211> LENGTH: 25
<212> TYPE: DNA
<213> ORGANISM: Artificial Sequence
<220> FEATURE:
<223> OTHER INFORMATION: PCR primer

<400> SEQUENCE: 11
tggataaata caaagagtga agcag                                      25

<210> SEQ ID NO 12
<211> LENGTH: 23
<212> TYPE: DNA
<213> ORGANISM: Artificial Sequence
<220> FEATURE:
<223> OTHER INFORMATION: PCR primer

<400> SEQUENCE: 12
```

-continued

```
ggacattgaa ggtgttgtaa agg                                           23

<210> SEQ ID NO 13
<211> LENGTH: 25
<212> TYPE: DNA
<213> ORGANISM: Artificial Sequence
<220> FEATURE:
<223> OTHER INFORMATION: Taqman Sonde

<400> SEQUENCE: 13
cttcgtcgtc caaacaagac cacag                                         25

<210> SEQ ID NO 14
<211> LENGTH: 19
<212> TYPE: DNA
<213> ORGANISM: Artificial Sequence
<220> FEATURE:
<223> OTHER INFORMATION: PCR Primer

<400> SEQUENCE: 14
gtgggagcaa ctccagctt                                                19

<210> SEQ ID NO 15
<211> LENGTH: 19
<212> TYPE: DNA
<213> ORGANISM: Artificial Sequence
<220> FEATURE:
<223> OTHER INFORMATION: PCR Primer

<400> SEQUENCE: 15
cggtgagggc agagttgtt                                                19

<210> SEQ ID NO 16
<211> LENGTH: 16
<212> TYPE: DNA
<213> ORGANISM: Artificial Sequence
<220> FEATURE:
<223> OTHER INFORMATION: Taqman-Sonde

<400> SEQUENCE: 16
actccggcgc ccccgt                                                   16
```

STARCHES WITH HIGH AMYLOSE CONTENT AND IMPROVED PROCESSING PROPERTIES

CROSS-REFERENCE TO RELATED APPLICATIONS

This application is the U.S. National Stage filing of International Application No. PCT/EP2008/005438, filed Jun. 25, 2008, which claims priority to EP 07075524.4, filed Jun. 25, 2007; U.S. Provisional Patent Application No. 60/937,194, filed Jun. 26, 2007; EP 08075190.2, filed Mar. 12, 2008; U.S. Provisional Patent Application No. 61/069,293, filed Mar. 13, 2008; EP 08075500.2, filed May 15, 2008; and U.S. patent application Ser. No. 61/127,802, filed May 15, 2008, the disclosures of each of which are hereby incorporated by reference.

BACKGROUND OF THE INVENTION (i) Field of the Invention:

The present invention relates to maize starches with an apparent amylose content between 35 wt. % and 90 wt. % and with improved processing properties relative to conventional high-amylose maize starches. Furthermore, the present invention relates to maize meals and foodstuffs containing these maize starches or maize meals. In addition the present invention relates to methods of production of said maize starches/maize meals and maize plants which synthesize these maize starches. Moreover, the present invention relates to wheat starches with an apparent amylose content between 35 wt. % and 90 wt. % and improved processing properties, and wheat meals and foodstuffs containing these wheat starches or wheat meals. In addition, the present invention relates to methods of production of said wheat starches/wheat meals and wheat plants that synthesize these wheat starches.

(ii) Description of the Related Art:

Apart from oils, fats and proteins, polysaccharides are the main renewable raw materials from plants. Along with cellulose, starch occupies a key position among the polysaccharides, and is one of the most important storage substances in higher plants.

Furthermore, from the standpoint of nutritional physiology, starch is an important constituent of the human and animal diet. The structural characteristics of the starch present in foodstuffs can influence the functional (e.g. water binding capacity, swelling power), nutritional-physiological (e.g. digestibility, influence of the foodstuff on the glycemic index) or structure-forming (e.g. resistance to cutting, texture, stickiness, processability) properties of the most varied foodstuffs. Foodstuff compositions therefore often contain a starch with specified structural characteristics, which determine the desired properties of the foodstuff in question. The properties of foodstuffs containing starch-storing plant tissues (e.g. cereals, fruits, meals), can also be influenced by the starch contained in the plant tissues.

The polysaccharide starch is a polymer of chemically uniform basic building blocks, the glucose molecules. However, it is a very complex mixture of various molecular forms, which vary with respect to their degree of polymerization, the presence of branchings of the glucose chains and their chain lengths, and furthermore, may be modified, e.g. phosphorylated. Therefore starch is not a uniform raw material. In particular we distinguish amylose, an essentially unbranched polymer of alpha-1,4-glycosidically linked glucose molecules, from amylopectin, which is a complex mixture of variously branched glucose chains. The branchings arise because of the presence of additional alpha-1,6-glycosidic linkages. In typical plants used for industrial starch production or as foodstuffs, such as maize, rice, wheat or potato, the starch that is synthesized consists of approx. 20%-25% amylose and approx. 70%-75% amylopectin.

Various methods are available for determining amylose content, and they can lead to different numerical values of the amylose content for one and the same starch. Many of these methods are based on the iodine-binding capacity of amylose, which can be determined potentiometrically (Banks & Greenwood, in W. Banks & C. T. Greenwood, Starch and its components (pp. 51-66), Edinburgh, Edinburgh University Press), amperometrically (Larson et al., Analytical Chemistry 25(5), (1953), 802-804) or spectrophotometrically (Morrison & Laignelet, J. Cereal Sc. 1, (1983), 9-20). The amylose content can also be determined calorimetrically by DSC (differential scanning calorimetry) measurements (Kugimiya & Donovan, Journal of Food Science 46, (1981), 765-770; Sievert & Holm, Starch/Starke 45 (4), (1993), 136-139). It is also possible to determine the amylose content using SEC (size exclusion chromatography) chromatography of native or debranched starch. This method was recommended in particular for determining the amylose content of genetically engineered starches (Gérard et al., Carbohydrate Polymers 44, (2001), 19-27).

The functional, nutritional-physiological or structure-forming properties of starch, such as solubility, retrogradation behavior, water-binding capacity, film-forming properties, viscosity, gelatinization properties, freezing/thawing stability, acid resistance, gel strength, swelling power, digestibility, starch granule size of starches are influenced by, among other things, the structural characteristics of the starch, such as the amylose/amylopectin ratio, the molecular weight of the glucose polymers, the pattern of side chain distribution, the phosphate content, the lipid content or the protein content.

Using classical breeding methods, precise alteration of the structural/functional properties of the starch synthesized in plants is very difficult and is only possible for selected structural characteristics. An alternative to breeding methods is the precise modification of starch-producing plants by the methods of genetic engineering. However, a precondition for this is the identification and characterization of the enzymes involved in starch synthesis and/or starch modification and their subsequent functional analysis in transgenic plants.

Maize mutants with an increased amylose content relative to wild-type maize plants are known and are designated as "amylose extenders" or "ae" for short. Amylose extender (ae) maize mutants were described for example in Vineyard and Bear (Maize Genet Coop Newsletter 26: 5 (1952), who describe the reference allele ae1-Ref, and in Moore and Creech (Genetics 70, (1972), 611-619), Garwood et al. (Cereal Chemistry 53(3), (1976), 355-364) and Hedman and Boyer (Biochemical Genetics 21 (11/12), (1983), 1217-1222).

Maize plants (cells) that have an "amylose extender mutation" show a mutation of the gene of the starch branching enzyme IIb from maize (abbreviation "BE IIb" or "SBE IIb"), which is also designated as amylose extender gene. This mutation leads to a decrease in SBE IIb enzyme activity in the endosperm of these maize plants compared to the BE IIb activity in the endosperm of wild-type maize plants. Preferably this mutation of BE IIb in maize plants (cells) has the effect that SBE IIb activity is no longer detectable (e.g. Fisher et al., Plant Physiol. 110, (1996), 611-619, in particular FIG. 4; Hedman and Boyer, Biochemical Genetics 21 (11/12), (1983), 1217-1222, in particular Table 1).

The "amylose extender mutation" is as a rule a recessive mutation of the amylose extender 1 locus.

Amylose extender mutants synthesize a high-amylose maize starch, which has an increased apparent amylose content compared with wild-type maize plants (plant cells), which as a rule is between 45 and 75 wt. %, depending on the genetic background, cultivation conditions and method of amylose determination.

Maize starches with the product designation Amylogel®, Hylon® V and Hylon® VII are available commercially and as a rule have an apparent amylose content of approx. 50% or 70% (Shi et al., Journal of Cereal Science 27, (1998), 289-299).

In contrast to wild-type maize starches, these high-amylose maize starches have a greatly reduced swelling power (Senti and Russell, Tappi Vol. 43 No. 4, (1960), 343-349; Shi et al., Journal of Cereal Science 27, (1998), 289-299).

Aqueous suspensions of the high-amylose maize starches show no development of viscosity in viscosity analysis (e.g. RVA analysis) (Senti and Russell, Tappi Vol. 43 No. 4, (1960), 343-349). Native high-amylose maize starches so far only undergo gelatinization in a very energy-intensive and therefore cost-intensive method in an autoclave at elevated temperature and pressure, or they require subsequent chemical modification.

Based on the aforementioned properties, the high-amylose maize starches are very difficult to process, so that the range of applications in which the advantageous properties of the native high-amylose maize starches (e.g. very good film-forming properties, good gel-forming properties, use as resistant starch with prebiotic action) can be utilized is still very limited. Therefore there is a great demand for high-amylose maize starches with improved processing properties, such as increased solubility in hot water, increased swelling power and capacity for viscosity development in aqueous suspensions under normal conditions. High-amylose wheat starches with good processing properties are also not available.

SUMMARY OF THE INVENTION

Accordingly, one aim of the present invention is to make available high-amylose maize starches, or maize meals that contain these maize starches, which have improved processing properties compared with the known high-amylose maize starches from amylose extender maize mutants, and to make maize plants (cells) available which synthesize said maize starches.

A further aim of the present invention is to make available high-amylose wheat starches, or wheat meals that contain these wheat starches, which have improved processing properties compared with wheat starch or wheat meal from wheat plants with the amylose extender genotype, and to make wheat plants (cells) available which synthesize said wheat starches.

DETAILED DESCRIPTION OF THE INVENTION

Figure 1:
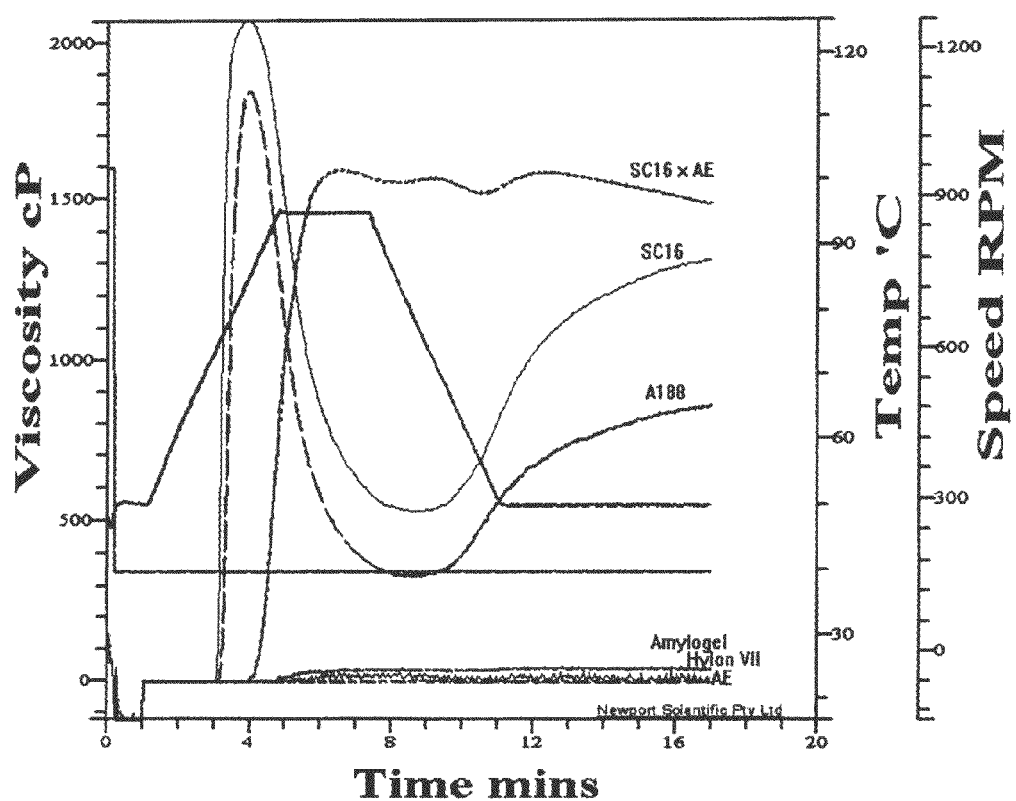
FIG. 1 shows RVA profiles of various maize starches including starch from the crossing of SC16 x ae1 compared with the parent lines.

These aims are achieved by the embodiments presented in the claims.

The present invention therefore relates to a maize starch, which has an apparent amylose content between 35 wt. % and 90 wt. %, between 38 wt. % and 85 wt. %, preferably between 40 wt. % and 80 wt. %, especially preferably between 42 wt. % and 75 wt. % and displays certain viscosity properties in RVA analysis.

In a further embodiment the maize starch according to the invention has an apparent amylose content of at least 35 wt. %, preferably of at least 40 wt. % especially preferably of at least 42 wt. %.

In a further embodiment the maize starch according to the invention has an apparent amylose content between 38 wt. % and 85 wt. %, preferably between 40 wt. % and 80 wt. %, especially preferably between 42 wt. % and 75 wt. %.

In one embodiment of the present invention the maize starch according to the invention displays, in an aqueous suspension in RVA analysis, an increase in viscosity of more than 60 centipoise (cP), preferably more than 100 and especially preferably more than 200 centipoise (cP).

The present invention also relates to a wheat starch that has an apparent amylose content between 35 wt. % and 90 wt. %, between 38 wt. % and 85 wt. %, preferably between 40 wt. % and 80 wt. %, especially preferably between 42 wt. % and 75 wt. % and displays certain viscosity properties in RVA analysis.

In one embodiment of the present invention the wheat starch according to the invention displays, in an aqueous suspension in RVA analysis, an increase in viscosity of more than 60 centipoise (cP), preferably more than 100 and especially preferably more than 200 centipoise (cP).

In a further embodiment the wheat starch according to the invention has an apparent amylose content of at least 35 wt. %, preferably of at least 40 wt. %.

In a further embodiment the wheat starch according to the invention has an apparent amylose content between 38 wt. % and 85 wt. %, preferably between 40 wt. % and 80 wt. %, especially preferably between 42 wt. % and 75 wt. %.

Methods of determination of the amylose content are known by a person skilled in the art. In connection with the present invention, amylose content means the content of apparent amylose as a percentage by weight relative to the amount of starch. The apparent amylose content of a starch/of a meal is determined in connection with the present invention preferably by the method described below (see "General methods, Determination of the content of apparent amylose").

In an especially preferred embodiment, the maize starch according to the invention is a native maize starch.

The term "native maize starch" means, in connection with the present invention, that the maize starch is isolated by methods known by a person skilled in the art from maize plants according to the invention, from starch-storing parts of the maize plants according to the invention or from propagating material according to the invention. After isolation, no additional chemical derivatization (e.g. acetylation, oxidation, crosslinking etc.) takes place for the native maize starches according to the invention.

In an especially preferred embodiment the wheat starch according to the invention is a native wheat starch.

The term "native wheat starch" means, in connection with the present invention, that the wheat starch is isolated by methods known by a person skilled in the art from wheat plants according to the invention, from starch-storing parts of the wheat plants according to the invention or from propagating material according to the invention. After isolation, no additional chemical derivatization (e.g. acetylation, oxidation, crosslinking etc.) takes place for the native wheat starches according to the invention.

The term "RVA analysis" means, in connection with the present invention, that the viscosity properties of the starches (according to the invention) are determined by means of a "Rapid Visco Analyzer" (=RVA). RVA instruments are for example made and marketed by the company Newport Scientific Pty Ltd, Investment Support Group, Warriewood, NSW 2102, Australia. RVA analysis is the standard method of analysis for investigation of the gelatinization properties of starch.

In connection with the present invention, RVA analysis of the starches according to the invention is preferably carried out according to AACC Standard Method No. 61-02, "Determination of the Pasting Properties of Rice with the Rapid Visco Analyzer" (Final Approval Oct. 15, 1997; Reapproval Nov. 3, 1999; Approved Methods of the American Association of Cereal Chemists (AACC)-10th edition—Including 2001, 2002 and 2003 Supplements, American Association of Cereal Chemists (2003), St Paul Minn., USA). Instead of the rice flour samples described in this AACC method, in connection with the present invention the maize or wheat starches according to the invention are analyzed. In connection with the present invention, preferably the temperature and shear profile described in AACC method 61-02 is employed, which is also described later (see "General methods").

In an especially preferred embodiment of the present invention, the changes in the viscosity properties in RVA analysis according to AACC method 61-02 relate to a 10% (w/v) aqueous suspension of the starch according to the invention in water.

Using RVA analysis, various properties can be determined, such as the pasting temperature, the peak viscosity, the final viscosity and the setback.

In a further embodiment, the increase in viscosity of an aqueous suspension of the maize or wheat starch according to the invention in RVA analysis is more than 250 centipoise (cP), preferably more than 500 and especially preferably more than 1000 centipoise (cP) compared to the viscosity in centipoise (cP) at the start of the RVA analysis.

In a further embodiment the increase in viscosity of an aqueous suspension of the maize or wheat starch according to the invention in RVA analysis is between 200 and 2000 centipoise (cP), preferably between 1000 and 1800 centipoise (cP) and especially preferably between 1300 and 1700 centipoise (cP).

In a further embodiment, the maize starch according to the invention displays, in RVA analysis, a measurable pasting temperature, preferably of at least 75° C., preferably of at least 80° C. and especially preferably of at least 85° C.

In a further embodiment the maize starch according to the invention displays, in RVA analysis, a pasting temperature between 78° C. and 95° C., preferably between 80° C. and 93° C. and especially preferably between 82° C. and 91° C.

In contrast to conventional native high-amylose starches, which display little if any gelatinization in RVA analysis under normal pressure, the starches according to the invention have the advantage that despite the increased amylose content they gelatinize under standard conditions. As a result the processability of the starch according to the invention is greatly improved compared with other high-amylose starches. Therefore gelatinization of the starches according to the invention does not require increased temperature or increased pressure, thus leading to energy savings and therefore cost savings.

The term "pasting temperature" (RVA PT=RVA Pasting Temperature) means, in connection with the present invention, that the measured value for the start of viscosity development according to RVA analyses is the temperature at which the viscosity curve during the heating process leaves the baseline and at which, in a time interval of 0.5 min, the viscosity changes by more than 50 centipoise (cP).

In a further embodiment the maize or wheat starches according to the invention have a peak viscosity between 1200 and 2000 centipoise (cP), preferably between 1400 and 1900 centipoise (cP) and especially preferably between 1500 and 1850 centipoise (cP).

In a further embodiment the maize or wheat starches according to the invention have a peak viscosity of at least 1200, preferably of at least 1500 centipoise (cP).

In a further embodiment the maize or wheat starches according to the invention have a peak viscosity of at most 2600, preferably of at most 2500 centipoise (cP).

In contrast to conventional high-amylose maize starches, which do not have a viscosity forming effect, the maize starches according to the invention display, surprisingly, a peak viscosity that is comparable to that of wild-type maize plants or is at least very similar. This applies correspondingly to the wheat starches according to the invention.

The "peak viscosity" in RVA analysis means, in connection with the present invention, the maximum viscosity measured in centipoise (cP), determined after a measurement time of 2 to 8 minutes.

In a further embodiment, the maize or wheat starches according to the invention have a "trough viscosity" of at least 600, preferably at least 750 and especially preferably of at least 1000 centipoise (cP). In this feature, the maize starches according to the invention differed markedly both from conventional high-amylose maize starches, which owing to the lack of viscosity development have no, or at any rate only a very low trough viscosity of less than 150 centipoise (cP), as well as from maize starches of wild-type maize plants, which similarly have a markedly lower trough viscosity of less than 1000 centipoise (cP). The same applies correspondingly to the wheat starches according to the invention.

The "trough viscosity" in RVA analysis means, in connection with the present invention, the minimum viscosity measured in centipoise (cP), which occurs after reaching the peak viscosity and is determined after a measuring time of 6 to 12 minutes, preferably after 7-12 minutes.

In a further embodiment, the maize or wheat starches according to the invention have, in RVA analysis, a final viscosity of more than 1000 centipoise (cP), preferably more than 1150 and especially preferably more than 1350 centipoise (cP).

In a further embodiment, the maize or wheat starches according to the invention have a final viscosity between 1100 and 2000 centipoise (cP), preferably between 1300 and 1800 centipoise (cP) and especially preferably between 1450 and 1700 centipoise (cP).

In a further embodiment the maize or wheat starches according to the invention have a final viscosity of at least 1400, preferably of at least 1500 centipoise (cP).

In a further embodiment the maize or wheat starches according to the invention have a final viscosity of at most 2700, preferably of at most 2500 centipoise (cP).

In a further embodiment the maize or wheat starches according to the invention have a final viscosity between 1400 and 2700 centipoise (cP), and preferably between 1500 and 2500 centipoise (cP).

The "final viscosity" means, in connection with the present invention, the viscosity value in centipoise that occurs at the end of the RVA analysis. According to AACC Method 61-02, the end of RVA analysis is reached after a measuring time of 12.5 minutes.

In a further embodiment, the maize or wheat starches according to the invention have a "breakdown" in RVA analysis between 30 and 500 centipoise (cP), preferably between 40 and 250 centipoise (cP) and especially preferably between 50 and 150 centipoise (cP) and even more especially preferably between 50 and 200. In this respect the maize starches according to the invention differ markedly from wild-type maize starches.

"Breakdown" means, in connection with the present invention, the difference of peak viscosity minus trough viscosity.

In a further embodiment of the present invention, the maize or wheat starches according to the invention have, in RVA analysis, a setback of less than 350 centipoise (cP), preferably of less than 300, preferably of less than 200, in particular less than 150 and especially preferably of less than 100 centipoise (cP).

In a further embodiment, the maize or wheat starches according to the invention have a setback between −100 and 350 centipoise (cP), preferably between 0 and 250 centipoise (cP), especially preferably between 20 and 175 centipoise (cP) and even more especially preferably between 50 and 350.

The term "setback" denotes, in connection with the present invention, the difference of final viscosity minus trough viscosity.

The (maize) starches according to the invention thus not only have the advantage that their aqueous suspensions have stable viscosity over a wide temperature range, but also that the undesirable rethickening of the starch suspensions only occurs to a reduced extent, if at all, compared with wild-type starches.

In a further embodiment the present invention relates to a maize starch which has an apparent amylose content between 35 wt. % and 90 wt. %, between 38 wt. % and 85 wt. %, preferably between 40 wt. % and 80 wt. %, more preferably between 42 wt. % and 75 wt. %, and which displays certain viscosity properties in a Brabender analysis.

A Brabender analysis in connection with the present invention is an analysis of the viscosity properties of the starches (according to the invention) using a Brabender visco-amylograph. Apart from RVA analysis, Brabender analysis is the most common method of determining the viscosity properties of starch suspensions. They differ for example with regard to sample quantity, sample volume, stirring speed and analysis time.

In connection with the present invention, Brabender analysis of the starches according to the invention is preferably carried out according to the method described hereinbelow (Brabender analysis).

In a further embodiment the maize starches according to the invention have, in Brabender analysis, a peak viscosity between 40 and 200 Brabender units (BUs), preferably between 50 and 150 Brabender units (BUs) and more preferably between 60 and 120 Brabender units (BUs).

In a further embodiment the maize starches according to the invention have, in Brabender analysis, a peak viscosity of at least 35, preferably of at least 60 Brabender units (BUs).

In a further embodiment the maize starches according to the invention have, in Brabender analysis, a peak viscosity of at most 200, preferably of at most 150 BUs.

The "peak viscosity" in Brabender analysis means, in connection with the present invention, the maximum viscosity measured in Brabender units (BUs), determined after a measurement time of 10 to 80 minutes.

In a further embodiment the maize starches according to the invention have, in Brabender analysis, a final viscosity between 40 and 180 Brabender units (BUs), preferably between 50 and 150 Brabender units (BUs) and particularly preferably between 55 and 100 Brabender units (BUs).

In a further embodiment the maize starches according to the invention have, in Brabender analysis, a final viscosity of at least 30, preferably of at least 55 Brabender units (BUs).

In a further embodiment the maize starches according to the invention have, in Brabender analysis, a peak viscosity of at most 180, preferably of at most 130 BUs.

The "final viscosity" in Brabender analysis means, in connection with the present invention, the maximum viscosity measured in Brabender units (BUs), determined after a measurement time of 120 minutes.

In a further embodiment the maize starch according to the invention has, in Brabender analysis, a measurable pasting temperature, preferably of at least 80° C., more preferably of at least 84° C. and even more preferably of at least 87° C.

In a further embodiment, the maize starch according to the invention has, in Brabender analysis, a pasting temperature between 85° C. to 97° C., preferably between 86° C. and 95° C. and more preferably between 87° C. and 94° C.

In contrast to conventional native high-amylose starches (for example from ae maize plants, Hylon VII®), which display little if any gelatinization in Brabender analysis under normal pressure, the starches according to the invention have the advantage that despite the increased amylose content they gelatinize under standard conditions. As a result the processability of the starch according to the invention is greatly improved compared with other high-amylose starches. Therefore gelatinization of the starches according to the invention does not require increased temperature or increased pressure, thus leading to energy savings and therefore cost savings.

The term "pasting temperature in Brabender analysis" means, in connection with the present invention, that the measured value for the start of viscosity development according to RVA analyses is the temperature which can be determined by means of the standard software from Brabender GmbH & Co. KG under standard settings, preferably by means of the program Micro Visco Amylograph, WinVis-2.4.7, VisCorr-2.1.2, Univ. Eval.-1.1.2, which is made available by Brabender GmbH & Co. KG.

A further advantage of the starches according to the invention is that during processing in which hot rolls are used they can be applied to the rolls as a suspension. Other maize starches with increased amylose content would only undergo limited gelatinization, if at all, during this processing, and accordingly cannot be applied as paste or film to said rolls. The starches according to the invention are particularly suitable for all applications in which the thickening capacity, the gelling properties or the binding properties of added substances are important. Therefore the starch according to the invention is especially suitable for the production of foodstuffs such as bakery products, instant food, puddings, soups, candy, chocolate, ice cream, panada for fish or meat, frozen desserts or extruded snacks. Furthermore, the starch according to the invention is suitable for the production of adhesives, applications in textile processing, as an addition for building materials, for applications in the area of animal feeding, as an additive for cosmetics and in paper processing.

In particular, use of the starch according to the invention for the production of cold-water-soluble pregelatinized starches is also conceivable. Pregelatinized starches are physically modified starches, which are mainly produced by Wet-Thermal® treatment. In contrast to native starch, with cold water they form dispersions or pastes or gels, depending on the concentration of pregelatinized starch used and on the type of starch used in the production of the pregelatinized starch. Based on these properties, pregelatinized starches have a number of possible applications in the food industry, as well as in many technical areas. The use of pregelatinized starch, which is also known as cold-swelling starch, instead of native starch, has the advantage in various cases that production processes can be simplified and shortened.

For the production, for example, of instant desserts and puddings, pregelatinized starches are required, which after being stirred into a cold liquid, such as water or milk, very quickly form firm gels, for example in the case of a suet pudding. These requirements are not met by the commercial pregelatinized starches from wheat, potato or maize starch. To achieve the abovementioned properties, for the existing commercially available pregelatinized starches it is necessary to include additives in the pregelatinized starch, such as gelatin, alginate, carrageenan (carrageen) and/or inorganic salts. This use of "additives" is not necessary to the same extent e.g. after production of pregelatinized starches with starches according to the invention, isolated from plant cells according to the invention.

Compared with gels produced using conventional high-amylose maize starches, the gels according to the invention have the advantage that their production requires less energy input and no expensive equipment has to be used in order to generate high temperatures/pressures, as the starches according to the invention already undergo gelatinization in water under normal conditions.

In a further embodiment of the present invention the maize starch according to the invention has, after pasting in water, a light transmittance of at least 5, preferably at least 7 and more preferably at least 9. In a further embodiment the maize starch according to the invention has a light transmittance of less than 25, preferably less than 20.

In connection with the present invention, the light transmittance is preferably determined by means of the "Determination of light transmittance" method described below.

The maize starches according to the invention, after suspension and heating, therefore have the advantage that the resulting pastes/gels have an increased light transmittance, i.e. transparency, than pastes/gels prepared by means of high-amylose maize starch from conventional ae maize mutants.

A further advantage of the maize starch according to the invention resides in its increased freeze-thaw stability compared with starch from ae maize mutants.

In a further embodiment of the present invention the maize starches according to the invention have, after one freeze-thaw cycle, a freeze-thaw stability of less than 70% water loss, preferably of less than 65% water loss. In a further embodiment of the present invention the maize starches according to the invention have, after one freeze-thaw cycle, a freeze-thaw stability of more than 40% water loss, preferably of more than 50% water loss.

In a further embodiment of the present invention the maize starches according to the invention have, after one freeze-thaw cycle, a freeze-thaw stability which is elevated compared with maize starch from ae maize mutants. Increasing the freeze-thaw stability preferably means in this connection a reduction in water loss by at least 5%, preferably by at least 10%.

In connection with the present invention the freeze-thaw stability of the starches according to the invention is preferably determined by the "Determination of freeze-thaw stability" method described below.

The swelling power is an important functional property, e.g. in the processing of starches in the food industry.

It is necessary to distinguish between the swelling power of starch in cold water (e.g. room temperature) and the swelling power in warm or hot water.

Native starches have negligible, if any, swelling power in cold water, whereas selected physically modified (pregelatinized, dried) starches can already swell in cold water.

In connection with the present invention, the term "swelling power" relates to the behavior of starch, preferably native starch, in hot aqueous suspensions, preferably at a temperature of 90° C. In connection with the present invention, the swelling power is preferably determined with a 3% (w/v) starch suspension at a temperature of 90° C. by the method of Leach et al. (Cereal Chemistry 36, (1959), 534-544). The swelling power is determined as the quotient of the weight of the gel divided by the difference of the initial weight of the starch sample and the soluble constituents:

Swelling power (g/g)=weight of the gel/(initial weight of starch−soluble constituents)

Commercially available high-amylose maize starch, such as Hylon VII®, has a far lower swelling power, compared with wild-type maize starch. For Hylon VII® starch with an apparent amylose content of approx. 70%, for example, a swelling power of approx. 6 g/g was determined according to the method of Leach et al. (Cereal Chemistry 36, (1959), 534-544), whereas wild-type maize starch exhibits a swelling power of approx. 22 g/g (Shi et al., Journal of Cereal Science 27, (1998), 289-299).

The maize starch according to the invention has, compared with conventional high-amylose maize starches, the advantage of a considerably improved swelling power. In a further embodiment, the maize starch according to the invention has a swelling power of at least 7 g/g, preferably of at least 10 g/g and especially preferably of at least 12 g/g.

In a further embodiment the maize starch according to the invention has a swelling power between 7 g/g and 20 g/g, preferably between 10 g/g and 18 g/g, especially preferably between 11 g/g and 15 g/g, most especially preferably between 11 and 17 g/g.

Owing to the increased swelling power relative to conventional high-amylose maize starches, the maize starches according to the invention are better suited for certain applications. If, for example, starch is used as a thickening agent, the increased swelling power of the starch means that much less starch has to be used to achieve the same thickening effect. This means that for example the calorie content of starch-thickened foodstuffs can be reduced.

In a further embodiment, the maize starches according to the invention have an increased solubility in hot water, relative to native high-amylose maize starches. The solubility in hot water of the maize starches according to the invention is at least 8%, preferably at least 9% and especially preferably at least 11%.

In a further embodiment the maize starches according to the invention have a solubility in hot water between 8% and 25%, preferably between 9% and 20% and especially preferably between 10% and 16%.

In connection with the present invention, the solubility in hot water is preferably determined with a 3% (w/v) starch suspension at 90° C. by the method of Leach et al. (Cereal Chemistry 36, (1959), 534-544), which is also described below ("General methods"). The solubility in hot water is found from the following formula:

Solubility in hot water (%)=weight of dried supernatant/initial weight of starch×100

In a further embodiment, the maize starches according to the invention are characterized in that they have a phosphate content in position C6 between 10 and 40 nmol C6P/mg starch (dry weight), preferably between 12 and 35 nmol C6P/mg starch (dry weight) and especially preferably between 15 and 30 nmol C6P/mg starch (dry weight).

The term "phosphate content in position C6" means, in connection with the present invention, the content of phosphate groups that are bound to carbon atom position "6" of the glucose monomers of the starch. Basically, in starch in vivo, positions C3 and C6 of the glucose units can be phosphorylated. In connection with the present invention, the phosphate content in position C6 (=C-6-P content) is preferably determined through glucose-6-phosphate determination by the optical-enzymatic test described later (modified according to Nielsen et al., 1994, Plant Physiol. 105, 111-117).

In a further embodiment the (native) maize or wheat starch according to the invention has modified digestive properties compared with starches from the corresponding maize or wheat wild-type plants.

"Modified digestive properties" compared with starches from the corresponding maize or wheat wild-type plants is to be understood in connection with the present invention as meaning in particular an increased content of resistant starch (RS content) and/or a reduced fraction of rapidly digestible starch RDS.

The RS content of the preferably native maize or wheat starch according to the invention is comparable to the RS content of corresponding starches from maize or wheat plants which have an amylose extender mutation and do not express a heterologous GWD gene.

In a further embodiment the preferably native maize or wheat starch according to the invention has a content of rapidly digestible starch RDS between 1 wt. % to 20 wt. %, preferably between 2 wt. % to 18 wt. %, more preferably between 3 wt. % to 16 wt. %.

In connection with the present invention the RS and RDS contents are determined and calculated via the method of Englyst et al. (Europ. J. of Clinical Nutrition 46 (Suppl. 2), (1992), S 33-50, see in particular the following sections from Englyst et al., page S35-S36: "Reagents, Apparatus, Spectrophotometer"; page S36-S37, paragraph "Measurement of free glucose (FG)"; page S38, paragraph "Measurement of RDS and SDS"); S39 Measurement of $RS_3$).

Since the RDS content of maize or wheat starches isolated from maize/wheat plants (cells) which express a heterologous GWD gene and have no amylose extender mutation is above that of the corresponding maize/wheat wild-type plants, it is surprising to a person skilled in the art that the RDS content of the maize or wheat starches according to the invention is comparable to the RDS content of maize or wheat starches isolated from maize/wheat plants (cells) having an amylose extender mutation but not expressing a heterologous GWD gene.

A reduced RDS content is also displayed by processing products (for example food products) of the maize or wheat starch according to the invention even when the starch in these products is no longer in the native form.

The reduced RDS content of the maize/wheat starches according to the invention and of the maize/wheat flours according to the invention is of appreciable nutritional advantage. This is because the constant consumption of food products having a high glycemic load, such as, for example, food products containing rapidly digestible starches, and the attendant insulin response are suspected of being a risk factor in the etiology of diseases such as high blood pressure, adipositas, heart diseases and type II diabetes.

The present invention also relates to the maize or wheat starch with one or more of the properties described above, produced by the plant cells according to the invention or the plants according to the invention. That is, this description discloses any combination of the following properties of starches: apparent amylose content, phosphate content in position C6, pasting temperature, peak viscosity, trough viscosity, final viscosity, breakdown, setback, swelling power, solubility in hot water, gel strength, RS content, RDS content, freeze-thaw stability, light transmittance. All combinations of two, three, four, five, six, seven, eight, nine and all properties are to be regarded as disclosed.

A person skilled in the art knows that the properties of starch can be altered by e.g. thermal, chemical, enzymatic or mechanical derivatization. Derivatized starches are particularly suitable for various applications in the food and/or nonfood area. The starches according to the invention are more suitable as starting substance for the production of derivatized starches than conventional high-amylose starches, as they have, e.g. through the higher content of starch phosphate, a higher proportion of reactive functional groups and, moreover, are more easily gelatinized.

The present invention therefore also relates to methods of production of a derivatized maize or wheat starch, in which native maize or wheat starch according to the invention is derivatized subsequently. Furthermore, the present invention also relates to derivatized maize or wheat starch containing the maize or wheat starch according to the invention.

The term "derivatized starch" means, in connection with the present invention, a maize or wheat starch according to the invention, whose properties were altered by means of chemical, enzymatic, thermal or mechanical methods after isolation from the maize or wheat plants (cells) according to the invention or their reproductive material.

In a further embodiment of the present invention, the derivatized maize or wheat starch according to the invention is a heat-treated and/or acid-treated starch.

In a further embodiment, the derivatized maize or wheat starch according to the invention is a starch ether, in particular starch alkyl ether, O-allyl ether, hydroxylalkyl ether, O-carboxylmethyl ether, nitrogen-containing starch ether, phosphate-containing starch ether or sulfur-containing starch ether.

In a further embodiment, the derivatized maize or wheat starches according to the invention are crosslinked starches.

In a further embodiment, the derivatized maize or wheat starches according to the invention are starch graft polymers.

In a further embodiment, the derivatized maize or wheat starches according to the invention are oxidized starches.

In a further embodiment, the derivatized maize or wheat starches according to the invention are starch esters, in particular starch esters that are introduced into the starch using organic acids. Especially preferably, they are so-called phosphate, nitrate, sulfate, xanthate, acetate or citrate starches.

The derivatized maize or wheat starches according to the invention are suitable for various uses in the pharmaceutical industry, and in the food and/or nonfood area. Methods for production of derivatized maize or wheat starches according to the invention are known by a person skilled in the art and are described in the general literature. A review of the production of derivatized starches is given e.g. in Orthoefer (in Corn, Chemistry and Technology, 1987, eds. Watson and Ramstad, Chapter 16, 479-499).

Derivatized starch, obtainable or obtained by the method according to the invention for the production of a derivatized starch, is also an object of the present invention.

In addition, the use of modified starches according to the invention for the production of derivatized starch is an object of the present invention.

The present invention also relates to maize plant (cells) that express a heterologous GWD gene and have an amylose extender mutation.

The present invention also relates to maize plants that contain the maize plant cells according to the invention.

In a preferred embodiment the maize plant (cells) according to the invention synthesize the maize starch according to the invention.

In a further preferred embodiment the maize plants (cells) according to the invention are transgenic maize plants (cells), which contain a transgene that leads to a detectable expression of a heterologous GWD gene.

The present invention further relates to wheat plants (cells) that express a heterologous GWD gene and have an amylose extender mutation. In a preferred embodiment the wheat plants (cells) according to the invention synthesize the wheat starch according to the invention.

The present invention also relates to wheat plants that contain the wheat plant cells according to the invention.

In a further preferred embodiment the wheat plants (cells) according to the invention are transgenic wheat plants (cells), which contain a transgene that leads to a detectable expression of a heterologous GWD gene. In an especially preferred embodiment of the present invention said transgene comprises the entire coding region of a GWD or fragments of said coding region, which are encoding an enzymatically active GWD protein.

In connection with the present invention, a GWD protein means a protein with the enzymatic activity of an alpha-glucan, water dikinase (GWD, E.C.: 2.7.9.4) (Ritte et al., 2002, PNAS 99, 7166-7171), which was often also designated as R1 protein, especially in the earlier scientific literature (e.g. WO9711188, WO9827212, Lorberth et al., Nature Biotechnology 16 (1998), 473-477). In the GWD-catalyzed reaction, the educts of alpha-1,4-glucan or starch, adenosine triphosphate (ATP) and water are converted to the products glucan-phosphate (starch phosphate), monophosphate and adenosine monophosphate (Kötting et al., 2005, Plant Physiol. 137, 2424-252, Ritte et al., 2002, PNAS 99, 7166-7171). In the process, a beta-phosphate residue is transferred from ATP to starch or glucan.

GWD can utilize nonphosphorylated starch as a substrate, i.e. a de novo phosphorylation of nonphosphorylated starch can be catalyzed by GWD (Kotting et al., 2005, Plant Physiol. 137, 2424-252, Baunsgaard et al., 2005, Plant Journal 41, 595-605). GWD can insert phosphate groups in position C6 of the glucose monomers of starch.

It is assumed that during catalysis of the phosphorylation reaction of a starch by a protein with the activity of a glucan water dikinase, a phosphorylated protein is formed as an intermediate, in which the beta-phosphate residue of the ATP is bound covalently to an amino acid of the protein with the activity of a glucan water dikinase (Ritte et al., 2002, PNAS 99, 7166-7171). The intermediate arises through autophosphorylation of the protein with the activity of a glucan water dikinase, i.e. the protein with the activity of a glucan water dikinase itself catalyzes the reaction that leads to the intermediate (Ritte et al., 2002, PNAS 99, 7166-7171).

In potato plants, the GWD (R1) protein is bound to the starch granules of the storage starch in potato tubers (Lorberth et al., 1998, Nature Biotechnology 16, 473-477). Starches isolated from leaves of an *Arabidopsis thaliana* sex1-3 mutant do not have any detectable amounts of covalently-bound phosphate residues, but they are phosphorylated in vitro by a protein with the activity of a glucan water dikinase. That is, nonphosphorylated starch, e.g. isolated from leaves of an *Arabidopsis thaliana* sex1-3 mutant, is utilized as substrate in a phosphorylation reaction catalyzed by a protein with the activity of a glucan water dikinase (Ritte et al., Planta 216, (2003), 798-801).

Amino acid sequences that encode proteins with the activity of a glucan water dikinase contain a phosphohistidine domain. Phosphohistidine domains are for example described in Tien-Shin Yu et al. (2001, Plant Cell 13, 1907-1918). In the autophosphorylation of a protein with the activity of a glucan water dikinase, a histidine residue in the phosphohistidine domain of the amino acid sequence encoding a protein with the activity of a glucan water dikinase is phosphorylated (Mikkelsen et al., 2004, Biochemical Journal 377, 525-532). In the protein sequence of a protein with the activity of a glucan water dikinase from *Solanum tuberosum*, shown as SEQ ID NO 2, for example the amino acids 1064 to 1075 constitute the phosphohistidine domain. If the conserved histidine residue (in the protein sequence shown as SEQ ID NO 2, for example, amino acid 1069) of the phosphohistidine domain is replaced with another amino acid, there is no longer any autophosphorylation and therefore also no phosphorylation of glucans by the mutagenized protein (Mikkelsen et al., 2004, Biochemical Journal 377, 525-532). Furthermore, a protein with the activity of a glucan water dikinase is characterized in that it has a C-terminal nucleotide binding domain, which comprises amino acids 1121 to 1464 in the amino acid sequence shown as an example as SEQ ID NO 2. A deletion of the nucleotide binding domain leads to inactivation of a protein with the activity of a glucan water dikinase (Mikkelsen and Blennow, 2005, Biochemical Journal 385, 355-361).

At the N-terminus, proteins with the activity of a glucan water dikinase have a carbohydrate binding domain, also called carbohydrate binding module (CBM), comprising amino acids 78 to 362 in the amino acid sequence shown as SEQ ID NO 2. Among other things, carbohydrate binding domains are characterized in that their amino acid sequences have conserved tryptophan residues. If these conserved amino acid residues are exchanged for other amino acids, the carbohydrate binding domains can lose their ability to bind glucans. Thus, for example, exchange of amino acids W139 or W194 in the amino acid sequence shown as SEQ ID No. 2 leads to a loss of function of this carbohydrate binding domain. If the carbohydrate binding domain of a glucan water dikinase is deleted (for example a deletion of amino acids 1 to 362 of the amino acid sequence shown as SEQ ID No. 2, with amino acids 1 to 77 representing a plastid signal peptide), this does not, however, lead to inactivation of the phosphorylating activity of the enzyme (Mikkelsen et al., 2006, Biochemistry 45, 4674-4682).

Nucleic acid sequences and their corresponding amino acid sequences, encoding a protein with the activity of a glucan water dikinase have been described from various species, such as potato (WO9711188, GenBank Acc.: AY027522.1, Y09533.1), wheat (WO0077229, U.S. Pat. No. 6,462,256, GenBank Acc.: AAN93923.1, GenBank Acc.: AR236165.1), rice (GenBank Acc.: AAR61445.1, U.S. Pat. No. 6,620,987, GenBank Acc.: AR400814.1), maize (GenBank Acc.: AAR61444.1, GenBank Acc.: AR400813.1; WO9827212), soybean (GenBank Acc.: AAR61446.1, GenBank Acc.: AR400815.1), *Curcuma longa* (SEQ ID NOs 3 and 4), citrus (GenBank Acc.: AY094062.1), *Arabidopsis* (GenBank Acc.: AF312027.1), the green alga *Ostreococcus tauri* (GenBank Acc.: AY570720.1) and from *Chlamydomonas reinhardtii* (US 60/701,693, WO2007/018770). A synthetic GWD nucleotide sequence optimized for expression in maize was described under SEQ ID No. 1 in WO2005/002359 (corresponds to US2006/0282917 A1).

It is preferable, in connection with the present invention, to use nucleic acid molecules that comprise the entire coding region of a GWD. Said nucleic acid sequences and amino acid sequences encoding a protein with the activity of a glucan water dikinase are published inter alia by the NCBI (http://www.ncbi.nlm.nih.gov/entrez/) and by naming the references are expressly incorporated in the description of the present application.

In connection with the present invention, apart from the GWD genes enumerated here, it is also possible to use GWD genes from other organisms or synthetic GWD genes. Preferably the GWD gene is derived from Solanum tuberosum or Curcuma longa and has sequence identity of at least 50%, in particular at least 60%, preferably at least 70%, especially preferably of at least 80% and quite especially preferably of at least 90% to the coding region of the nucleic acid molecules given as SEQ ID No. 1 (Solanum tuberosum) or as SEQ ID No. 3 (Curcuma longa). Moreover, the coding region of the nucleotide sequence given as SEQ ID No. 1 is preferred, and the coding region of the nucleotide sequence given as SEQ ID No. 3 is especially preferred.

In a preferred embodiment, in connection with the maize or wheat plants (cells) according to the invention, a GWD of the genus Curcuma or Solanum, preferably of the species Curcuma longa or Solanum tuberosum, is used.

The GWD with the amino acid sequence given as SEQ ID No. 2 is preferred, and the GWD with the amino acid sequence given as SEQ ID No. 4 is especially preferred.

The term "identity" means, in connection with the present invention, the number of coinciding amino acids/nucleotides (identity) with other proteins/nucleic acids, expressed as a percentage. The identity of a protein, for example with the activity of a GWD, is preferably determined by comparison with the amino acid sequence given as SEQ ID NO 2 or SEQ ID No. 4 or the identity of a nucleic acid molecule encoding a protein with the activity of a GWD is determined by comparison with the coding nucleic acid sequence given as SEQ ID No. 1 or SEQ ID No. 3 with other proteins/nucleic acids using computer programs. If sequences that are being compared with one another have different lengths, the identity is to be determined so that the number of amino acids/nucleotides which the shorter sequence has in common with the longer sequence, determines the percentage identity. Preferably the identity is determined using the well-known, publicly available computer program ClustalW (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from various websites, including IGBMC (Institut de Génétique et de Biologie Molèculaire et Cellulaire, B.P.163, 67404 Illkirch Cedex, France; ftp://ftp-igbmc.use-strasbg.fr/pub/) and EBI (ftp://ftp.ebi.ac.uk/pub/software/) and from all reflected websites of the EBI (European Bioinformatics Institute, Wellcome Trust Genome Campus, Hinxton, Cambridge CB10 1SD, UK).

It is preferable to use the ClustalW computer program of Version 1.8, for determining the identity between proteins described within the scope of the present invention and other proteins. The following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

It is preferable to use the ClustalW computer program of Version 1.8, for determining the identity between e.g. the nucleotide sequence of the nucleic acid molecules described within the scope of the present invention and the nucleotide sequence of other nucleic acid molecules. The following parameters are to be set: KTUPLE=2, TOPDIAGS=4, PAIRGAP=5, DNAMATRIX:IUB, GAPOPEN=10, GAPEXT=5, MAXDIV=40, TRANSITIONS: unweighted.

A "heterologous" GWD gene or protein means, in connection with the present invention, a GWD that does not occur naturally in the maize or wheat plant (cell), but whose coding DNA sequence is inserted in the cell, for example by methods of genetic engineering, such as transformation of the cell. Then the coding DNA sequence of the heterologous GWD can for example be derived from a different maize variety than the transformed maize plant cell or respectively from a different wheat variety than the transformed wheat plant cell. It is preferably not under the control of its own promoter, but under the control of a promoter that is heterologous with respect to the particular GWD gene. Preferably the heterologous GWD is derived from a different plant species than the transformed maize plant cell/maize plant or wheat plant cell/wheat plant according to the invention or the GWD used is under the control of a heterologous promoter, i.e. of a promoter that does not correspond to the natural GWD promoter of the particular GWD. Especially preferably, the coding DNA sequence of the heterologous GWD is derived from a different plant genus than the transformed maize plant cell/maize plant or than the transformed wheat plant cell/wheat plant.

The term "plant genus" means, in connection with the present invention, a hierarchic stage of the system of biological classification. A genus contains one or more species. An example of a genus is Triticum L. (wheat). All species within a genus always have a two-part (binomial) name, which in addition to the genus designation also includes a specific epithet. Triticum aestivum L. (bread wheat) is accordingly a species of the genus Triticum.

The term "maize plants (cells) that have an amylose extender mutation" means, in connection with the present invention, maize plants (cells) that have a mutation of the gene of the starch branching enzyme IIb from maize (abbreviated to "BE IIb" or "SBE IIb"), also called amylose extender gene, and this mutation leads to a decrease in SBE IIb enzyme activity in the endosperm of these maize plants compared to the BE IIb activity in the endosperm of wild-type maize plants.

Preferably this mutation of BE IIb in maize plants (cells) has the effect that no SBE IIb activity is detectable any longer (e.g. Fisher et al., Plant Physiol. 110, (1996), 611-619, in particular FIG. 4; Hedman and Boyer, Biochemical Genetics 21 (11/12), (1983), 1217-1222, in particular Table 1).

BE IIb protein from maize means, in connection with the present invention, a branching enzyme of the isoform IIb that is encoded by the so-called amylose extender gene (Kim et al., Plant Molecular Biology 38, (1998), 945-956). The branching enzyme (BE) of the isoform IIb ($\alpha$-1,4-glucan: $\alpha$-1,4-glucan 6-glycosyltransferase; E.C. 2.4.1.18) catalyzes a transglycosylation reaction, in which $\alpha$-1,4-linkages of an $\alpha$-1,4-glucan donor are hydrolyzed and the $\alpha$-1,4-glucan chains thus released are transferred to an $\alpha$-1,4-glucan acceptor chain and thus converted to $\alpha$-1,6-linkages.

In its biochemical properties, the BEIIb protein from maize differs markedly from the BEI protein from maize, presented by Fisher et al. (Plant Physiol. 110, (1996), 611-619) in Table 1, page 612. For example, the BEI protein amylose branches more quickly than the BEIIb protein, whereas the BEIIb protein amylopectin branches at a higher rate than the BEI protein does (Guan and Preiss, Plant Physiol. 102, (1993), 1269-1273). The amino acid sequence of the BEIIb protein differs from the BEIIa protein according to Gao et al. (Plant Physiol. 114, (1997), 69-78) mainly by a 49 amino acid long N-terminal extension of the BEIIa protein. The molecular weight of the BEIIa protein determined by SDS-PAGE is 89 kD, and that of the BEIIb protein is somewhat less, namely 85 kDa (Fisher et al., Plant Physiol. 110, (1996), 611-619).

The amino acid sequence of the BEIIb protein from maize has identity of at least 85%, preferably of at least 90%, of at least 95% and especially preferably of at least 98% with the amino acid sequence shown as SEQ ID NO 6.

An "amylose extender" gene (also "BEIIb" gene) from maize means, in connection with the present invention, a gene that encodes a BEIIb protein. The nucleic acid sequence of the amylose extender gene from maize has identity of at least 85%, preferably of at least 90%, of at least 95% and especially preferably of at least 98% with the nucleic acid sequence shown as SEQ ID No. 5.

In a further embodiment of the present invention, the "amylose extender mutation" of the maize plant (cell) according to the invention is a dominant mutation of the amylose extender 1 locus, which leads to the synthesis of a maize starch that has an increased apparent amylose content compared with wild-type maize plants (cells), which is between 35 and 90 wt. %, in particular between 38-85 wt. %, preferably 40-80 wt. % and especially preferably between 42-75 wt. %.

Preferably, the dominant mutation is the mu-induced allele Ae1-5180 of the amylose extender 1 locus (Stinard et al., Plant Cell 5, (1993), 1555-1566).

In an especially preferred embodiment of the present invention, the "amylose extender mutation" of the maize plant (cell) according to the invention is a maize plant (cell) that has a homozygously recessive "amylose extender" genotype and synthesizes a maize starch that has an apparent amylose content between 38-85 wt. %, preferably between 40-80 wt. % and especially preferably between 42-75 wt. %. The amylose extender 1 (ae1) locus includes the structural gene that encodes the SBE IIb protein (Hedman and Boyer, Biochemical Genetics 20 (5/6), (1982), 483-492).

Amylose extender (ae) maize mutants were described for example in Vineyard and Bear (Maize Genet Coop Newsletter 26: 5 (1952), who describe the reference allele ae1-Ref, and in Moore and Creech (Genetics 70, (1972), 611-619), Garwood et al. (Cereal Chemistry 53(3), (1976), 355-364) and Hedman and Boyer (Biochemical Genetics 21 (11/12), (1983), 1217-1222).

The term "wheat plants (cells) that have an amylose extender mutation" means, in connection with the present invention, wheat plants (cells) that have a mutation of the gene of the starch-branching enzyme IIa or of the starch-branching enzyme IIa (BE IIa protein) and of the starch-branching enzyme IIb (BE-IIb protein) from wheat (abbreviations "BE IIa", "BE IIb", "SBE IIa" or "SBE IIb"), where this mutation leads to a decrease in BE IIa enzyme activity or these mutations lead to a decrease in BE IIa and BE IIb enzyme activity in the endosperm of these wheat plants compared to the BE IIa activity or to the BEIIa and to the BE IIb activity in the endosperm of wild-type wheat plants and to the synthesis of a wheat starch with an apparent amylose content between 38-85 wt. %, preferably between 40-80 wt. % and especially preferably between 42-75 wt. %.

BE IIa protein from wheat means, in connection with the present invention, a branching enzyme of the isoform IIa from wheat (Rahman et al., Plant Physiology 125, (2001), 1314-1324), that is encoded by a BE IIa gene from wheat. The branching enzyme (BE) of the isoform IIb ($\alpha$-1,4-glucan: $\alpha$-1,4-glucan 6-glycosyltransferase; E.C. 2.4.1.18) catalyzes a transglycosylation reaction, in which $\alpha$-1,4-linkages of an $\alpha$-1,4-glucan donor are hydrolyzed and the $\alpha$-1,4-glucan chains released thereby are transferred to an $\alpha$-1,4-glucan acceptor chain and thereby converted to $\alpha$-1,6-linkages.

The amino acid sequence of the BEIIa protein from wheat has identity of at least 85%, preferably of at least 90%, of at least 95% and especially preferably of at least 98% with the amino acid sequence shown as SEQ ID NO 8.

A "BE IIa gene from wheat" means, in connection with the present invention, a gene that encodes a BEIIa protein from wheat. The nucleic acid sequence of the BE IIa gene from wheat has identity of at least 85%, preferably of at least 90%, of at least 95% and especially preferably of at least 98% with the nucleic acid sequence shown as SEQ ID No. 7.

The BE IIb protein from wheat means, in connection with the present invention, a branching enzyme of the isoform IIb from wheat (Regina et al., Planta 222 (5), (2005), 899-909) that is encoded by a BE IIb gene from wheat. The branching enzyme (BE) of the isoform IIb ($\alpha$-1,4-glucan: $\alpha$-1,4-glucan 6-glycosyltransferase; E.C. 2.4.1.18) catalyzes a transglycosylation reaction, in which $\alpha$-1,4-linkages of an $\alpha$-1,4-glucan donor are hydrolyzed and the $\alpha$-1,4-glucan chains released thereby are transferred to an $\alpha$-1,4-glucan acceptor chain and are converted thereby to $\alpha$-1,6-linkages.

The amino acid sequence of the BEIIb protein from wheat has identity of at least 85%, preferably of at least 90%, of at least 95% and especially preferably of at least 99% with the amino acid sequence shown as SEQ ID NO 10.

A "BE IIb gene from wheat" means, in connection with the present invention, a gene that encodes a BEIIb protein from wheat. The nucleic acid sequence of the BE IIb gene from wheat has identity of at least 85%, preferably of at least 90%, of at least 95% and especially preferably of at least 98% with the nucleic acid sequence shown as SEQ ID NO 9.

In a further embodiment of the present invention, the maize or wheat plant (cell) according to the invention, which synthesizes the maize starch or wheat starch according to the invention, is genetically modified, wherein the genetic modification with reference to maize leads to a detectable expression of the heterologous GWD and to a decrease in activity of the BEIIb protein or with reference to wheat leads to a detectable expression of the heterologous GWD and to a decrease in BE IIa enzyme activity or the BE IIa and the BE IIb enzyme activity compared with corresponding wild-type maize plants (cells) that are not genetically modified or compared with corresponding wild-type wheat plants (cells) that are not genetically modified.

The genetic modification can be any genetic modification that leads, with reference to maize, to a detectable expression of the heterologous GWD and to a decrease in activity of the BEIIb protein compared with corresponding wild-type maize plants (cells) that are not genetically modified.

With reference to wheat, the genetic modification can be any genetic modification that leads to a detectable expression of the heterologous GWD and to a decrease in BE IIa enzyme activity or BE IIa and BE IIb enzyme activity compared with corresponding wild-type wheat plants (cells) that are not genetically modified.

The term "detectable expression of a heterologous GWD" means, within the scope of the present invention, that the expression of a heterologous GWD can be determined by measurement of the quantity of transcripts of the heterologous GWD, e.g. by Northern Blotting or RT-PCR, and that the expression of the heterologous GWD leads to an increase in the phosphate content in position C6 of the starch compared with starch from wild-type plants (cells) that do not express heterologous GWD.

An increase in phosphate content in position C6 of the starch means, in connection with the present invention, an increase in phosphate content in position C6 of the starch by at least 100%, preferably by at least 1000% and especially preferably by at least 1500%, even more especially preferably by at least 7000% compared with the phosphate content in position C6 of the starch from corresponding wild-type plants (cells).

In a further embodiment of the present invention, the detectable expression of a heterologous GWD results in an increase in the enzymatic GWD activity of the respective plant (cell) according to the invention compared to the GWD activity of a corresponding wild-type plant (cell) and/or in an increase in the amount of proteins with the activity of a GWD in the maize or wheat plants (cells) according to the invention.

The amount of GWD protein can be determined for example by Western Blotting, and the enzymatic activity of a GWD can be determined for example as described in Ritte et al. (Ritte et al., Planta 216, (2003), 798-801).

The term "decrease in activity of the BEIIb protein" means, within the scope of the present invention, with reference to maize a decrease in expression of endogenous genes that encode the BEIIb protein and/or a decrease in the amount of BEIIb protein in the maize plants (cells) according to the invention and/or preferably a decrease in enzymatic activity of BEIIb protein in the maize plants (cells) according to the invention.

The term "decrease in BE IIa enzyme activity or BE IIa and BE IIb enzyme activity" means, within the scope of the present invention, with reference to wheat a decrease in expression of endogenous genes that encode BE IIa protein and/or BE IIb protein and/or a decrease in the amount of BEIIa and/or BEIIb protein in the wheat plants (cells) according to the invention and/or preferably a decrease in enzymatic activity of BEIIa and/or BEIIb protein in the wheat plants (cells) according to the invention.

The increase/decrease in expression can be determined for example by measuring the quantity of transcripts that encode proteins with the activity of a GWD or of a BEIIb protein or of a BEIIa protein. Determination can be carried out e.g. by Northern Blotting or RT-PCR.

Determination of the BEIIb activity of maize plants takes place, in connection with the present invention, preferably after fractionation of the various isoforms of the branching enzyme from maize, as in Fisher et al., Plant Physiology 110, (1996), 611-619), in particular as in the sections described there "Reagents Used in Assays", "SBE Purification", "SBE Activity Assay" and "SBE Activity Analysis of Selected Alleles".

Determination of the BEIIa and BEIIb activity of wheat plants takes place, in connection with the present invention, preferably as described in Tetlow et al., Plant Cell 16, (2004), 694-708), in particular as in the sections described there "Enzyme Assays" and "Partial Purification of SBE Activity".

The decrease in enzymatic activity of BEIIa and/or BEIIb protein is detected, in connection with the present invention, especially preferably with the aid of activity gels, as described below under "General Methods".

A decrease in enzymatic activity of BEIIb proteins means in connection with the present invention, with reference to maize, preferably a decrease in enzymatic activity that leads to an apparent amylose content between 35 and 90 wt. %, in particular between 38-85 wt. %, preferably of 40-80 wt. % and especially preferably between 42-75 wt. %.

A "decrease in BE IIa enzyme activity or BE IIa and BE IIb enzyme activity" means, in connection with the present invention, with reference to wheat preferably a decrease in enzymatic BEIIa activity or enzymatic BEIIa and BEIIb activity, which leads to an apparent amylose content between 35 and 90 wt. %, in particular between 38-85 wt. %, preferably between 40-80 wt. % and especially preferably between 42-75 wt. %.

The term "wild-type maize plant cell" means, in connection with the present invention, that we are dealing with maize plant cells that served as starting material for the production of the maize plant cells according to the invention, which synthesize the starch according to the invention. The term "wild-type maize plant cell" does not include, in connection with the present invention, any maize plant cells from maize mutants of the ae (amylose extender), wx (waxy), du (dull), sh2 (shrunken 2), brittle-1 or of the brittle-2 genotype or of double or multiple mutants of these genotypes. The term "wild-type maize plant" means, in connection with the present invention, that we are dealing with maize plants that served as starting material for the production of the maize plants according to the invention, which synthesize the starch according to the invention. The term "wild-type maize plant" does not include, in connection with the present invention, any maize mutants of the ae (amylose extender), wx (waxy), du (dull), sh2 (shrunken 2), brittle-1 or of the brittle-2 genotype or of double or multiple mutants of these genotypes.

The term "wild-type maize plant" preferably relates to the maize inbreeding line A188, which is publicly available, for example from the Maize Genetics Cooperation Stock Center (http://maizecoop.cropsci.uiuc.edu/) at the University of Illinois, Urbana/Champaign, USA.

The term "wild-type wheat plant cell" means, in connection with the present invention, that it relates to wheat plant cells that served as starting material for the production of the wheat plant cells according to the invention, which synthesize the starch according to the invention. The term "wild-type wheat plant cell", in connection with the present invention, does not include any wheat plant cells from wheat mutants, e.g. of the wx (waxy) genotype. The term "wild-type wheat plant" means, in connection with the present invention, that it relates to wheat plants that served as starting material for the production of the wheat plants according to the invention, which synthesize the wheat starch according to the invention. The term "wild-type wheat plants", in connection with the present invention, does not include any wheat plants from wheat mutants, e.g. of the wx (waxy) genotype.

The term "wild-type wheat plant" preferably relates to the wheat variety FIELDER (CI-17268), a "soft white spring wheat", which is freely publicly available, for example from the National Small Grains Collection (NSGC; www.ars-grin.gov) (USDA, ARS, National Small Grains Research Facility, National Small Grains Collection, 1691 S 2700 W, Aberdeen, Idaho 83210; E-mail: nsg@ars-grin.gov), a division of the United States Department of Agriculture—Agricultural Research Service (USDA-ARS; http://www.ars.usda.gov). Fielder (test number CI 17268) is also available from the Alberta Stock Seed Distribution Committee, Alberta, Canada.

The term "corresponding" means, in connection with the present invention, that when comparing several objects, the objects in question, that are being compared with one another, are kept under identical conditions. In connection with the present invention, the term "corresponding" in the context of wild-type maize/wheat plant cell or wild-type maize/wheat plant, means that the plant cells or plants that are being compared with one another were bred under identical cultivation conditions and that they have an identical (cultivation) age.

In a further embodiment of the present invention, the "amylose extender mutation" and/or the increase in the activity or expression of a GWD of the plants (cells) according to the invention is brought about by mutagenesis of one or more genes. The type of mutation is irrelevant, provided that, with reference to the maize plants according to the invention, it leads to a decrease in BEIIb activity and/or to an increase in the expression or activity of a GWD, and with reference to the wheat plants according to the invention, leads to a decrease in BEIIa and/or BEIIb activity and/or to an increase in the expression or activity of a GWD.

The term "mutagenesis" means, in connection with the present invention, introduced mutations of any kind, such as deletions, point mutations (nucleotide substitutions), insertions, inversions, gene conversions or chromosome translocations.

A mutation that leads to a decrease in BEIIa and/or BEIIb activity and/or to an increase in the expression or activity of a GWD can arise spontaneously in a plant, and the corresponding plants can be selected and propagated using the methods described below.

A mutation that leads to a decrease in BEIIa and/or BEIIb activity and/or to an increase in the expression or activity of a GWD can also be produced through the use of chemical agents or high-energy radiation (e.g. X-rays, neutron, gamma, or UV radiation).

Agents that can be used for the production of chemically induced mutations, and the mutations resulting from the action of the corresponding mutagens, are described for example by Ehrenberg and Husain (1981, Mutation Research 86, 1-113) and Müller (1972, Biologisches Zentralblatt 91 (1), 31-48).

The production of rice mutants using gamma rays, ethyl methane sulfonate (EMS), N-methyl-N-nitrosourea or sodium azide ($NaN_3$) is described for example by Jauhar and Siddiq (1999, Indian Journal of Genetics, 59 (1), 23-28), Rao (1977, Cytologica 42, 443-450), Gupta and Sharma (1990, Oryza 27, 217-219) and Satoh and Omura (1981, Japanese Journal of Breeding 31 (3), 316-326). The production of wheat mutants using $NaN_3$ or maleic acid hydrazide is described by Arora et al. (1992, Annals of Biology 8 (1), 65-69). A review of the production of wheat mutants using various types of high-energy radiation and chemical agents is presented by Scarascia-Mugnozza et al. (1993, Mutation Breeding Review 10, 1-28). Svec et al. (1998, Cereal Research Communications 26 (4), 391-396) describe the use of N-ethyl-N-nitrosourea for the production of mutants in triticale. The use of MMS (methyl methanesulfonic acid) and gamma radiation for the production of millet mutants is described by Shashidhara et al. (1990, Journal of Maharashtra Agricultural Universities 15 (1), 20-23).

In connection with the present invention, plants (cells) according to the invention can also be produced using the so-called insertion mutagenesis (review article: Thorneycroft et al., 2001, Journal of Experimental Botany 52 (361), 1593-1601). Insertion mutagenesis, in connection with the present invention, means in particular the insertion of transposons or so-called transfer DNA (T-DNA) in a gene or in the vicinity of a gene encoding a protein with the activity of a GWD or of a BEIIb or of a BEIIa, whereby the activity of a protein with the activity of a GWD is increased in the cell in question or the activity of the BEIIb protein or of a BEIIa protein is decreased. The transposons can either be those that occur naturally in the cell (endogenous transposons), or that do not occur naturally in said cell, but were introduced into the cell by methods of genetic engineering, such as transformation of the cell (heterologous transposons). Alteration of the expression of genes by transposons is known by a person skilled in the art. A review of the use of endogenous and heterologous transposons as tools in plant biotechnology is presented in Ramachandran and Sundaresan (2001, Plant Physiology and Biochemistry 39, 234-252).

T-DNA insertion mutagenesis is based on the fact that certain segments (T-DNA) of Ti-plasmids from *Agrobacterium* can be integrated into the genome of plant cells. The place of integration in the plant chromosome is not fixed, but can take place at any point. If the T-DNA is integrated into a segment or in the vicinity of a segment of the chromosome that represents a gene function, this can lead to increase or decrease in gene expression and hence to a change in the activity of a protein encoded by the gene in question.

The sequences (in particular transposons or T-DNA) inserted into the genome are characterized in that they contain sequences that lead to activation of regulatory sequences of a gene that encodes a protein with the activity of a GWD ("activation tagging"). Preferably sequences inserted into the genome (in particular transposons or T-DNA) are characterized in that they are integrated in the vicinity of endogenous nucleic acid molecules in the genome of the plant cell or of the plant, which encode a protein with the activity of a GWD.

Plants (cells) according to the invention can also for example be produced by the method of so-called "activation tagging" (see e.g. Walden et al., Plant J. (1991), 281-288; Walden et al., Plant Mol. Biol. 26 (1994), 1521-1528). This method is based on the activation of endogenous promoters by "enhancer" sequences, such as the enhancer of the 35S RNA promoter of the cauliflower mosaic virus or the octopine synthase enhancer.

The term "T-DNA activation tagging" means, in connection with the present invention, a T-DNA fragment that contains "enhancer" sequences and, through integration in the genome of a plant cell, leads to an increase in the expression or activity of a protein with the activity of a GWD.

The term "genome" means, in connection with the present invention, all of the hereditary material present in a plant cell. It is known by a person skilled in the art that in addition to the cell nucleus, other compartments (e.g. plastids, mitochondria) also contain hereditary material.

The term "transposon activation tagging" means, in connection with the present invention, a transposon that contains "enhancer" sequences and, through integration in the genome of a plant cell, leads to an increase in the expression or activity of a protein with the activity of a GWD.

It is known by a person skilled in the art that in the case of polyploid plants, such as wheat, in certain circumstances expression of the amylose extender phenotype requires three nonfunctional BEIIa or BEIIa and BEIIb mutations (on the A, B and D sub-genome) to be present homozygously.

All of these methods are basically suitable for production of the "amylose extender mutation" and/or for increasing the expression or activity of a GWD and therefore for the production of the plant cells according to the invention or the plants according to the invention.

Mutations in the corresponding genes, in particular in genes that encode BEIIa, BEIIb or a GWD, can be detected by methods that are known by a person skilled in the art. For this it is possible in particular to employ analyses based on hybridizations with probes ("Southern Blot"), amplification by polymerase chain reaction (PCR), sequencing of relevant genomic nucleic acid fragments and searching for individual nucleotide substitutions. A method of identifying mutations on the basis of hybridization patterns is e.g. searching for restriction fragment length differences (restriction fragment length polymorphism, RFLP) (Nam et al., 1989, The Plant Cell 1, 699-705; Leister and Dean, 1993, The Plant Journal 4 (4), 745-750). A PCR-based method is e.g. analysis of amplified fragment length differences (amplified fragment length polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160). Amplified fragments cleaved with restriction endonucleases (cleaved amplified polymorphic sequences, CAPS) can also be employed for the identification of mutations (Konieczny and Ausubel, 1993, The Plant Journal 4, 403-410; Jarvis et al., 1994, Plant Mol. Biol. 24, 685-687; Bachem et al., 1996, The Plant Journal 9 (5), 745-753). Methods for the determination of SNPs have been described by, among others: Qi et al. (2001, Nucleic Acids Research 29 (22), e116), Drenkard et al. (2000, Plant Physiology 124, 1483-1492) and Cho et al. (1999, Nature Genetics 23, 203-207). In particular, methods are suitable that make it possible to investigate many plants in a short time for mutations in particular genes. Such a method, called TILL-ING ("Targeting Induced Local Lesions in Genomes") has been described by McCallum et al. (2000, Plant Physiology 123, 439-442).

All of these methods are basically suitable for the identification of plant cells according to the invention or of plants according to the invention.

In a further embodiment of the present invention, the genetic modification of the maize/wheat plant (cell) according to the invention comprises the introduction of at least one foreign nucleic acid molecule into the genome of the maize/wheat plant cell or into the genome of the maize/wheat plant.

In this context, the term "genetic modification" means, with reference to GWD, the insertion of at least one foreign nucleic acid molecule into the genome of a maize or wheat plant (cell), with said insertion of said molecule leading to an increase in the expression or activity of a protein with the activity of a GWD. With reference to the amylose extender mutation in maize, a foreign nucleic acid molecule can be any nucleic acid molecule that causes a decrease in BEIIb activity in the plant cell or plant. With reference to the amylose extender mutation in wheat, a foreign nucleic acid molecule can be any nucleic acid molecule that causes a decrease in BEIIa or in BEIIa and BEIIb activity in the plant cell or plant.

Through insertion of a foreign nucleic acid molecule, the maize or wheat plants (cells) according to the invention are altered in their genetic information.

The presence or the expression of at least one foreign nucleic acid molecule leads to a phenotypic modification. "Phenotypic modification" preferably means a measurable change of one or more functions of the cells. For example, the genetically modified maize or wheat plants (cells) can, with reference to GWD, owing to the presence or on expression of inserted foreign nucleic acid molecules, show an increase in the expression or activity of a protein with the activity of a GWD. With reference to the BEIIb protein, the maize plants (cells) according to the invention display, owing to the presence or the expression of inserted foreign nucleic acid molecules, a decrease in BEIIb activity. With reference to the BEIIa or to the BEIIa and BEIIb protein, the wheat plants (cells) according to the invention display, owing to the presence or the expression of inserted foreign nucleic acid molecules, a decrease in BEIIa or in BEIIa and BEIIb activity.

The term "foreign nucleic acid molecule" means, in connection with the present invention, such a molecule that either does not occur naturally in corresponding wild-type plant cells, or that does not occur naturally in the precise spatial arrangement in wild-type plant cells or that is localized at a place in the genome of the wild-type plant cell at which it does not occur naturally. Basically, a foreign nucleic acid molecule can be, with reference to the GWD, any nucleic acid molecule that causes an increase in the expression or activity of a protein with the activity of a GWD in the plant cell or plant. With reference to the amylose extender mutation in maize, a foreign nucleic acid molecule can be any nucleic acid molecule that causes a decrease in BEIIb activity in the plant cell or plant. With reference to the amylose extender mutation in wheat, a foreign nucleic acid molecule can be any nucleic acid molecule or nucleic acid molecules that causes (cause) a decrease in BEIIa-activity or in BEIIa and BEIIb activity in the plant cell or plant.

Preferably the foreign nucleic acid molecule is a recombinant nucleic acid molecule, consisting of various elements, whose combination or specific spatial arrangement does not occur naturally in plant cells.

The term "recombinant nucleic acid molecule" means, in connection with the present invention, a nucleic acid molecule that has various nucleic acid molecules that do not occur naturally in a combination as in a recombinant nucleic acid molecule. Thus, the recombinant nucleic acid molecules have, for example in addition to the nucleic acid molecules that encode a protein with the activity of a GWD and/or a BEIIb protein or fragments thereof (e.g. genomic nucleic acid molecules or cDNAs), additional nucleic acid sequences that do not occur naturally in combination with these nucleic acid molecules. The recombinant nucleic acid molecule has, for example, regulatory sequences (e.g. promoters, termination signals, enhancers), preferably regulatory sequences that are heterologous with respect to the nucleic acid molecule that encodes the GWD and/or the BEIIb protein or fragments of this protein. Heterologous means, in this context, that the regulatory sequence is not the actual endogenous regulatory sequence of the GWD gene and/or BEIIb gene and/or BEIIa gene that is used. Moreover, regulatory sequences are preferred that are active in plant tissue, preferably in the endosperm.

Methods for the production of recombinant nucleic acid molecules are known by a person skilled in the art and include methods of genetic engineering, such as the joining of nucleic acid molecules by ligation, genetic recombination or the new synthesis of nucleic acid molecules (see e.g. Sambrook et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929).

The foreign nucleic acid molecule or molecules used for genetic modification can be a composite or several separate nucleic acid constructs, in particular so-called single, double or triple constructs. Thus, the foreign nucleic acid molecule can be for example a so-called "double construct", by which we mean a single vector for plant transformation, which contains the genetic information both for decrease/inhibition of BEIIb activity and for increase in the expression or activity of the GWD.

In a further embodiment of the invention, instead of inserting a double construct in the genome of the plant cell, several different foreign nucleic acid molecules/polynucleotides are inserted in succession, where one of these foreign nucleic acid molecules is for example a DNA molecule that causes an increase in the expression or activity of the GWD, and a second foreign nucleic acid molecule for example encodes an antisense-RNA, which mediates a decrease in BEIIb activity. Basically, in the construction of said second foreign nucleic acid molecules, however, cosuppression, ribozymal or double-stranded RNA constructs or in vivo mutagenesis are suitable, provided they lead to a decrease in BEIIb activity.

The foreign nucleic acid molecules can be inserted into the genome of the plant cell at the same time ("cotransformation") or successively, i.e. one after another ("supertransformation").

The foreign nucleic acid molecules/polynucleotides can also be introduced into various individual plants of a species. It is then possible first to produce plants for which the expression of a heterologous GWD is detectable or for which the BEIIb activity is reduced. In an especially preferred embodiment of the present invention, using subsequent crossing, maize plants are produced for which the expression of a heterologous GWD is detectable and the BEIIb activity is reduced. In a further especially preferred embodiment of the present invention, using subsequent crossing, wheat plants are produced for which the expression of a heterologous GWD is detectable and the BEIIa or the BEIIa and BEIIb activity is reduced.

Furthermore, for introducing a foreign nucleic acid molecule/polynucleotide or for production of the plant cells according to the invention or the plants according to the invention, instead of a wild-type plant cell or plant it is possible to employ a mutant, which is characterized in that it already has a reduced BEIIb activity or expression of a heterologous GWD. For example, the use of maize amylose extender mutants is basically conceivable, into which a foreign nucleic acid molecule is inserted, which leads to an increase in the expression or activity of the GWD compared with corresponding wild-type plants (cells).

In a further embodiment of the present invention, the presence and/or the expression of one or more foreign nucleic acid molecules/polynucleotides leads, relative to the maize plants (cells) according to the invention, to a decrease in BEIIb activity.

In a further embodiment of the present invention, the presence and/or the expression of one or more foreign nucleic acid molecules/polynucleotides leads, relative to the wheat plants (cells) according to the invention, to a decrease in BEIIa activity or in BEIIa and BEIIb activity.

This can be achieved by various methods that are known to a person skilled in the art. These include for example the expression of a corresponding antisense-RNA, or of a double-stranded RNA construct, the provision of molecules or vectors that mediate a cosuppression effect, the expression of a correspondingly constructed ribozyme, which specifically cleaves transcripts that encode BEIIb or BEIIa (wheat), or so-called "in vivo mutagenesis". Moreover, the decrease in BEIIb and/or BEIIa activity can also be brought about by simultaneous expression of sense and antisense RNA molecules of the BEIIb (amylose extender) and/or of the BEIIa gene. A person skilled in the art is familiar with these methods.

Furthermore, it is known that in planta the formation of double-stranded RNA molecules of promoter sequences in trans can lead to methylation and transcriptional inactivation of homologous copies of said promoter (Mette et al., 2000, EMBO J. 19, 5194-5201).

For inhibition of gene expression by antisense or cosuppression technology, it is possible for example to use a DNA molecule that includes the complete sequence coding for BEIIa or BEIIb, as well as DNA molecules that only include portions of the coding sequence, but these portions must be long enough to produce an antisense effect or cosuppression effect in the cells. Sequences with a minimum length of 21-23 bp, preferably with a minimum length of 50 bp, especially preferably with a length of 100-500 by are generally suitable.

For antisense or cosuppression approaches it is also appropriate to use polynucleotide sequences that have a high degree of identity to the sequences occurring endogenously in the plant cell, which code for BEIIa or BEIIb. The minimum identity should be greater than approx. 90%. The use of sequences with identities of at least 95%, in particular of at least 98% is to be preferred.

Moreover, to achieve an antisense or a cosuppression effect it is also conceivable to use introns, i.e. noncoding regions of genes that code for BEIIa or BEIIb.

The use of intron sequences for the inhibition of the expression of genes that encode proteins of the starch biosynthesis was described in WO 97/04112, WO 97/04113, WO 98/37213, WO 98/37214.

A person skilled in the art knows how to achieve an antisense and a cosuppression effect. The method of cosuppression inhibition was described for example by Jorgensen (1990, Trends Biotechnol. 8, 340-344), Niebel et al. (1995, Top. Microbiol. Immunol. 197, 91-103), Flavell et al. (1995, Curr. Top. Microbiol. Immunol. 197, 43-46), Palauqui and Vaucheret (1995, Plant Mol. Biol. 29, 149-159), Vaucheret et al. (1995, Mol. Gen. Genet. 248, 311-317), de Borne et al. (1994, Mol. Gen. Genet. 243, 613-621).

The expression of ribozymes to reduce the activity of particular enzymes in cells is also known by a person skilled in the art and is described for example in EP-B1 0321201. The expression of ribozymes in plant cells was for example described by Feyter et al. (1996, Mol. Gen. Genet. 250, 329-338).

Furthermore, reduction of BEIIa or BEIIb activity in plant cells can also be achieved by so-called "in vivo mutagenesis", in which transformation of cells is used for inserting a hybrid RNA-DNA oligonucleotide ("chimeroplast") in cells (Kipp et al., Poster Session at the 5$^{th}$ International Congress of Plant Molecular Biology, 21-27 Sep. 1997, Singapore; R. A. Dixon and C. J. Arntzen, Meeting report on Metabolic Engineering in Transgenic Plants, Keystone Symposia, Copper Mountain, Colo., USA, 1997, TIBTECH 15, 441-447; WO 95/15972; Kren et al., 1997, Hepatology 25, 1462-1468; Cole-Strauss et al., 1996, Science 273, 1386-1389; Beetham et al., 1999, PNAS 96, 8774-8778).

A portion of the DNA component of the RNA-DNA oligonucleotide is homologous to a polynucleotide sequence of an endogenous BEIIa or BEIIb gene but has, compared to the polynucleotide sequence of an endogenous BEIIa or BEIIb gene, a mutation or contains a heterologous region that is surrounded by the homologous regions. By means of base pairing of the homologous regions of the RNA-DNA oligonucleotide and of the endogenous polynucleotide, followed by homologous recombination, the mutation or heterologous region contained in the DNA component of the RNA-DNA oligonucleotide can be transferred into the genome of a plant cell. This leads to a decrease in activity of BEIIa or BEIIb.

Moreover, decrease in BEIIa or BEIIb activity in the plant cells can also be brought about by the simultaneous expression of sense and antisense RNA molecules of the particular target gene that is to be repressed, preferably of the BEIIa or BEIIb (amylose extender) gene.

This can for example be achieved through the use of chimeric constructs, which contain "inverted repeats" of the particular target gene or portions of the target gene. The chimeric constructs then encode sense and antisense RNA molecules of the particular target gene. Sense and antisense RNA are synthesized in planta simultaneously as one RNA molecule, wherein sense and antisense RNA are separated from each other by a spacer and can form a double-stranded RNA molecule (RNAi technology).

It has been shown that the insertion of inverted-repeat DNA constructs in the genome of plants is a very efficient method for repressing the genes corresponding to the inverted-repeat DNA constructs (Waterhouse et al., 1998, Proc. Natl. Acad. Sci. USA 95, 13959-13964; Wang and Waterhouse, 2000, Plant Mol. Biol. 43, 67-82; Singh et al., 2000, Biochemical Society Transactions 28 (6), 925-927; Liu et al., 2000, Biochemical Society Transactions 28 (6), 927-929; Smith et al., 2000, Nature 407, 319-320; WO 99/53050). Sense and antisense sequences of the target gene or target genes can also be expressed separately from each other by the same or different promoters (Nap et al., 6$^{th}$ International Congress of Plant Molecular Biology, 18-24 Jun. 2000, Quebec, Poster S7-27, Report Session S7).

Decrease in BEIIa or BEIIb activity can therefore also be achieved through the production of double-stranded RNA molecules of the BEIIa or BEIIb gene. For this, preferably "inverted repeats" of DNA molecules that have been derived from BEIIa or BEIIb genes are inserted in the genome of plants, the DNA molecules that are to be transcribed being under the control of a promoter, which regulates the expression of said DNA molecules.

Furthermore, it is known that the formation of double-stranded RNA molecules of promoter-DNA molecules in plants in trans can lead to a methylation and a transcriptional inactivation of homologous copies of these promoters, which will be designated as target promoters hereinafter (Mette et al., 2000, EMBO J. 19, 5194-5201).

Through inactivation of the target promoter it is thus possible to reduce gene expression of the BEIIa or BEIIb gene (target gene), which is naturally under the control of this target promoter.

That is, the DNA molecules that include the target promoters of the genes that are to be repressed (target genes) are in this case, in contrast to the original function of promoters in plants, used not as regulating elements for the expression of genes or cDNAs, but themselves as transcribable DNA molecules.

For the production of the double-stranded target promoter RNA molecules in planta, which may be present there as RNA hairpin molecules, it is preferable to use constructs that contain "inverted repeats" of the target promoter-DNA molecules, with the target promoter-DNA molecules being under the control of a promoter that regulates the gene expression of said target promoter-DNA molecules. These constructs are then inserted in the genome of plants. Expression of the "inverted repeats" of said target promoter-DNA molecules leads in planta to the formation of double-stranded target promoter-RNA molecules (Mette et al., 2000, EMBO J. 19, 5194-5201). In this way the target promoter can be inactivated.

Decrease in BEIIa or BEIIb activity in the plant cells can thus also be achieved through the production of double-stranded RNA molecules of promoter sequences of the BEIIa or BEIIb gene. For this, preferably "inverted repeats" of promoter-DNA molecules of BEIIa or BEIIb promoters are inserted in the genome of plants, with the target promoter-DNA molecules that are to be transcribed (BEIIa or BEIIb promoter) being under the control of a promoter that regulates the expression of said target promoter-DNA molecules.

Moreover, it is known by a person skilled in the art that it is possible to achieve a decrease in BEIIa or BEIIb activity through the expression of nonfunctional derivatives, in particular transdominant mutants, of the enzymes and/or through the expression of antagonists/inhibitors of the enzymes.

Antagonists/inhibitors of the enzymes can for example be antibodies, antibody fragments or molecules with similar binding properties. For example, a cytoplasmic scFv-antibody was used in order to modulate the activity of the phytochrome A-protein in genetically engineered tobacco plants (Owen, 1992, Bio/Technology 10, 790-794; Review: Franken et al., 1997, Current Opinion in Biotechnology 8, 411-416; Whitelam, 1996, Trends Plant Sci. 1, 268-272).

Suitable promoters in connection with the present invention are constitutive promoters, such as the promoter of the 35S RNA of the cauliflower mosaic virus (Odell et al., 1985, Nature, 313, 810-812), the ubiquitin promoter from maize (Christensen et al., Plant Mol. Biol. 18, (1992), 675-689), the ubiquitin promoter from rice (Liu et al., Plant Science 165, (2003), the rice actin promoter (Zhang, et al., Plant Cell 3:1150-1160, 1991), the cassaya vein mosaic virus (CVMV) promoter (Verdaguer et al., Plant Mol. Biol. 31: 1129-1139), the maize histon H3C4 promoter (U.S. Pat. No. 6,750,378) or the Cestrum YLCV promoter (yellow leaf curling virus; WO 01 73087; Stavolone et al., 2003, Plant Mol. Biol. 53, 703-713).

Especially preferably they are tissue-specific regulatory sequences, which are active in maize or wheat tissue, preferably in the endosperm of maize or wheat plants. Other endosperm-specific promoters in maize or wheat are the promoter of the 10 kD zein gene from maize (Kirihara et al. (1988) Gene 71: 359-370), of the 15 kD zein gene from maize (Hoffmann et al. (1987) EMBO J. 6: 3213-3221; Schernthaner et al. (1988) EMBO J. 7: 1249-1253; Williamson et al. (1988) Plant Physiol. 88: 1002-1007), of the 27 kd zein gene from maize (Prat et al. (1987) Gene 52: 51-49; Gallardo et al. (1988) Plant Sci. 54: 211-281), of the 19 kD zein gene from maize (Marks et al. (1985) J. Biol. Chem. 260: 16451-16459). The relative transcriptional activities of these promoters in maize are described in Kodrzyck et al., (1989), Plant Cell 1, 105-114).

Other promoters that are conceivable in conjunction with the present invention are the promoter of the sucrose synthase gene (Yang, N.-S. And Russel, D. (1990) Proc. Natl. Acad Sci 87: 4144-4148), of the waxy gene (Unger et al. (1991) Plant Physiol. 96: 124), of the sh 2 gene (Bhave et al. (1990) Plant Cell 2: 581-588, of the bt 2 gene (Bae et al. (1990) Maydica 35: 317-322). Also the HMG promoter (also called wheat glutenin HMWG promoter) from wheat (Colot et al., EMBO J. 6, (1987, 3559-3564; Clarke and Appels, Genome 41, (1998), 865-871), the USP promoter, the phaseolin promoter, promoters of zein genes from maize (Pedersen et al., Cell 29 (1982), 1015-1026; Quatroccio et al., Plant Mol. Biol. 15 (1990), 81-93), the glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218), the globulin promoter (Nakase et al., 1996, Gene 170(2), 223-226) or the prolamine promoter (Qu and Takaiwa, 2004, Plant Biotechnology Journal 2(2), 113-125).

Intron sequences can also be present between the promoter and the coding region. Said intron sequences can lead to stability of expression and to increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4):895-899; Rose and Beliakoff, 2000, Plant Physiol. 122 (2), 535-542; Vasil et al., 1989, Plant Physiol. 91, 1575-1579; XU et al., 2003, Science in China Series C Vol. 46 No. 6, 561-569). Suitable intron sequences are for example the first intron of the sh1 gene from maize (Maas et al. (1991) Plant. Mol. Biol. 16: 199-207, the first intron of the poly-ubiquitin gene 1 from maize, the first intron of the EPSPS gene from rice or one of the first two introns of the PAT1 gene from *Arabidopsis*, also introns of the Adh-1 or Bz-1 gene from maize (Callis et al. (1987) Genes Dev. 1: 1183-1200), intron 3 of the maize actin gene (Luehrsen, K. R. and Walbot, V. (1991) Mol. Gen. Genet. 225: 81-93) or of the Adh1 intron 6 (Oard et al. (1989) Plant Cell Rep 8: 156-160). The present invention also relates to reproductive material of plants according to the invention.

The term "reproductive material" includes in connection with the present invention preferably endosperm-containing seeds(grains) of the maize or wheat plants according to the invention.

In a further embodiment, the present invention relates to a method of production of the maize starch according to the invention comprising the step of extraction of the starch from a maize plant according to the invention and/or from a maize plant cell according to the invention.

In a further embodiment of the present invention, the maize starch according to the invention is extracted from a maize plant according to the invention containing maize plant cells according to the invention, from reproductive material of a maize plant according to the invention and/or from starch-storing parts of a maize plant according to the invention.

The term "starch-storing parts" means, in connection with the present invention, those parts of a plant in which starch, as opposed to transient leaf starch, is stored as reserve for perennation for quite long periods. Preferred starch-storing plant parts are maize/wheat grains, and maize/wheat grains containing an endosperm are especially preferred.

In a further embodiment, the present invention relates to a method of production of a wheat starch according to the invention comprising the step of extraction of the starch from a wheat plant according to the invention and/or from a wheat plant cell according to the invention.

In a further embodiment of the present invention, the wheat starch according to the invention is extracted from a wheat plant according to the invention containing wheat plant cells according to the invention, from reproductive material of a wheat plant according to the invention and/or from starch-storing parts of a wheat plant according to the invention.

Preferably the method according to the invention also includes the step of harvesting the cultivated maize or wheat plants according to the invention or the starch-storing plant parts and/or the reproductive material of the maize or wheat plants according to the invention prior to extraction of the starch. In a further embodiment, the method according to the invention also includes the step of cultivation of the maize or wheat plants prior to harvesting.

Methods of extraction of the starch from plants according to the invention or from starch-storing parts of plants according to the invention are known by a person skilled in the art. For example, methods of extraction of the starch from various starch-storing plants are described, e.g. in Starch: Chemistry and Technology (Publ.: Whistler, BeMiller and Paschall (1994), 2nd edition, Academic Press Inc. London Ltd; ISBN 0-12-746270-8; see e.g. Chapter XII, pages 412-468: Maize and *Sorghum* Starches: Production; by Watson; Chapter XV, pages 491 to 506: Wheat Starch: Production, Modification and Uses; by Knight and Oson) or in Eckhoff et al., Cereal Chem. 73 (1996), 54-57). Extraction of maize starch on an industrial scale is as a rule achieved by means of so-called "wet milling". Devices that are usually employed for the extraction of starch from plant material are separators, decanters, hydrocyclones, spray dryers and fluidized-bed dryers.

In a further embodiment, the present invention relates to maize meal (=maize flour) containing the maize starch according to the invention.

In a further embodiment, the present invention relates to wheat meal (=wheat flour) containing the wheat starch according to the invention.

Starch-storing parts of plants can be processed into meals (flours). For the production of maize or wheat meals, the endosperm-containing maize grains are ground and sieved. Starch is a principal constituent of the endosperm. The maize/wheat starch according to the invention is, apart from proteins and lipids, the most important constituent of the maize/wheat meal (flour) according to the invention (approx. 65 to 75 wt. % of the dry weight of the meal(flour)). The properties of the maize/wheat meals (flours) according to the invention are therefore greatly influenced by the maize or wheat starch according to the invention contained in the maize or wheat meal (flour).

The term "maize meal (=maize flour)" means, in connection with the present invention, a powder obtained by grinding maize grains of maize plants according to the invention, wherein the maize grains consist of maize plant cells according to the invention. Optionally, the maize grains are dried before grinding and are comminuted and/or sieved after grinding.

A further object of the present invention is a method of production of the maize meal (=maize flour) according to the invention comprising the step of grinding at least one maize plant according to the invention. In a further preferred embodiment of the method according to the invention, for the production of the maize meal (=maize flour) according to the invention, maize grains that consist of maize plant cells according to the invention are ground.

The term "wheat meal" (=wheat flour) means, in connection with the present invention, a powder obtained by grinding wheat grains, wherein the wheat grains contain wheat plant cells according to the invention. Optionally, the wheat grains are dried before grinding and are comminuted and/or sieved after grinding.

A further object of the present invention is a method of production of the wheat meal (=wheat flour) according to the invention comprising the step of grinding at least one wheat plant according to the invention. In a further preferred embodiment of the method according to the invention, for the production of the meal (flour) according to the invention, wheat grains that consist of wheat plant cells according to the invention are ground.

Preferably, the method according to the invention for the production of maize/wheat meals (flours) according to the invention also includes the step of harvesting the maize/wheat plants according to the invention or the maize/wheat grains according to the invention of these maize/wheat plants before grinding, preferably washing the maize/wheat plants according to the invention or the maize/wheat grains according to the invention before grinding and in addition the step of cultivation of the maize/wheat plants according to the invention prior to harvesting.

In a further embodiment of the present invention, the method according to the invention for production of maize or wheat meals (flours) includes processing of the maize or wheat plants according to the invention before grinding.

Said processing can, in connection with the production of the grains, for example be heat treatment, preferably thermal treatment and/or drying. The comminution of the maize or wheat plants according to the invention, of starch-storing parts or grains of said plants before grinding can also constitute processing in the sense of the present invention. The removal of plant tissue, such as husks of the grains, before grinding also constitutes processing before grinding in the sense of the present invention.

In a further embodiment of the present invention, the method according to the invention for production of maize or wheat meals (flours) after grinding includes processing of the ground product. The ground product can for instance be sieved after grinding, e.g. in order to produce meals (flours) of various types.

In a further embodiment, the present invention relates to the use of maize meal (=maize flour), maize starch, wheat meal (=wheat flour) or wheat starch according to the invention for the production of a foodstuff.

In a further embodiment, the present invention relates to the use of maize meal (=maize flour), maize starch, wheat meal (=wheat flour) or wheat starch according to the invention as a prebiotic.

In a further embodiment, the present invention relates to a composition containing the maize starch according to the invention and at least one nutritional supplement.

In a further embodiment, the present invention relates to a composition containing the maize meal (=maize flour) according to the invention and at least one nutritional supplement.

In a further embodiment, the present invention relates to a composition containing the wheat starch according to the invention and at least one nutritional supplement.

In a further embodiment, the present invention relates to a composition containing the wheat meal (=wheat flour) according to the invention and at least one nutritional supplement.

Nutritional supplements are, in connection with the present invention, for example vitamins (e.g. vitamin A, B1, B2, B3, B5, B6, B9, B12, C, D, E, F, K), provitamins, antioxidants, trace elements (e.g. chromium, iron, fluorine, iodine, cobalt, copper, manganese, molybdenum, selenium, vanadium, zinc), minerals (e.g. calcium, chlorine, potassium, magnesium, phosphorus, sulfur, sodium), flavorings, dyes, oils, fats, fatty acids, in particular (poly) unsaturated fatty acids, essential fatty acids, carbohydrates (e.g. starches, galactooligosaccharides, gentiobiose, tagatose), roughage (e.g. cellulose, hemicellulose, pectin, ligin), prebiotics (e.g. oligofructose, oligosaccharides, chitosan, beta glucans, arabinogalactan), probiotics (e.g. bifidobacteria, lactic acid bacteria e.g. of the genus *Lactobacillus*), i.e. nonpathogenic microorganisms, which are added live or as spores to the foodstuffs and can have a beneficial influence on the intestinal flora.

Production of the compositions according to the invention can for example take place by simple mixing.

In a further embodiment, the present invention relates to a foodstuff containing the maize starch according to the invention or the wheat starch according to the invention.

In a further embodiment, the present invention relates to a foodstuff containing the maize meal (=maize flour) according to the invention or the wheat meal (=wheat flour) according to the invention.

In a further embodiment, the present invention relates to a foodstuff containing the composition according to the invention.

Typical foodstuffs that can be produced using the maize starch according to the invention, the maize meal (=maize flour) according to the invention or the composition according to the invention, are for example tortillas, tortilla chips, baked goods (e.g. bread, corn bread, rolls, cookies, cakes, waffles, muffins, maize dough-cakes), pancakes, pizza, polenta, pasta products (e.g. noodles), cornmeal mush (USA), porridge (GB), stews, sauces, corn meal pudding, milk products (e.g. yoghurt, quark, ices), puddings, spreads (e.g. butter, margarine), beverages, beverage powders, ready-to-serve meals, (breakfast) cereals, enchilada, sausages, meat products, children's food, ketchup, mayonnaise, barbecue sauces etc.

General Methods

Methods that can be used for carrying out the invention described above are described in the following. These methods represent concrete applications of the present invention, but do not restrict the present invention to these methods.

1) Plant Material and Cultivation

Maize plants: *Zea mays*, variety A188
   *Zea mays*, mutant ae1 (amylose extender) variety W64A
Wheat plants: *Triticum aestivum*, variety Fielder The maize plants are cultivated in the greenhouse in the following conditions:

Substrate:
   Special sowing mix
   80% younger peat
   20% black peat
   100 kg/m$^3$ sand
   40 kg/m$^3$ moist clay
   structure: fine
   pH value: 5.3-6.1
   Basal dressing: 2 kg/m$^3$ and 100 g/m$^3$ Radigen (Theraflor GmbH; Iserlohn; Germany) (composition: 5% MgO; 2% Fe; 1.5% Cu; 1% Mn; 0.8% Mo; 0.6% B; 0.5% Zn)
Pots: 10 L containers
Spacing: Max. 6 plants/m$^2$
Watering: Keep plants uniformly moist, but definitely avoid water-logging and drying-out of the substrate
Fertilizer: 1 TAB Plantosan 4 g (composition 15% N; 8% P$_2$O$_5$; 15% K$_2$O; 2% MgO+trace elements) at the 4-leaf stage
1 TAB Plantosan after a further 3 weeks
Temperature: day 22-25° C./night 16° C.
Light: 18 hours, 350-400 µEinstein/s/m
Humidity: 50% rel.

The wheat plants are cultivated in the greenhouse in the following conditions:

Substrate:
   Special mix
   100% younger peat
   200 L/m$^3$ sand
   180 kg/m$^3$ moist clay
   20% perlite
   structure: medium-coarse
   pH value 5.5-6.0
   Basal dressing: 2 kg/m$^3$ 12-14-24 (+3) and 100 mg/m$^3$ Radigen (Theraflor GmbH; Iserlohn; Germany) (composition: 5% MgO; 2% Fe; 1.5% Cu; 1% Mn; 0.8% Mo; 0.6% B; 0.5% Zn)
Pots: square, volume 1.6 l
Spacing: 42 pots/m$^2$
Watering: keep plants uniformly moist, but definitely avoid waterlogging and drying-out of the substrate
Fertilizer: 1 g/plant in three doses, Hakaphos (composition 15% N; 10% P$_2$O$_5$; 15% K$_2$O; 2% MgO) manufacturer Compo
Temperature: day 20-25° C./night 16° C.
Light: 18 hours, 350-400 µEinstein/s/m
Humidity: rel. 50%
Plant Protection According to Indication:
   Pirimicarb® (Zeneca), Confidor® (Bayer), Neem Azal® (Trifolio-M GmbH), Vertimec® (Syngenta)

2) Transformation and Regeneration of Maize and Wheat Plants

Maize plants were transformed and regenerated according to the method described by Ishida et al. (1996 Nature Biotechnology Vol 14: 745-750).

Transformation and regeneration of the wheat plants were carried out according to the method of Jones et al., (Jones H. D., Doherty A., Wu H., 2005. Review of methodologies and a protocol for the *Agrobacterium*-mediated transformation of wheat. Plant Methods 2005, 1:5 doi:10.1186/1746-4811-1-5).

3) Production and Identification of Genetically Modified Maize Plants that have an Amylose Extender Mutation and Detectable GWD Expression For crossing the transgenic maize plants with detectable GWD expression with the ae1-mutant the variety W64A, the ae1-mutant was put out 7-10 days beforehand and the transgenic lines then correspondingly after reaching the 2-leaf stage of the mutant. This is necessary to synchronize development of the flowers. The ae1-mutant was used as pollen donor (male crossing partner) and the carriers with detectable GWD expression as female crossing partner.

The resultant F1 generation was then self-pollinated and seeds were selected that are homozygous both for the ae1 mutation and for the GWD gene.

4) Production, Harvesting and Processing of Maize Grains

For the production of sufficient amounts of study material, maize plants were grown under greenhouse conditions and after reaching complete maturity (approx. 40 days after pollination) the cobs were harvested. For further drying, the mature (i.e. fully developed) maize cobs were stored for 3-7 days at 37° C.

After drying (below 13% moisture, measured with the "Grain Moisture Tester Riceter J301" instrument from the company Kett Electric Laboratory, Tokyo, Japan), the grains were removed from the cobs and used as starting material for analyses of the whole grain, for example grain weight.

5) Determination of Phosphate Content of the Starch in Position C6 (C6-P Content)

In starch, positions C3 and C6 of the glucose units may be phosphorylated. To determine the C6-P content of starch (modified according to Nielsen et al., 1994, Plant Physiol. 105: 111-117), 50 mg maize meal (flour)/starch was hydrolyzed in 500 ml 0.7 M HCl for 4 h at 95° C., shaking continuously. Then the preparations were centrifuged for 10 min at 15 500 g and the supernatants were purified using a filter membrane (0.45 µM) to remove suspended matter and turbidity. From the clear hydrolyzate, 20 µl was mixed with 180 µl imidazole buffer (300 mM imidazole, pH 7.4; 7.5 mM $MgCl_2$, 1 mM EDTA and 0.4 mM NADP). Measurement was carried out in a photometer at 340 nm. After determination of basic absorption, the enzyme reaction was started by adding 2 units of glucose-6-phosphate dehydrogenase (from *Leuconostoc mesenteroides*, Boehringer Mannheim). The change in absorption is based on equimolar conversion of glucose-6-phosphate and NADP to 6-phosphogluconate and NADPH, with the formation of NADPH being detected at the abovementioned wavelength. The reaction was continued until a plateau was reached. The result of this measurement gives the content of glucose-6-phosphate in the hydrolyzate. From the identical hydrolyzate, the degree of hydrolysis was determined on the basis of the amount of glucose released. Based on the degree of hydrolysis, we are able to relate the content of glucose-6-phosphate to the proportion of hydrolyzed starch in the fresh weight. For this, 10 µl hydrolyzate was neutralized with 10 µl 0.7 M NaOH and then diluted 1:100 with water. 4 µl of this dilution was mixed with 196 µl measuring buffer (100 mM imidazole pH 6.9; 5 mM $MgCl_2$, 1 mM ATP, 0.4 mM NADP) and used for determining the basic absorption. The reaction was [started] by adding 2 µl enzyme mix (hexokinase 1:10; glucose-6-phosphate dehydrogenase from yeast 1:10 in measuring buffer) and monitored at 340 nm up to the plateau. The measurement principle corresponds to that for the first reaction.

The result of this measurement shows the amount of glucose (in mg) that was released in the course of hydrolysis from the starch present in the starting material. Next, the results from the two measurements provide a basis for expressing the content of glucose-6-phosphate per mg of hydrolyzed starch. Instead of relating the amount of glucose-6-phosphate to the fresh weight of the sample, this calculation relates the amount of glucose-6-phosphate only to the portion of the starch that was completely hydrolyzed to glucose and is therefore to be regarded as the source of the glucose-6-phosphate.

6) Determination of Swelling Power (SP) and Solubility in Hot Water

The swelling power and the solubility in hot water of a 3% (w/v) starch suspension at 90° C. were determined by the method of Leach et al. (Cereal Chemistry 36, (1959), 534-544).

For this, the starch suspension was incubated for 30 minutes with continuous shaking (200 rpm) at 90° C. and, after cooling to room temperature, centrifuged for 15 minutes at 700×g. The resultant supernatant was removed completely and, for determination of the amount of soluble matter, was dried completely for 48 hours at 37° C. and then weighed. The centrifugation residue represented the swollen starch gel, the weight of which is determined gravimetrically.

The Following Formulas are Used:

Swelling power (g/g)=weight of gel/(initial weight of starch−soluble matter) Solubility in hot water at 90° C. in %=weight of dried supernatant/initial weight of starch×100

7) Determination of Apparent Amylose Content

Determination of apparent amylose content was based on the method of Juliano (1971, Cereal Science Today 16 (10): 334-340).

For each sample, twice 50 mg maize or wheat meal (flour) or maize or wheat starch was weighed in 100 ml Erlenmeyer flasks and moistened successively with 1 ml 95% ethanol and 9 ml 1M NaOH.

In parallel, for construction of a standard curve, flasks with defined amounts of pure amylose were treated in the same way as the meal/starch samples. For this purpose it is possible to use for example maize starch from Sigma-Aldrich (order No. S4126, batch number: #015K0144) which according to manufacturer data has a content of apparent amylose of 27 wt. % and an amylopectin content of 73 wt. %.

For thorough mixing, the flasks were swirled briefly and then incubated for 20 minutes on a boiling water bath, with gentle shaking. After cooling for 5-10 minutes at room temperature (RT) the volume was made up to 100 ml with water.

A 100 µl aliquot was mixed with 1 ml of measuring solution (10 mM acetic acid, 0.004% (w/v) $I_2$; 0.04% (w/v) KI), stirred well, and the absorption at 620 nm was determined against a corresponding blank value. The amylose content was calculated by means of the amylose standards that are used for constructing a calibration curve.

8) Analysis of Maize or Wheat Starch Using the Rapid Visco Analyzer (RVA)

The principle of this analysis is that a suspension of water and maize starch is submitted to a defined temperature and shearing protocol, recording the viscosity of the suspension continuously. The measuring instrument used is an RVA Super3 from the company Newport Scientific (Macclesfield, UK) with the corresponding software "Thermocline for Windows", Version 2.3.

For the analysis, 2.5 g maize/wheat starch (initial weight as pure dry weight of the sample material, corrected to 0% moisture) was weighed in a measuring vessel, 25 ml water was added, and after inserting a stirrer, the measuring vessel was mounted in the equipment.

The following temperature and shearing profile was applied:

| Time     | Type        | Value    |
|----------|-------------|----------|
| 00:00:00 | Temp        | 50° C.   |
| 00:00:00 | Speed       | 960 rpm  |
| 00:00:10 | Speed       | 160 rpm  |
| 00:01:00 | Temp        | 50° C.   |
| 00:04:45 | Temp        | 95° C.   |
| 00:07:15 | Temp        | 95° C.   |
| 00:11:00 | Temp        | 50° C.   |
| 00:12:30 | End of test |          |

At the end of the measurement, the following parameters were determined:
Peak viscosity (highest viscosity between 2 and 8 minutes measuring time)
Trough viscosity (lowest viscosity between 6 and 12 minutes measuring time)
Final viscosity (viscosity at the end of measurement after 12.5 minutes)
Breakdown=peak−trough
Setback=final−trough
Pasting temperature (temperature at which, in a time interval of 0.5 minutes, the viscosity changes by more than 50 cP)
Peak time (time at which the peak viscosity is reached)

9) Extraction of Maize Starch

Extraction of maize starch was based on the method of wet starch extraction described by the Corn Refiners Association (http://www.corn.orq/). 10-50 g of maize grains was weighed and, to disrupt the protein matrix, was incubated in excess with 0.2% sulfurous acid for three days at 50° C. The grains were then washed with water and dried briefly. Comminution was carried out in a Retsch ultracentrifugal mill ZM100 with 2 mm sieve (Retsch, Haan, Germany). The comminuted material was transferred to a beaker, 20% NaCl solution was added, and it was left to stand for at least 30 min. The starch forms a sediment and the lipids float to the surface. The top layer (germs) was poured off and the sediment was resuspended in the remaining supernatant. Then the starch was purified further in several sieving steps. First the sample was passed through a 500 μm test sieve (DIN 4188), then through a 200 μm Retsch analysis sieve (DIN 4188) and lastly through a 125 μm sieve (ISO 3310-1) and then rinsed with NaCl (2-3 l) by means of a pressure sprayer, until the drips under the sieve no longer contained starch. This pre-purified starch was sedimented overnight at room temperature and then the supernatant was poured off apart from approx. 5 mm above the sediment. The starch was transferred to centrifuge tubes and centrifuged in a Heraeus Varifuge (Heraeus, Hanau, Germany) at room temperature at 3500 rpm for 10 min. Then the starch-protein layer at the top (generally of a different color) is scraped off and discarded.

Several washing steps were then carried out, first with 0.2M sodium acetate pH 4.6 (centrifugation as above, 5 min), and after each washing step the starch-protein layer was scraped off again. Then digestion was carried out in 0.2M sodium acetate pH 4.6 with 1% bromelain (from AppliChem, Darmstadt, Germany) and 1% pepsin (from AppliChem, Darmstadt, Germany) and incubated at 37° C. for one hour on a Rotator (vertical shaker; Fröbel, Lindau, Germany). It was then centrifuged (see above) and the supernatant was discarded. The starch-protein layer was discarded again and the pellet was resuspended in tap water and centrifuged (see above, 3000 rpm). Once again this was followed by mechanical separation of the protein layer present on the pellet, which was generally clearly demarcated. Another four washing steps with water were carried out, as described above. Then the pellet was washed four times with 80% technical ethanol, and centrifuged (see above, 3000 rpm). Finally it was washed once with acetone, for defatting the starch, and dried at room temperature for two days under an exhaust hood.

As an alternative to the method described above, the starch extraction method described by Eckhoff et al. (Eckhoff, S. R., Rausch, K. D., Fox, E. J., Tso, C. C., Wu, X., Pan, Z., and Buriak, P. 1993. A laboratory wet-milling procedure to increase reproducibility and accuracy of product yields. Cereal Chem. 1993, 70:723-727) was used (see Examples 6 and 7).

10) Detection of Branching Enzyme Activity by Means of Activity Gel

Figure 2:
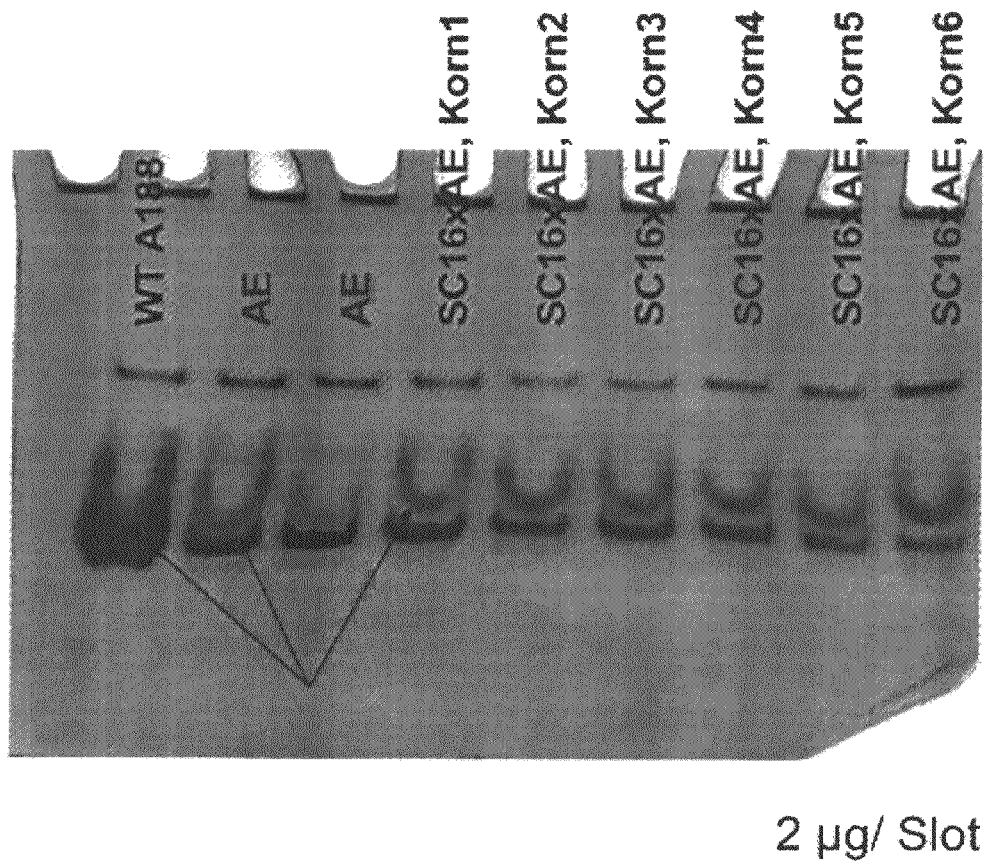
FIG. 2 shows enzyme activities in which protein extracts were separated in a polyacrylamide gel and incubated.

The various branching enzyme activities in unripe maize grains were detected by means of activity gels (zymograms, cf. FIG. 2), in which protein extracts were separated under native conditions in a polyacrylamide gel and then incubated with appropriate substrates. The resultant reaction product (starch) was stained in the gel with Lugol solution (2% (w/v) KI; 0.2% (w/v) $I_2$).

Individual unripe maize grains (approx. 15 days after flowering—measured from the day when flowering began) were quick-frozen in liquid nitrogen and homogenized in 150-200 μl cold extraction buffer (50 mM Tris/HCl pH 7.6, 2.5 mM EDTA, 2 mM DTT, 4 mM PMSF, 0.1% (w/v) glycogen, 10% (v/v) glycerol). After centrifugation (15 min, 13000 g, 4° C.) the clear supernatant was transferred to a fresh reaction vessel and an aliquot of the extract was used for determination of protein content according to Bradford (1976, Anal Biochem 72: 248-254).

The protein extracts were separated by means of a continuous 7.5% polyacrylamide gel (7.5% AA/BAA 37.5:1; 25 mM Tris/HCl pH 7.6, 192 mM glycine, 0.1% (w/v) APS, 0.05% (v/v) TEMED) using single-strength running buffer (25 mM Tris/HCl, 192 mM glycine). Before loading the gels, a preliminary run for removal of radicals is carried out for 30 minutes at 8 mA and 4° C. For each sample, 2 μg protein was applied and electrophoresis was carried out for 2-2.5 hours at 8 mA and 4° C. Then the gels were washed five times in washing buffer (0.1M sodium citrate pH 7.0) for 5 minutes on ice. Next, the gels were incubated in 15 ml incubation buffer (0.1M sodium citrate pH 7.0, 50 mM glucose-1-phosphate, 1 mM AMP, 0.95 Units/ml phosphorylase A from rabbit) overnight at room temperature, shaking continuously. The starch that formed was stained with Lugol solution.

11) Detection of the Expression of GWD from *Curcuma longa* by Quantitative PCR

RNA was prepared from leaf samples that were frozen in liquid nitrogen directly after sample collection. After homogenization with a 4 mm steel ball (Retsch mill, 30 Hz, 45 s) the RNA was prepared with the "SV 96 Total RNA Isolation System" from Promega according to protocol No. 294 (Promega). The RNA was treated in each case with 10 μl "RQ1 RNase-free DNase" (Promega) according to the manufacturer's instructions.

Quantitative RT-PCR was carried out with the reagents of the "Access RT-PCR System" from Promega. The amplicon for R1 from *Curcuma longa* had a length of 105 by (base pairs). Cl_R1-F1 (TggATAAATACAAAgAgTgAAgCAg=SEQ ID No. 11) and Cl_R1-R1 (ggACATTgAAggTgTTg-TAAAgg=SEQ ID No. 12) were used as amplification primers. The doubly fluorescence-labeled oligonucleotide Cl_R1-FAM (FAM-cttcgtcgtccaaacaagaccacag-TAMRA=SEQ ID NO. 13) was used as Taqman probe.

The amplicon for catalase from maize had a length of 73 base pairs. The primers Zm_Cat-F1 (GTGGGAGCAACTC-CAGCTT=SEQ ID No. 14), Zm_Cat-R1 (CGGTGA-GGGCAGAGTTGTT=SEQ ID No. 15) and the doubly fluorescence-labeled TaqMan probe Cat-VIC (VIC-ACTCCG-GCGCCCCCGT-TAMRA 0 SEQ ID No. 16) were used for the amplification.

The 30-µl reaction mixture contained buffer (singly), 3 mM MgSO₄, in each case 500 nM amplification primer, 100 nM probe Cl_R1-FAM or Cat-VIC, in each case 0.2 mM deoxy-ribonucleotides, in each case 0.6 µl reverse transcriptase and Tfl-polymerase (corresponding to protocol 294). Each mixture contained 350 ng total RNA.

The reaction conditions for the RT-PCR were: 30 min 55° C., 2 min 94° C., 40×(15 s 94° C., 1 min 60° C.). The fluorescence signal was recorded by the ABI Prism 7700 instrument (Applied Biosystems) in each case during the combined annealing/extension phase.

In each case, mixtures without reverse transcriptase in the mixture were conducted in parallel, as controls.

The relative expression was calculated according to M. W. Pfaffl, A new mathematical model for relative quantification in real-time RT-PCR, Nucleic Acids Research 2001, Vol. 29, No. 9 00. The expression of R1 from *Curcuma longa* was standardized to the expression of catalase.

12) Determination of the Copy Number for GWD from *Curcuma* by PCR

DNA was prepared from leaf samples that were frozen in liquid nitrogen directly after sample collection. After homogenization with a 4 mm steel ball (Retsch mill, 30 Hz, 45 s) it was prepared with the Qiagen Kit "DNeasy plant Mini kit". Quantitative PCR was carried out with the following amplicons:

The amplicon for R1 from *Curcuma longa* had a length of 105 by (base pairs). Cl_R1-F1 (TggATAAATACAAAgAgT-gAAgCAg=SEQ ID No. 11) and Cl_R1-R1 (ggACATTg-AAggTgTTgTAAAgg=SEQ ID No. 12) were used as amplification primers. The doubly fluorescence-labeled oligonucleotide Cl_R1-FAM (FAM-cttcgtcgtccaaacaagaccacag-TAMRA=SEQ ID NO. 13) was used as Taqman probe.

The amplicon for catalase from maize had a length of 73 base pairs. The primers Zm_Cat-F1 (GTGGGAGCAACTC-CAGCTT=SEQ ID No. 14), Zm_Cat-R1 (CGGTGAG-GGCAGAGTTGTT=SEQ ID No. 15) and the doubly fluorescence-labeled TaqMan probe Cat-VIC (VIC-ACTCCG-GCGCCCCCGT-TAMRA=SEQ ID No. 16) were used for the amplification.

The HotStar Mastermix from Qiagen was used for the reactions (30 µl). The reaction mixture contained Mastermix (singly) for which the final concentration of $MgCl^{2+}$ was adjusted to 3 mM. The final concentrations of the amplification primers were in each case 300 nM and that of the probe Cl_R1-FAM or Cat-VIC was 100 nM. According to the manufacturer's data the final concentration of the deoxy-nucleotides was 200 µM and the enzyme concentration was 1.5 units Taq-polymerase/per 30-µl preparation. Two preparations were analyzed in each case with 50 ng or 5 ng DNA as template per preparation.

The reaction conditions for the PCR were: 2 min 94° C., 40×(15 s 94° C., 1 min 60° C.). The fluorescence signal was recorded with the ABI Prism 7700 instrument (Applied Biosystems) in each case during the combined annealing/extension phase.

The relative copy numbers were calculated according to M. W. Pfaffl, A new mathematical model for relative quantification in real-time RT-PCR, Nucleic Acids Research 2001, Vol. 29, No. 9 00. The amount of DNA was standardized on the basis of the amplification signal for catalase.

13) Determination of Light Transmittance

To determine the light transmittance of a starch sample the method of Craig et al. (Cereal Chemistry 66(3), (1989), 173-182, see page 173, column 2 "Light Transmittance (% T) of Starch Pastes) is used. For this, 50 mg of starch (dry weight) are mixed with 5 ml of water and subsequently heated in a boiling water bath for 30 minutes during which the samples are carefully shaken every 5 minutes. The sample is then cooled to room temperature within 5 minutes and the light transmittance (in %) compared with a water sample is determined at 650 nm in a spectrophotometer.

14) Determination of Freeze-Thaw Stability

Freeze-thaw stability is determined in line with the method described by Yuan & Thompson (Cereal Chemistry, 1998, 75 (4) 571-573). A 5% (w/w) starch solution is heated to 88° C. and incubated at 88° C. for 10 minutes. After the sample has cooled to room temperature, about 4 ml are transferred into a 5 ml vessel of defined weight. The weight of the vessel including its contents (starch suspension) is then determined.

Two vessels are filled for each starch sample. One sample is immediately centrifuged at 5000 rpm for 10 minutes, while the other sample is frozen at −18° C. The aqueous supernatant of the centrifuged sample is removed by means of a Pasteur pipette and the weight of the vessel containing the starch paste is determined. The water loss of the control sample in % is obtained from the weight of the sample after centrifuging and decanting (pipette), divided by the weight of the paste before centrifuging multiplied by 100.

For the subsequent freeze-thaw cycle, the vessels are taken from the freezer compartment and thawed at room temperature (4 hours). The thawed samples are likewise centrifuged at 5000 rpm for 10 minutes and, to determine the water loss, treated like the control samples.

15) Brabender Analysis of Maize or Wheat Starch by Means of a Brabender Visco-Amylograph The principle of the analysis corresponds to that of method 8, but differs with regard to the sample quantity and concentration used and also the analysis time. The instrument used is a Micro Visco-Amylo-Graph from Brabender GmbH & Co. KG, Duisburg, Germany.

A 5.5% (w/w) starch suspension (total weight 110 g) is heated to 50° C. at the start of analysis and subsequently, with continuous stirring at 250 rpm, heated to 95° C. at a heating rate of 1.5° C./min. After 30 minutes at 95° C., the sample is cooled back down to 50° C. at a cooling rate of 1.5° C./min, and is incubated at 50° C. for a further 30 minutes. The viscosity profiles are evaluated automatically by means of the following software: Micro Visco AG, WinVis-2.4.7, VisCorr-2.1.2, Univ.Eval-1.1.2.

16) Determination of RS and RDS

Determination of RS, SDS and RDS is done via the method of Englyst et al. (Europ. J. of Clinical Nutrition 46 (Suppl. 2), (1992), S 33-50, see in particular the following sections from Englyst et al., page S35-S36: "Reagents, Apparatus, Spectrophotometer"; page S36-S37, paragraph "Measurement of free glucose (FG)"; page S38, paragraph "Measurement of RDS and SDS"; S39 for RS determination: measurement of $RS_3$).

EXAMPLE 1

Production of a Construct for the Transformation of Maize Plants that Display Detectable GWD Gene Expression The pMZ12 plasmid served as the starting plasmid for production of the pSC16 plasmid, which was used for the transformation of maize plants. This plasmid contains the ColE1 origon of the pBR322 plasmid (Bolivar et al., 1977, Gene 2, 95-113) and a bacterial selection marker, which imparts resistance to the antibiotic gentamicin (Wohlleben et al., 1989, MGG 217, 202-208). In addition, this plasmid contains a right and a left T-DNA border sequence. Between these T-DNA border sequences, the plasmid contains a bar gene from *Streptomyces hygroscopicus* (White et al., 1990, NAR 18, 1062; EMBL Acc.: X17220), which imparts resistance to the herbicide glufosinate. Expression of the bar gene is initiated by the promoter of the actin gene from rice (McElroy et al., 1990, Plant Cell 2, 163-171). For stabilization of expression of the bar gene, the 1st intron of the actin gene from rice (McElroy et al., 1990, Plant Cell 2, 163-171) is inserted between the actin promoter and the sequence encoding the bar protein. The sequence encoding the bar protein is followed by the polyadenylation signal of the nopaline synthase gene from *Agrobacterium tumefaciens* (Depicker et al., 1982, J. Mol. Appl. Gent. 1, 561-573). The ubiquitin promoter from *Zea mays* (Christensen et al. 1992, Plant Mol. Bio. 18, 675-689) was inserted in the pMZ12 plasmid, followed by the 1st intron of the ubiquitin gene from *Zea mays* (Christensen et al. 1992, Plant Mol. Bio. 18, 675-689), followed by the coding sequence of the GWD (R1) gene from *Curcuma longa* (see SEQ ID NO 3) with the aid of the Gateway system from Invitrogen and so-called attB recognition sequences (Hartley J. L., Temple G. F., Brasch M. A. (2000). DNA cloning using in vitro site-specific recombination. Genome Research, 10, 1788-1795), followed by the polyadenylation signal of the nopaline synthase gene from *Agrobacterium tumefaciens* (Depicker et al., 1982, J. Mol. Appl. Gent. 1, 561-573) in addition to the selection cassette between the left and right T-DNA border sequence. The resultant plasmid was designated as pSC16.

EXAMPLE 2

Production and Analysis of Maize Plants that have Detectable GWD Expression

Ten days after pollination, immature embryos of maize plants (variety A188) were isolated and were transformed according to the method described in Ishida et al. (1996, Nature Biotechnology 14, 745-750), using *Agrobacterium tumefaciens*, containing the pSC16 plasmid as cointegrate. So-called TO plants resulting from this transformation were grown in the greenhouse. The plants obtained were given the designation SC16-X, where X denotes independent plants resulting from the transformation.

Maize plants (TO plants) resulting from transformation with the expression vector pSC16 were cultivated in soil in the greenhouse and were pollinated with wild-type (variety A188) pollen. Meal (flour) was produced from individual, ripe grains (T1 seeds). For this, individual grains were comminuted in a ball mill (from Retsch, Haan, Germany, model MM300) for 30 seconds at a frequency of 30 Hz. Then the starch phosphate content in position C6 of glucose molecules of the starch was determined, as described under general methods.

For selected plants, the following results were obtained:

| Designation of the plant | nmol C6-phosphate per mg starch |
|---|---|
| SC16-1 | 1.9 |
| SC16-2 | 1.4 |
| SC16-3 | 1.6 |
| WT A188 | 0.1 |

As can be seen from the table, independent lines could be identified, which have an increased phosphate content in position C6 of the glucose monomers of the starch compared with corresponding wild-type plants (A188) that are not genetically modified. The increase in phosphate content in lines with the designation pSC16 can be attributed to the detectable expression of a GWD gene from *Curcuma longa* (SEQ ID No. 3).

EXAMPLE 3

Production of Plants that have Both the Amylose Extender Character and Detectable Expression of a Glucan-Water Dikinase In each case 30 T1 seeds from plants of various lines with the designation SC16-1-X, which have detectable expression of a GWD gene from *Curcuma longa* compared with the wild-type maize plants of variety A188, were cultivated in the greenhouse and the resultant plants were sprayed with 0.5% Basta® (Bayer CropScience) solution. About half the treated plants of the pSC16-1-X lines reacted sensitively to the treatment with Basta®, so it could be concluded that they did not contain a bar gene imparting resistance to Basta®. For the resistant plants it could accordingly be concluded that the T-DANN(s) was integrated at one place in the genome or were integrated at places in the genome that were so close together that they do not segregate. These plants were self-pollinated and the resultant T1S1 seeds from T1 plants, which were resistant to treatment with Basta®, were again sown in the greenhouse, treated with Basta® as just described, self-pollinated and resultant T1 S2 seeds were produced. Then the same treatment with Basta® was carried out with T1S2 plants of these lines: various T1S2 plants were identified, for which all descendants were resistant to Basta®. It could therefore be concluded that the starting T1S2 plants were homozygous for the integrated T-DNA. T1S2 seeds from homozygous plants of line SC16-1 were again sown and various plants were in each case pollinated with pollen of the amylose-extender mutant ae1 of variety W64A (cf. General Methods), which was obtained from the "Maize Genetics Cooperation Stock Center", Illinois, USA (http://maizecoop.cropsci.uiuc.edu/). The resultant cross-bred descendants were designated SC16 x ae1.

EXAMPLE 4

Analysis of Plants that have Both the Amylose Extender Character and Detectable Expression of a Glucan-Water Dikinase From the SC16 x ae1 plants resulting from the crossing described in Example 3, in each case F1 seeds were harvested, sown again and self-pollinated. F1 S1 seeds and plants from F1 plants of this crossing were investigated with respect to the copy number of the inserted GWD gene from *Curcuma longa* and the amylose content. Seeds that had an amylose content of at least 40% (see General Methods) were cultivated and the F1S1 plants, which then contained a copy number of 2 for the GWD transgene from *Curcuma* (see General Methods), were used for the production of doubly homozygous F1S2 seeds in the greenhouse. The reduced branching enzyme activity was detected with the aid of activity gels (see FIG. 2 and "General methods":

| Designation of the plant | No. of the homozygous seed | % amylose |
|---|---|---|
| SC16 × ae1 | 1 | 51.1 |
|  | 2 | 49.4 |
|  | 3 | 45.9 |
|  | 4 | 49.8 |

-continued

| Designation of the plant | No. of the homozygous seed | % amylose |
|---|---|---|
|  | 5 | 52.4 |
| SC 16-1 (mother) | 1 | 25.5 |
|  | 2 | 26.0 |
| ae1 (father) | 1 | 52.4 |
|  | 2 | 51.9 |
| WT A188 | 1 | 26.0 |
|  | 2 | 26.5 |

| Designation of the plant | No. of the homozygous plant | Copy number |
|---|---|---|
| SC16 × ae1 | 1 | 2 |
|  | 2 | 2 |
|  | 3 | 2 |
|  | 4 | 2 |
|  | 5 | 2 |
| SC 16-1 (mother) | 1 | 2 |
|  | 2 | 2 |
| ae1 (father) | 1 | 0 |
|  | 2 | 0 |
| WT A188 | 1 | 0 |
|  | 2 | 0 |

EXAMPLE 5

Analysis of the Maize Starch from Maize Grains from Doubly Homozygous Plants of the Crossing SC16 x ae1

1. Amylose Content

The amylose content of starches produced from doubly homozygous seeds of the crossing SC16 x ae1, the parent lines and of the wild-type variety A188 was determined as described under General Methods. The following results were obtained:

| Designation of the plant | Amylose (% dry weight) |
|---|---|
| SC16 × ae1 | 43.1 |
| SC 16 | 25.0 |
| ae1 | 52.9 |
| WT A188 | 27.0 |

2. Analysis of the Viscosity Properties of Maize Starch Using the Rapid Visco Analyzer (RVA)

The viscosity properties of 10% (w/v) suspensions of various maize starches were investigated using the method "Analysis of maize meal (flour) by RVA" (AACC Method 61-02):

| Sample: | Wild-type (A188) | SC16 | ae1 | SC16 × ae1 | Amylogel ® | Hylon ® VII |
|---|---|---|---|---|---|---|
| Peak viscosity (cP) | 1844 | 2069 | 2 | 1594 | 40 | 2 |
| Trough (cP) | 329 | 525 | 0 | 1517 | 32 | 0 |
| Breakdown (cP) | 1515 | 1544 | 2 | 77 | 8 | 2 |
| Final viscosity (cP) (12.5 min) | 705 | 1088 | 0 | 1580 | 42 | 0 |
| Setback (cP) (12.5 minutes) | 376 | 563 | 0 | 63 | 10 | 0 |
| Peak time (min) | 3.94 | 3.94 | 2.02 | 6.55 | 6.58 | 2.02 |
| Pasting temperature (° C.) | 73.25 | 72.35 | Error | 85.35 | Error | Error |

The results show a greatly altered RVA profile (see FIG. 1) of the starch according to the invention of the crossing SC16 x ae1 compared with the parent lines, mainly with amylose extender (ae1), and compared with conventional high-amylose maize starch (Amylogel®, Hylon® VII). The starch of the amylose-extender line and the commercially available high-amylose maize starches (Amylogel®, Hylon® VII) do not undergo gelatinization to a significant extent, accordingly no pasting temperature can be determined in RVA analysis (ERROR). The starch sample of the crossing SC16 x ae1 undergoes gelatinization at a much higher temperature than the SC16 or wild-type starch. The final viscosity of the starch according to the invention is greater than for SC16 or wild-type starches and shows a very low setback.

3. Swelling Power and Solubility in Hot Water

The swelling power and the solubility in hot water of starches produced from doubly homozygous seeds of the crossing SC16 x ae1, the parent lines and from wild-type plants were determined as described under General Methods. The following results were obtained:

| Designation of the plant | Swelling power of starch [g/g] | Solubility in % |
|---|---|---|
| SC16 × ae1 | 12.6 | 12.4 |
| SC 16 | 27.2 | 7.1 |
| ae1 | 5.4 | 6.9 |
| WT A188 | 23.2 | 20.9 |
| Hylon VII ® | 5.0 | 6.4 |
| Amylogel ® | 5.2 | 5.6 |

The results represent the mean value from two independent measurements. They show that both the starch of the amylose-extender mutant (ae) and the commercial products (Nylon VII®, Amylogel®) have a far lower swelling power and a far lower solubility than the starches according to the invention of the crossing SC16 x ae1.

4. Phosphate Content in Position C6 of the Glucose Monomers of Starch

The C6-phosphate content of starches produced from doubly homozygous seeds of the crossing SC16 x ae1, the parent lines and from the wild-type variety A188 was determined as described under General Methods. The following results (mean value of two measurements) were obtained:

| Designation of the plant | nmol C6-phosphate/mg starch |
|---|---|
| SC16 x ae1 | 20.9 |
| SC 16-1 (mother) | 4.3 |
| ae1 (father) | 1.0 |
| WT A188 | 0.1 |

Overall, the combination SC16 x ae1 shows a significant increase in phosphate content in position C6.

EXAMPLE 6

Analysis of the Maize Starch from Maize Grains from Doubly Homozygous Plants of the Crossing SC16 x ae1 Kept in the Open The SC16 x ae1 maize plants described in Examples 4 and 5 were kept in the open and harvested after about 4 months. After the harvest, starch was extracted by means of the method of Eckhoff et al. (Eckhoff, S. R., Rausch, K. D., Fox, E. J., Tso, C. C., Wu, X., Pan, Z., and Buriak, P. 1993. A laboratory wet-milling procedure to increase reproducibility and accuracy of product yields. Cereal Chem. 1993, 70:723-727) and subsequently analyzed.

1. Amylose Content

The amylose content of starches prepared from doubly homozygous seeds of the crossing SC16 x ae1, the parent lines and from the wild-type variety A188 was determined as described under General Methods. The following results were obtained:

| Designation of the plant | Amylose (% dry weight) |
|---|---|
| SC16 x ae1 | 54.8 |
| SC 16 | 29.3 |
| ae1 | 67.5 |
| WT A188 | 31.4 |

2. Analysis of the Viscosity Properties of Maize Starch Using the Rapid Visco Analyzer (RVA)

The viscosity properties of 10% (w/v) suspensions of various maize starches were investigated by means of the method "Analysis of maize flour by RVA" (AACC method 61-02):

| Sample: | ae1 | SC16 x ae1 |
|---|---|---|
| Peak viscosity (cP) | 0 | 2249 |
| Trough (cP) | 0 | 2073 |
| Final viscosity (cP) (12.5 min) | 0 | 2334 |
| Setback (cP) (12.5 minutes) | 0 | 261 |
| Peak Time (min) | 0 | 6.42 |
| Pasting temperature (° C.) | Error | 85.35 |

The results show a distinctly modified RVA profile for the starch of the crossing SC16 x ae1 according to the invention compared with amylose extender (ae1). The starch of the amylose extender line does not gelatinize, so that it is also impossible to determine a pasting temperature in RVA analysis (ERROR).

3. Swelling Power

The swelling power of starches, prepared from doubly homozygous seeds of the crossing SC16 x ae1, the parent lines and from wild-type plants was determined as described under General Methods. The following results were obtained:

| Designation of the plant | Swelling power of starch [g/g] |
|---|---|
| SC16 x ae1 | 15.2 |
| SC 16 | 21.8 |
| ae1 | 5.5 |
| WT A188 | 22.4 |

The results represent the rounded mean of two independent measurements. They show that the present invention starch of the crossing SC16 x ae1 has distinctly increased swelling power compared with the starch of the amylose extender mutant (ae1).

4. Phosphate Content at in Position C6 of the Glucose Monomers of Starch

The C6-phosphate content of starches produced from doubly homozygous seeds of the crossing SC16 x ae1, the parent lines and from the wild-type variety A188 was determined as described under General Methods. The following results (mean value of two measurements) were obtained:

| Designation of the plant | nmol C6-phosphate/mg starch |
|---|---|
| SC16 x ae1 | 21.3 |
| SC 16-1 (mother) | 5.5 |
| ae1 (father) | 1.1 |
| WT A188 | 0.3 |

Overall, the combination SC16 x ae1 shows a significant increase in phosphate content in position C6.

Figure 3:
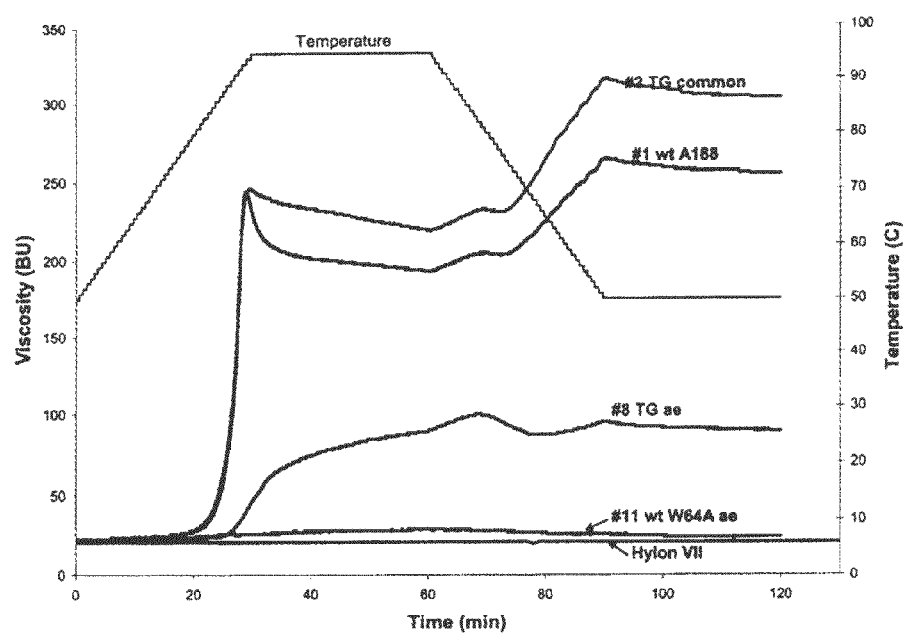
FIG. 3 shows the Brabender profile of starch from the crossing SC16 x ae1 compared with the parent lines.

5. Brabender Analysis (See Also FIG. 3)

| Designation of the plant | Pasting temperature in ° C. | Peak viscosity in Brabender units (BUs) | Final viscosity in BUs |
|---|---|---|---|
| SC16 x ae1 | 90.8 | 100 | 89 |
| ae1 (father) | Not determinable | 29 | 24 |
| WT A188 | 83.4 | 244 | 254 |
| Hylon VII ® | Not determinable | 28 | 21 |

6. Freeze-Thaw Stability

| Designation of the plant | % water loss after one freeze-thaw cycle |
|---|---|
| SC16 x ae1 | 63 |
| ae1 (father) | 77 |
| WT A188 | 41 |

7. Light Transmittance of Starch Pastes

| Designation of the plant | Light transmittance at 650 nm |
| --- | --- |
| SC16 × ae1 | 12.3 |
| ae1 (father) | 3.4 |
| WT A188 | 20.8 |

8. RDS Content of Native Maize Starch

| Designation of the plant | RDS content in % |
| --- | --- |
| WT A188 | 30.1 |
| SC16 | 37.2 |
| ae1 (father) | 13.8 |
| SC16 × ae1 | 10.1 |

9. RDS Content of Processed Starch Compared with RDS Content of Correspondingly Processed Starch from A188 Maize Wild-Type Plants (100%)

| | RVA[1] | Hot-moist treatment[2] | Miniloaf[3] |
| --- | --- | --- | --- |
| A188 | 100.0 | 100.0 | 100.0 |
| SC16 (GWD) | 98.7 | 142.5 | n.d. |
| SC16 × ae1 | 88.6 | 64.5 | 64.0 |
| ae1 (father) | 88.8 | 73.6 | 76.0 |

[1]RVA = A 10% (w/w) starch suspension was heated up and cooled back down with constant stirring, as described in AACC method 61-02. The resulting gel was left covered at room temperature for 24 hours before aliquots for determining digestibility (RDS, SDS and RS) were taken.
[2]Hot-moist treatment = A 50% (w/w) starch-water mixture was covered and incubated in a water bath at 95° C. for 30 minutes. The hot-moist treated starch was subsequently stored at 4° C. for two days before the batch was used to determine digestibility (RDS, SDS, RS).
[3]Miniloaves = A mixture of 80% (w/w) starch, 17% (w/w) wheat gluten and 3% (w/w) water-soluble wheat constituents was prepared. The weight of this mixture being regarded as 100%, the following were also added: 2% (w/w) salt, 1% (w/w) sugar, 4% (w/w) yeast and 5% (w/w) shortening. The ingredients were mixed for one minute before 60% (w/w) water was added and the mixture was mixed and kneaded for a further five minutes. After resting for 10 minutes, aliquots of the minidough thus produced were introduced into DSC crucibles and hermetically sealed. The baking simulation in the DSC instrument started at a temperature of 10° C. and was raised to 110° C. at a heating rate of 10° C./minute. Subsequently, the DSC crucibles were cooled down to 20° C. at a temperature rate of 10° C./minute. The resulting miniloaves were stored at room temperature for three days before the crucibles were opened and the miniloaves were used to determine digestibility (RDS, SDS, RS).

EXAMPLE 7

Production and Analysis of Plants that have Both the Amylose Extender Character and Detectable Expression of a Glucan-Water Dikinase from *Solanum tuberosum*

Standard methods were used to create in the background variety A188, by *agrobacterium* transformation, transgenic maize plants having a detectable expression of a GWD gene from *Solanum tuberosum* (see SEQ ID No. 1) compared with the A188 maize wild-type plants. These were repeatedly self-pollinated to produce plants which were homozygous with regard to the GWD gene introduced. Seeds of these homozygous plants, which were designated as HN3, were again sown and each pollinated with pollen from the amylose extender mutant ae1 of variety W64A. The resulting crossing descendants were designated HN3 × ae1. These were self-pollinated and used to produce doubly homozygous plants, i.e. maize plants which were homozygous not only for the GWD gene introduced but also for the amylose extender mutation.

Then, maize starch was extracted by the method of Eckhoff et al. (Eckhoff, S. R., Rausch, K. D., Fox, E. J., Tso, C. C., Wu, X., Pan, Z., and Buriak, P. 1993. A laboratory wet-milling procedure to increase reproducibility and accuracy of product yields. Cereal Chem. 1993, 70:723-727) and then the amylose content, the C6 phosphate content, the swelling power and the viscosity properties in the Brabender were analyzed.

1. Amylose Content

The amylose content of starches produced from doubly homozygous seeds of the crossing HN3 × ae1, the parent lines and the wild-type variety A188 was determined as described under General Methods. The following results were obtained:

| Designation of the plant | Amylose (% dry weight) |
| --- | --- |
| HN3 × ae1 | 42.0 |
| HN3 | 25.3 |
| ae1 | 50.2 |
| WT A188 | 25.8 |

2. Swelling Power

The swelling power and the hot water solubility of starches produced from doubly homozygous seeds of the crossing HN3 × ae1, the parent lines and from wild-type plants were determined as described under General Methods. The following results were obtained:

| Designation of the plant | Swelling power of starch [g/g] |
| --- | --- |
| HN3 × ae1 | 11.63 |
| ae1 | 5.8 |
| WT A188 | 22.2 |

The results represent the mean value of two independent measurements. They show that the present invention starch of the crossing HN3 × ae1 has a distinctly increased swelling power compared with the starch from the amylose extender mutant (ae).

3. Phosphate Content in Position C6 of the Glucose Monomers of Starch

The C6-phosphate content of starches produced from doubly homozygous seeds of the crossing HN3 × ae1, the parent lines and from wild-type variety A188 was determined as described under General Methods. The following results (mean value of two measurements) were obtained:

| Designation of the plant | nmol C6-phosphate/mg starch |
| --- | --- |
| HN3 × ae1 | 29.6 |
| HN3-1 (mother) | 5.5 |
| ae1 (father) | 0.7 |
| WT A188 | 0.2 |

Overall, the combination HN3 × ae1 shows a significant increase of the phosphate content in position C6.

4. Analysis of the Viscosity Properties of Maize Starch by Rapid Visco Analyzer (RVA)

The viscosity properties of 10% (w/v) suspensions of various maize starches were investigated by means of the method "Analysis of maize flour by RVA" (AACC method 61-02). The peak viscosity of the starch from two selected lines of the crossing HN3 × ae1 was 1698 centipoise (compared with the 30 centipoise of the ae1 mutant of the variety W64A), the final viscosity after 12.5 minutes was 1959 or 2164 centipoise (compared with the 5 centipoise of the ae1 mutant of the variety W64A), the trough viscosity was 1586 or 1611 centipoise (compared with the 4 centipoise of the ae1 mutant of the variety W64A) and the pasting temperature was 82.75° C. or 83.20° C. (compared with "error" in the case of the ae1 mutant of the variety W64A, i.e. not determinable using the AACC method).

The invention claimed is:

1. An isolated maize plant cell comprising a heterologous GWD gene and an amylose extender mutation.

2. A maize plant comprising a maize plant cell as claimed in claim 1.

3. The maize plant as claimed in claim 2, wherein said maize plant synthesizes a maize starch that has an increased apparent amylose content relative to maize starch from a corresponding wild-type maize plant, and wherein said maize starch further displays a measurable pasting temperature in an aqueous suspension in RVA analysis, wherein the RVA analysis is measured according to the AACC standard method 61-02.

4. The maize plant as claimed in claim 3, wherein the aqueous suspension is a 10% (w/v) aqueous suspension of the maize starch in water.

5. The maize plant as claimed in claim 3, wherein the maize starch has a phosphate content in position C6 between 15 and 30 nmol C6P/mg starch (dry weight).

6. Reproductive material of the maize plant as claimed in claim 2, wherein said reproductive material comprises the heterologous GWD gene and the amylose extender mutation.

7. Reproductive material of the maize plant as claimed in claim 3, wherein said reproductive material comprises the heterologous GWD gene and the amylose extender mutation.

8. The maize plant cell of claim 1, wherein said GWD gene comprises the coding region of the nucleic acid sequence of SEQ ID NO: 1.

9. The maize plant cell of claim 1, wherein said GWD gene comprises the coding region of the nucleic acid sequence of SEQ ID NO: 3.

10. The maize plant cell of claim 1, wherein said amylose extender mutation comprises a mutation in SEQ ID NO: 5.

11. The maize plant cell of claim 8, further wherein said amylose extender mutation comprises a mutation in SEQ ID NO: 5.

12. The maize plant cell of claim 9, further wherein said amylose extender mutation comprises a mutation in SEQ ID NO: 5.

13. A maize plant comprising the maize plant cell of claim 8.

14. A maize plant comprising the maize plant cell of claim 9.

15. A maize plant comprising the maize plant cell of claim 10.

16. A maize plant comprising the maize plant cell of claim 11.

17. A maize plant comprising the maize plant cell of claim 12.

18. A method for the production of maize starch comprising extracting maize starch from the maize plant as claimed in claim 2.

19. A method for the production of maize starch comprising extracting maize starch from the maize plant as claimed in claim 3.

20. A method for the production of maize starch comprising extracting maize starch from the reproductive material as claimed in claim 6.

21. A method for the production of maize meal comprising grinding the maize plant as claimed in claim 2.

22. A method for the production of maize meal comprising grinding the maize plant as claimed in claim 3.

23. A method for the production of maize meal comprising grinding the reproductive material as claimed in claim 6.

* * * * *